US008236563B2

(12) United States Patent
Lipton et al.

(10) Patent No.: US 8,236,563 B2
(45) Date of Patent: Aug. 7, 2012

(54) METHODS OF DIFFERENTIATING AND PROTECTING CELLS BY MODULATING THE P38/MEF2 PATHWAY

(75) Inventors: Stuart A Lipton, Rancho Santa Fe, CA (US); Shu-ichi Okamoto, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 13/077,752

(22) Filed: Mar. 31, 2011

(65) Prior Publication Data

US 2011/0212070 A1     Sep. 1, 2011

Related U.S. Application Data

(63) Continuation of application No. 09/876,187, filed on Jun. 5, 2001, now Pat. No. 7,919,317.

(60) Provisional application No. 60/209,539, filed on Jun. 5, 2000.

(51) Int. Cl.
    C12N 5/00     (2006.01)
    C12N 5/02     (2006.01)

(52) U.S. Cl. .................. 435/377; 435/366; 435/368

(58) Field of Classification Search .............. None
    See application file for complete search history.

(56) References Cited

U.S. PATENT DOCUMENTS 5,843,780 A    12/1998  Thomson
6,153,591 A    11/2000  Cai et al.
6,200,969 B1    3/2001  Fritz et al.

OTHER PUBLICATIONS

Watanabe et al. (1996) Gene transfer through implantation of embryonal carcinoma cell in the brain. Cell Transplantation 5 (5 Suppl. 1): S9-S12 (abstract only).*
Arsenijevic and Weiss, "Insulin-Like Growth Factor-I is a Differentiation Factor for Postmitotic CNS Stem Cell-Derived Neuronal Precursors: Distinct Actions from Those of Brain-Derived Neurotrophic Factor," *J.Neurosci.* 18(6):2118-2128 (1998).
Bain et al., "Embryonic Stem Cells Express Neuronal Properties in Vitro," *Dev. Biol.* 168(2):342-357 (1995).
Bain et al., "From Embryonal Carcinoma Cells to Neurons: The P19 Pathway," *Bioessys* 16(5):343-348 (1994).
Bhatia et al., "A newly discovered class of human hematopoietic cells with SCID-repopulating activity," *Nat. Med.* 4(9):1038-1045 (1998).
Black and Olson, "Transcriptional Control of Muscle Development by Myocyte Enhancer Factor-2 (MEF2) Proteins," *Annu. Rev. Cell Dev. Biol.* 14:167-196 (1998).
Black et al., "Cooperative transcriptional activation by the neurogenic basic helix-loop-helix protein MASH1 and members of the myocyte enhancer factor-2 (MEF2) family," *J. Biol. Chem.* 271:26659-26663 (1996).
Blaschke et al., "Widespread programmed cell death in proliferative and postmitotic regions of the fetal cerebral cortex," *Development* 122(4):1165-1174 (1996).
Brand, "Molecules in Focus," *Int. J. Biochem. Cell Biol.* 29:1467-1470 (1997).
Breitbart et al., "A fourth human MEF2 transcription factor, hMEF2D, is an early marker of the myogenic lineage," *Development* 118:1095-1106 (1993).
Brooker et al., "Endogenous IGF-1 Regulates the neuronal Differentiation of Adult Stem Cells," *J. Neurosci. Res.* 59:332-341 (2000).
Cao et al., "Stem cell repair of central nervous system injury," *J. Neurosci. Res.* 68:501-510 (2002).
Clem et al., "Prevention of apoptosis by a baculovirus gene during infection of insect cells," *Science* 254:1388-1390 (1991).
D'Amour and Gage, "New tools for human developmental biology," *Nat. Biotechnol.* 18:381-382 (2000).
Deveraux and Reed, "IAP family proteins—suppressors of apoptosis," *Genes Dev.* 13(3):239-252 (1999).
Dunnett et al., "Neuronal cell transplantation for Parkinson's and Huntington's diseases," *Br. Med. Bull.* 53(4):757-776 (1997).
Eiges et al., "Establishment of human embryonic stem cell-transfected clones carrying a marker for undifferentiated cells," *Curr. Biol.* 11:514-518 (2001).
Ekert et al., "Caspase Inhibitors," *Cell Death Differ.* 6(11):1081-1086 (1999).
English et al., "Contribution of the ERK5/MEK5 Pathway to Ras/Raf Signaling and Growth Control," *J. Biol. Chem.* 274(44):31588-31592 (1999).
Filbin, "Myelin-associated inhibitors of axonal regeneration in the adult mammalian CNS," *Nat. Rev.* 4:1-11 (2003).
Fujimoto et al., "Identification of genes differentially expressed by putrescine in HepG2 hepatoblastoma cells," *Hepatol. Res.* 20(2):207-215 (2001).
Galpern, et al., "Xenotransplantation of porcine fetal ventral mesencephalon in rat model of Parkinson's disease: Functional recovery and graft morphology," *Exp. Neurol.* 140:1-13 (1996).
Garcia-Calvo et al., "Inhibition of Human Caspases by Peptide-based and Macromolecular Inhibitors," *J. Biol. Chem.* 273:32608-32613 (1998).
Ghosh and Greenberg, "Distinct Roles for bFGF and NT-3 in the Regulation of Cortical Neurogenesis," *Neuron* 15:89-103 (1995).
Ghosh et al., "Requirement for BDNF in Activity-Dependent Survival of Cortical Neurons," *Science* 263:1618-1623 (1994).
Grados-Munro et al., "Myelin-associated inhibitors of axon regeneration," *J. Neurosci. Res.* 74:479-485 (2003).

(Continued)

*Primary Examiner* — Anne-Marie Falk
(74) *Attorney, Agent, or Firm* — Jones Day

(57) ABSTRACT

The present invention provides a method of differentiating progenitor cells to produce a population containing protected neuronal cells. A method of the invention includes the steps of contacting the progenitor cells with a differentiating agent; and introducing into the progenitor cells a nucleic acid molecule encoding a MEF2 polypeptide or an active fragment thereof, thereby differentiating the progenitor cells to produce a population containing protected neuronal cells. In one embodiment, the MEF2 polypeptide is human MEF2C or an active fragment thereof.

20 Claims, 16 Drawing Sheets

OTHER PUBLICATIONS

Han et al., "Activation of the transcription factor MEF2C by the MAP kinase p38 in inflammation," *Nature* 386:296-299 (1997).

Hanazono et al., "Gene transfer into nonhuman primate hematopoietic stem cells: Implications for gene therapy," *Stem Cells* 19(1):12-23 (2001).

Jackowski, "Neural injury repair: hope for the future as barriers to effective CNS regeneration become clearer," *Brit. J. Neurosurg.* 9(3):303-317 (1995).

Jacks et al., "Effects of an Rb mutation in the mouse," *Nature* 359:295-300 (1992).

Jan and Jan, "HLH proteins, fly neurogenesis, and vertebrate myogenesis," *Cell* 75:827-830 (1993).

Jo et al., "Differential display analysis of gene expression altered by ras oncogene," *Methods Enzymol.* 332:233-244 (2001).

Johe et al., "Single factors direct the differentiation of stem cells from the fetal and adult central nervous system," *Genes Dev.* 10:3129-3140 (1996).

Kato et al., "Bmk1/Erk5 is required for cell proliferation induced by epidermal growth factor," *Nature* 395:713-716 (1998).

Kato et al., "BMK1/ERK5 regulates serum-induced early gene expression through transcription factor MEF2C," *EMBO J.* 16:7054-7066 (1997).

Kaushal et al., "Activation of the myogenic lineage by MEF2A, a factor that induces and cooperates with MyoD," *Science* 266:1236-1240 (1994).

Khanna et al., "Metastasis-associated differences in gene expression in a murine model of osteosarcoma," *Cancer Res.* 61:3750-3759 (2001).

Krainc et al., "Synergistic activation of the N-methyl-D-aspartate receptor subunit 1 promoter by myocyte enhancer factor 2C and Sp1," *J. Biol. Chem.* 273(40):26218-26224 (1998).

Kuida et al., "Decreased apoptosis in the brain and premature lethality in CPP32-deficient mice," *Nature* 384:368-372 (1996).

Lee et al., "Gene expression profile of aging and its retardation by caloric restriction," *Science* 285:1390-1393 (1999).

Lee et al., "Myocyte-specific enhancer factor 2 and thyroid hormone receptor associate and synergistically activate the -cardiac myosin heavy-chain gene," *Mol. Cell. Biol.* 17:2745-2755 (1997).

Lee et al., "Potent and Selective Nonpeptide Inhibitors of Caspases 3 and 7 Inhibit Apoptosis and Maintain Cell Functionality," *J. Biol. Chem.* 275:16007-16014 (2000).

Lee, "Basic helix-loop-helix genes in neural development," *Curr. Opin. Neurobiol.* 7:13-20 (1997).

Leifer et al., "MEF2C, a MADS/MEF2-family transcription factor expressed in a laminar distribution in cerebral cortex," *Proc. Natl. Acad. Sci. U. S. A.* 90:1546-1550 (1993).

Leifer et al., "Myocyte-specific enhancer binding factor 2C expression in human brain development," *Neuroscience* 63:1067-1079 (1994).

Lilly et al., "D-MEF2: a MADS box transcription factor expressed in differentiating mesoderm and muscle cell lineages during *Drosophila* embryogenesis," *Proc. Natl. Acad. Sci. USA* 91:5662-5666 (1994).

Lilly et al., "Requirement of MADS domain transcription factor D-MEF2 for muscle formation in *Drosophila*," *Science* 267:688-693 (1995).

Lin et al., "Control of mouse cardiac morphogenesis and myogenesis by transcription factor MEF2C," *Science* 276:1404-1407 (1997).

Lin et al., "The expression of MEF2 genes is implicated in CNS neuronal differentiation," *Mol. Brain. Res.* 42:307-316 (1996).

Lipton and Rosenberg, "Excitatory Amino Acids as a Final Common Pathway for Neurologic Disorders," *N. Engl. J. Med.* 330(9):613-622 (1994).

Lu et al., "Signal-dependent activation of the MEF2 transcription factor by dissociation from histone deacetylases," *Proc. Natl. Acad. Sci. U. S. A.* 97(8):4070-4075 (2000).

Lyons et al., "Expression of *mef2* genes in the mouse central nervous system suggests a role in neuronal maturation," *J. Neurosci.* 15:5727-5738 (1995).

Mao and Nadal-Ginard, "Functional and physical interactions between mammalian achaete-scute homolog 1 and myocyte enhancer factor 2A," *J. Biol. Chem.* 271:14371-14375 (1996).

Mao et al., "Neuronal Activity-Dependent Cell Survival Mediated by Transcription Factor MEF2," *Science* 286:785-790 (1999).

Martin et al., "A *Mef2* gene that generates a muscle-specific isoform via alternative mRNA splicing," *Mol. Cell. Biol.* 14:1647-1656 (1994).

Martin et al., "Myocyte enhancer factor (MEF) 2C: A tissue-restricted member of the MEF-2 family of transcription factors," *Proc. Natl. Acad. Sci. USA* 90:5282-5286 (1993).

Matsumoto et al., "Platelet-derived growth factor activates p38 mitogen-activated protein kinase through a Ras-dependent pathway that is important for actin reorganization and cell migration," *J. Biol. Chem.* 274:13954-13960 (1999).

McBurney, "P19 embryonal carcinoma cells," *Int. J. Dev. Biol.* 37:135-140 (1993).

McDermott et al., "hMEF2C gene encodes skeletal muscle- and brain-specific transcription factors," *Mol. Cell. Biol.* 13:2564-2577 (1993).

McDonald et al., "Transplanted embryonic stem cells survive, differentiate and promote recovery in injured rat spinal cord," *Nat. Med.* 5:1410-1412 (1999).

Mehler et al., "Progenitor cell biology: Implications for neural regeneration," *Arch. Neurol.* 56:780-784 (1999).

Mezey et al., "Turning Blood into Brain: Cells Bearing Neuronal Antigens Generated in Vivo from Bone Marrow," *Science* 290:1779-1782 (2000).

Milward et al., "Isolation and transplantation of multipotential populations of epidermal growth factor-responsive, neural progenitor cells from the canine brain," *J. Neurosci. Res.* 50:862-871 (1997).

Miraglia et al., "A Novel Five-Transmembrane Hematopoietic Stem Cell Antigen: Isolation, Characterization, and Molecular Cloning," *Blood* 90:5013-5021 (1997).

Miyazono et al., "Proliferation, cell death, and neuronal differentiation in transplanted human embryonal carcinoma (NTera2) cells depend on the graft site in nude and severe combined immunodeficient mice," *Lab. Invest.* (2):273-83 (1995).

Miyoshi et al., "Transduction of Human CD34+ Cells That Mediate Long-Term Engraftment of NOD/SCID Mice by HIV Vectors," *Science* 283:682-686 (1999).

Molkentin et al., "Cooperative activation of muscle gene expression by MEF2 and myogenic bHLH proteins," *Cell* 83:1125-1136 (1995).

Molkentin et al., "MEF2B is a Potent Transactivator Expressed in Early Myogenic Lineages," *Mol. Cell. Biol.* 16:3814-3824 (1996).

Molkentin et al., "Mutational analysis of the DNA binding, dimerization, and transcriptional activation domains of MEF2C," *Mol. Cell. Biol.* 16:2627-2636 (1996).

Mukasa et al., "Wortmannin enhances CPP32-like activity during neuronal differentiation of P19 embryonal carcinoma cells induced by retinoic acid," *Biochem. Biophys. Res. Commun.* 232:192-197 (1997).

Naya and Olson, "MEF2: a transcriptional target for signaling pathways controlling skeletal muscle growth and differentiation," *Curr. Opin. Cell Biol.* 11:683-688 (1999).

New and Han, "The p38 MAP Kinase Pathway and its Biological Function," *Trends Cardiovasc. Med.* 8:220-229 (1998).

Nguyen et al., "D-mef2: a *Drosophila* mesoderm-specific MADS box-containing gene with a biphasic expression profile during embryogenesis," *Proc. Natl. Acad. Sci. USA* 91:7520-7524 (1994).

Nicholson, "From bench to clinic with apoptosis-based therapeutic agents," *Nature* 407:810-816 (2000).

Okamoto et al., "Antiapoptotic role of the p38 mitogen-activated protein kinase-myocyte enhancer factor 2 transcription factor pathway during neuronal differentiation," *Proc. Natl. Acad. Sci., USA* 97:7561-7566 (2000).

Okamoto et al., "Dominant-interfering forms of MEF2 generated by caspase cleavage contribute to NMDA-induced neuronal apoptosis," *Proc. Natl. Acad. Sci. U. S. A.* 99(6):3974-3979 (2002).

Olson et al., "Regulation of muscle differentiation by the MEF2 family of MADS box transcription factors," *Dev. Biol.* 172:2-14 (1995).

Ornatsky et al., "A dominant-negative form of transcription factor MEF2 inhibits myogenesis," *J. Biol. Chem.* 272:33271-33278 (1997).

Pera et al., "Human embryonic stem cells," *J. Cell Science* 113:5-10 (2000).

Pollock and Triesman, "Human SRF-related proteins: DNA-binding properties and potential regulatory targets," *Genes Dev.* 5:2327-2341 (1991).

Reubinoff et al., "Embryonic stem cell lines from human blastocysts: somatic differentiation in vitro," *Nat. Biotechnol.* 18:399-404 (2000).

Ridgeway et al., "Myocyte Enhancer Factor 2C and Myogenin Up-regulate Each Other's Expression and Induce the Development of Skeletal Muscle in P19 Cells," *J. Biol. Chem.* 275: 41-46 (2000).

Robert et al., "Differential display and suppressive subtractive hybridization used to identify granulosa cell messenger RNA associated with bovine oocyte developmental competence," *Biol. Reprod.* 64:1812-1820 (2001).

Rossi and Cattaneo, "Neural stem cell therapy for neurological diseases: dreams and reality," *Nat. Rev. Neurosci.* 3:401-409 (2002).

Skerjanc and Wilton, "Myocyte enhancer factor 2C upregulates MASH-1 expression and induces neurogenesis in P19 cells," *FEBS Letters* 472:53-56 (2000).

Skerjanc et al., "Myocyte enhancer factor 2C and Nkx2-5 up-regulate each other's expression and initiate cardiomyogenesis in P19 cells," *J. Biol. Chem.* 273(52):34904-34910 (1998).

Slack et al., "Cells differentiating into neuroectoderm undergo apoptosis in the absence of functional retinoblastoma family proteins," *J. Cell Biol.* 129:779-788 (1995).

Staege et al., "Two novel genes *FIND* and *LIND* differentially expressed in deactivated and *Listeria*-infected human macrophages," *Immunogenetics* 53:105-113 (2001).

Stemple and Mahanthappa, "Neural stem cells are blasting off," *Neuron* 18:1-4 (1997).

Treisman, "Inside the MADS box," *Nature* 376:468-469 (1995).

Tsunoda et al., "Upregulated expression of angiogenesis genes and down regulation of cell cycle genes in human colorectal cancer tissue determined by cDNA macroarray," *Anticancer Res.* 21:137-143 (2001).

Uchida et al., "Direct isolation of human central nervous system stem cells," *Proc. Natl. Acad. Sci., USA* 97:14720-14725 (2000).

Watson et al., "Phosphorylation of c-Jun is necessary for apoptosis induced by survival signal withdrawal in cerebellar granule neurons," *J. Neurosci.* 18:751-762 (1998).

Williams et al., "A PDGF-Regulated Immediate Early Gene Response Initiates Neuronal Differentiation in Ventricular Zone Progenitor Cells," *Neuron* 18:553-562 (1997).

Wobus et al., "Embryonic Stem Cells and Nuclear Transfer Strategies. Present state and future prospects" *Cells Tissues Organs* 166:1-5 (2000).

Yang et al., "Targeting of p38 mitogen-activated protein kinases to MEF2 transcription factors," *Mol. Cell. Biol.* 19:4028-4038 (1999).

Yin et al., "AC133, a Novel Marker for Human Hematopoietic Stem and Progenitor Cells," *Blood* 90:5002-5012 (1997).

Youn et al., "Apoptosis of T Cells Mediated by $Ca^{2+}$-Induced Release of the Transcription Factor MEF2," *Science* 286:790-793 (1999).

Yu et al., "Human myocyte-specific enhancer factor 2 comprises a group of tissue-restricted MADS box transcription factors," *Genes & Dev.* 6:1783-1798 (1992).

Zhao et al., "Regulation of the MEF2 family of transcription factors by p38," *Mol. Cell. Biol.* 19:21-30 (1999).

Zirlinger et al., "Amygdala-enriched genes identified by microarray technology are restricted to specific amygdaloid subnuclei," *Proc. Natl. Acad. Sci. U. S. A.* 98:5270-5275 (2001).

Zwaka et al., "Homologous recombination in human embryonic stem cells," *Nat. Biotechnol.*, advanced online publication, pp. 1-3 (2003).

GenBank Accession No. NM_005587—*Homo sapiens* MADS box transcription enhancer factor 2, polypeptide A (myocyte enhancer factor 2A) (MEF2A) mRNA. (Nov. 1, 2000).

GenBank Accession No. NM_005919—*Homo sapiens* MADS box transcription enhancer factor 2, polypeptide B (myocyte enhancer factor 2B) (MEF2B) mRNA. (Nov. 1, 2000).

GenBank Accession No. L08895—*Homo sapiens* MADS/MEF2—family transcription factor (MEF2C) mRNA, complete cds. (Jan. 7, 1995).

GenBank Accession No. NM_005920—*Homo sapiens* MADS box transcription enhancer factor 2, polypeptide D (myocyte enhancer factor 2D) (MEF2D) mRNA. (Nov. 1, 2000).

Brundin, P. Et. Al., "Improving the survival of grafted dopaminergic neurons: a review over current approaches," Cell Transplant, 9:179-95 (2000).

* cited by examiner

```
   1 gaattttctg caaggatcat atctaagtgc acttttgct gatacttcat ttctagacat
  61 tgagtctcac tctacccccc aggctgaagt gcagtggtgt gatctcggtt cactgcaacc
 121 tccgcctcca ggttcaagtg attctcgtac ctcagcctcc cgagtagctg ggattacagg
 181 cgcctgccac catgcctggc tgatatttat attttagta gagatggagt ttcaccatgt
 241 tggccaggct ggtctcgaac tctggacctc agatcttgta gaaaatttca gctgtagccc
 301 ttggactaga agctgaaata acagaagctg tgtacgatgc attagggtat tgaagaaaat
 361 taacttttga attaaatatt tggaatataa ggaaataagg aaagttgact gaaaatgggg
 421 cggaagaaaa tacaaatcac acgcataatg gatgaaagga accgacaggt cacttttaca
 481 aagagaaagt ttggattaat gaagaaagcc tatgaactta gtgtgctctg tgactgtgaa
 541 atagcactca tcattttcaa cagctctaac aaactgtttc aatatgctag cactgatatg
 601 gacaaagttc ttctcaagta tacagaatat aatgaacctc atgaaagcag aaccaactcg
 661 gatattgttg aggctctgaa caagaaggaa cacagagggt gcgacagccc agaccctgat
 721 acttcatatg tgctaactcc acatacagaa gaaaaatata aaaaaattaa tgaggaattt
 781 gataatatga tgcggaatca taaaatcgca cctggtctgc cacctcagaa cttttcaatg
 841 tctgtcacag ttccagtgac cagccccaat gctttgtcct acactaaccc agggagttca
 901 ctggtgtccc catctttggc agccagctca acgttaacag attcaagcat gctctctcca
 961 cctcaaacca cattacatag aaatgtgtct cctggagctc ctcagagacc accaagtact
1021 ggcaatgcag gtgggatgtt gagcactaca gacctcacag tgccaaatgg agctggaagc
1081 agtccagtgg ggaatggatt tgtaaactca agagcttctc caaatttgat tggagctact
1141 ggtgcaaata gcttaggcaa agtcatgcct acaaagtctc ccctccacc aggtggtggt
1201 aatcttggaa tgaacagtag gaaaccagat cttcgagttg tcatccccc ttcaagcaag
1261 ggcatgatgc ctccactatc ggaggaagag gaattggagt tgaacaccca aaggatcagt
1321 agttctcaag ccactcaacc tcttgctacc ccagtcgtgt ctgtgacaac cccaagcttg
1381 cctccgcaag gacttgtgta ctcagcaatg ccgactgcct acaacactga ttattcactg
1441 accagcgctg acctgtcagc ccttcaaggc ttcaactcgc aggaatgct gtcgctggga
1501 caggtgtcgg cctggcagca gcaccaccta ggacaagcag ccctcagctc tcttgttgct
1561 ggagggcagt tatctcaggg ttccaattta tccattaata ccaaccaaaa catcagcatc
1621 aagtccgaac cgatttcacc tctcgggat cgtatgaccc catcgggctt ccagcagcag
1681 cagcagcagc agcagcagca gcagccgccg ccaccaccgc agccccagcc acaaccccg
1741 cagccccagc ccgacagga aatggggcgc tccctgtgg acagtctgag cagctctagt
1801 agctcctatg atggcagtga tcgggaggat ccacggggcg acttccattc tccaattgtg
1861 cttggccgac ccccaaaaca tgaggacaga gaaagccctt ctgtaaagcg aatgaggatg
1921 gacgcgtggg tgacctaagg cttccaagct gatgtttgta cttttgtgtt actgcagtga
1981 cctgccctac atatctaaat cggtaaataa ggacatgagt taaatatatt tatatgtaca
2041 tacatatata tatccttta catatatatg tatgtgggtg tgagtgtgtg tgtatgtgtg
2101 ggtgtgtgtt acatacacag aatcaggcac ttacctgcaa actccttgta ggtctgcaga
2161 tgtgtgtccc atggcagaca aagcaccctg taggcacaga caagtctggc acttccttgg
2221 actacttgtt tcgtaaagat aaccagtttt tgcagagaaa cgtgtaccca tatataattc
2281 tcccacacta gcttgcagaa acctagaggg cccctactt gttttattta actgtgcagt
2341 gactgtagtt acttaagaga aaatgctttg tagaacagag cagtagaaaa gcaggaacca
2401 agaaagcaat actgtacata aaatgtcatt tatattttcc aacctggcat gggtgtctgt
2461 tgcaaagggg tgcatgggaa agggctgttg atattaaaaa caaacaaaac aaaaagccc
2521 cacacataac tgttttgcac gtgcaaaaat gtattgggtc aagaagtgat ctttagctaa
2581 taaagaaaga gaatagaaaa cacgcatgag atattcagaa aatactagcc tagaaatata
2641 gagcattaac aaaggaaaat taatatatta agttataatt ggaatatgtc agaagtttct
2701 ttttacattc atatcttaaa aattaaagaa actgatttta gctcatgtat attttatatg
2761 aaagaaaaca cccttatgaa ttgatgacta tatataaaat tatattcact acttttgaac
2821 acattctgct atgaattatt tatataagcc aaagctatat gttgtaactt ttttttagag
2881 aatagcttta tcttggttta actctttagt tttattttaa gaggggaaaa caaaaatatc
2941 ttgcaagcag aaccttgaaa aaaaaaaagg aattc
```

FIG. 2A

```
MGRKKIQITRIMDERNRQVTFTKRKFGLMKKAYELSVLCDCEIALIIFNSSNKLFQYASTDMDKV
LLKYTEYNEPHESRTNSDIVEALNKKEHRGCDSPDPDTSYVLTPHTEEKYKKINEEFDNMMRNHK
IAPGLPPQNFSMSVTVPVTSPNALSYTNPGSSLVSPSLAASSTLTDSSMLSPPQTTLHRNVSPGA
PQRPPSTGNAGGMLSTTDLTVPNGAGSSPVGNGFVNSRASPNLIGATGANSLGKVMPTKSPPPPG
GGNLGMNSRKPDLRVVIPPSSKGMMPPLSEEEELELNTQRISSSQATQPLATPVVSVTTPSLPPQ
GLVYSAMPTAYNTDYSLTSADLSALQGFNSPGMLSLGQVSAWQQHHLGQAALSSLVAGGQLSQGS
NLSINTNQNISIKSEPISPPRDRMTPSGFQQQQQQQQQQQPPPPPQPQPQPPQPQPRQEMGRSPV
DSLSSSSSSYDGSDREDPRGDFHSPIVLGRPPNTEDRESPSVKRMRMDAWVT
```

FIG. 2B

```
   1 cggggtcgc tatggaggag ccggagatgc agctcaaggg gaagaaagtc acggacaagt
  61 tcactgagag cgtctacgtc ctggccaacg agccatccgt ggccctgtac cggctgcagg
 121 agcatgtgcg tcgctccctc cccgagctgg cccagcacaa ggcagacatg cagcgttggg
 181 aggagcagag ccagggagcc atctacactg tggagtacgc ctgcagcgcc gtgaagaacc
 241 tggtggacag cagcgtctac ttccgcagcg tggagggtct gctcaaacag gccatcagca
 301 tccgggacca tatgaatgcc agtgcccagg ccacagccc ggaggaacca ccccgccct
 361 cctcagcctg atcctggaag agactcgggg cccccagcc tccgccaacc agacaaaga
 421 tcattccact cagcctggga cgatggggag gaaaaaaatc cagatctccc gcatcctgga
 481 ccaaaggaat cggcaggtga cgttcaccaa gcggaagttc gggctgatga agaaggccta
 541 tgagctgagc gtgctctgtg actgtgagat agccctcatc atcttcaaca gcgccaaccg
 601 cctcttccag tatgccagca cggacatgga ccgtgtgctg ctgaagtaca cagagtacag
 661 cgagccccac gagagccgca ccaacactga catcctcgag acgctgaagc ggagggcat
 721 tggcctcgat gggccagagc tggagccgga tgaagggcct gaggagccag agagaagtt
 781 tcggaggctg gcaggcgaag ggggtgatcc ggccttgccc cgaccccggc tgtatcctgc
 841 agctcctgct atgcccagcc cagatgtggt atacggggcc ttaccgccac caggctgtga
 901 ccccagtggg cttggggaag cactgcccgc ccagagccgc ccatctccct tccgaccagc
 961 agcccccaaa gccgggcccc caggcctggt gcaccctctc ttctcaccaa gccacctcac
1021 cagcaagaca ccaccccac tgtacctgcc gacggaaggg cggaggtcag acctgcctgg
1081 tggcctggct gggccccgag ggggactaaa cacctccaga agcctctaca gtggcctgca
1141 gaacccctgc tccactgcaa ctcccggacc cccactgggg agcttcccct tcctccccgg
1201 aggccccca gtgggggccg aagcctgggc gaggagggtc ccccaacccg ggcgcctcc
1261 ccgccgaccc ccccagtcag catcaagtct gagcgcctct ctccggcccc cggggcccc
1321 ggcgactttc ctaagacctt ccctatccc ttgctcctcg cccggtccct ggcagagcct
1381 ctgcggcctg ggcccgccct gcgccggctg cccttggccg acggctggcc ccggtaggag
1441 atcacccggt ggcaccagcc cagagcgctc gccaggtacg gcgagggcac gtggggaccc
1501 cacctccctc caggcctctt cagagaagac ccaacagtga cgccccctc cgcggtgggg
1561 gcttggaggt gggcggctgg actcaatcca ccctgggggg ctcctttcct tcttcctatt
1621 tgtgtgtata tccacaaata aaacgcgcgt ggcgtccgtg gaccaaaaaa a
```

FIG. 3A

MGRKKIQISRILDQRNRQVTFTKRKFGLMKKAYELSVLCDCEIALIIFNSANRLFQYASTDMDRV
LLKYTEYSEPHESRTNTDILETLKRRGIGLDGPELEPDEGPEEPGEKFRRLAGEGGDPALPRPRL
YPAAPAMPSPDVVYGALPPPGCDPSGLGEALPAQSRPSPFRPAAPKAGPPGLVHPLFSPSHLTSK
TPPPLYLPTEGRRSDLPGGLAGPRGGLNTSRSLYSGLQNPCSTATPGPPLGSFPFLPGGPPVGAE
AWARRVPQPAAPPRRPPQSASSLSASLRPPGAPATFLRPSPIPCSSPGPWQSLCGLGPPCAGCPW
PTAGPGRRSPGGTSPERSPGTARARGDPTSLQASSEKTQQ

FIG. 3B

```
   1 gaattcccag ctctctgctc gctctgctcg cagtcacaga cacttgagca cacgcgtaca
  61 cccagacatc ttcgggctgc tattggattg actttgaagg ttctgtgtgg gtcgccgtgg
 121 ctgcatgttt gaatcaggtg gagaagcact tcaacgctgg acgaagtaaa gattattgtt
 181 gttattttt ttttctctct ctctctctct taagaaagga aaatatccca aggactaatc
 241 tgatcgggtc ttccttcatc aggaacgaat gcaggaattt gggaactgag ctgtgcaagt
 301 gctgaagaag gagatttgtt tggaggaaac aggaaagaga aagaaaagga aggaaaaaat
 361 acataatttc agggacgaga gagagaagaa aaacggggac tatggggaga aaaaagattc
 421 agattacgag gattatggat gaacgtaaca gacaggtgac atttacaaag aggaaatttg
 481 ggttgatgaa gaaggcttat gagctgagcg tgctgtgtga ctgtgagatt gcgctgatca
 541 tcttcaacag caccaacaag ctgttccagt atgccagcac cgacatggac aaagtgcttc
 601 tcaagtacac ggagtacaac gagccgcatg agagccggac aaactcagac atcgtggaga
 661 cgttgagaaa gaagggcctt aatggctgtg acagcccaga ccccgatgcg gacgattccg
 721 taggtcacag ccctgagtct gaggacaagt acaggaaaat taacgaagat attgatctaa
 781 tgatcagcag gcaaagattg tgtgctgttc cacctcccaa cttcgagatg ccagtctcca
 841 tcccagtgtc cagccacaac agtttggtgt acagcaaccc tgtcagctca ctgggaaacc
 901 ccaacctatt gccactgcct caccctctc tgcagaggaa tagtatgtct cctggtgtaa
 961 cacatcgacc tccaagtgca ggtaacacag gtggtctgat gggtggagac ctcacgtctg
1021 gtgcaggcac cagtgcaggg aacgggtatg gcaatccccg aaactcacca ggtctgctgg
1081 tctcacctgg taacttgaac aagaatatgc aagcaaaatc tcctccccca atgaatttag
1141 gaatgaataa ccgtaaacca gatctccgag ttcttattcc accaggcagc aagaatacga
1201 tgccatcagt gtctgaggat gtcgacctgc ttttgaatca aaggataaat aactcccagt
1261 cggctcagtc attggctacc ccagtggttt ccgtagcaac tcctacttta ccaggacaag
1321 gaatgggagg atatccatca gccatttcaa caacatatgg taccgagtac tctctgagta
1381 gtgcagacct gtcatctctg tctgggttta acaccgccag cgctcttcac cttggttcag
1441 taactggctg gcaacagcaa cacctacata acatgccacc atctgccctc agtcagttgg
1501 gagcttgcac tagcactcat ttatctcaga gttcaaatct ctccctgcct tctactcaaa
1561 gcctcaacat caagtcagaa cctgtttctc ctcctagaga ccgtaccacc accccttcga
1621 gataccccaca acacacgcgc cacgaggcgg ggagatctcc tgttgacagc ttgagcagct
1681 gtagcagttc gtacgacggg agcgaccgag aggatcaccg gaacgaattc cactcccccca
1741 ttggactcac cagaccttcg ccggacgaaa gggaagtcc ctcagtcaag cgcatgcgac
1801 tttctgaagg atgggcaaca tgatcagatt attacttact agttttttt ttttcttgc
1861 agtgtgtgtg tgtgctatac cttaatgggg aagggggtc gatatgcatt atatgtgccg
1921 tgtgtggaaa aaaaaaagt caggtactct gttttgtaaa agtacttta aattgcctca
1981 gtgatacagt ataagataa acagaaatgc tgagataagc ttagcacttg agttgtacaa
2041 cagaacactt gtacaaaata gattttaagg ctaacttctt ttcactgttg tgctcctttg
2101 caaaatgtat gttacaatag atagtgtcat gttgcaggtt caacgttatt tacatgtaaa
2161 tagacaaaag gaaacatttg ccaaaagcgg cagatcttta ctgaaagaga gagcagctgt
2221 tatgcaacat atagaaaaat gtatagatgc ttggacagac ccggtaatgg gtggccattg
2281 gtaaatgtta ggaacacacc aggtcacctg acatcccaga aatgctcaca aacctgcagg
2341 catatcattg gcgtatggca ctcattaaaa aggatcagag accattaaaa gaggaccata
2401 cctattaaaa aaaatgtgg agttggaggg ctaacatatt taattaaata aataaataaa
2461 tctgggtctg catctcttat taaataaaaa tataaaaata tgtacattac attttgctta
2521 ttttcatata aaggtaaga cagagtttgc aaagcatttg tggcttttg tagtttactt
2581 aagccaaaat gtgttttttt cccttgata gcttgctaa tattaaaac agtcctgtaa
2641 aaaaccaaaa aggacttttt gtatagaaag cactaccta gccatgaag aactccatgc
2701 tttgctaacc aagataactg ttttctcttt gtagaagttt tgttttgaa atgtgtattt
2761 ctaattatat aaaatattaa gaatcttta aaaaatctg tgaattaac atgcttgtgt
2821 atagctttct aatatatata atattatggt aatagcagaa gttgttat cttaatagcg
2881 ggaggggggt atatttgtgc agttgcacat ttagtaact atttcttc tgttttcttt
2941 tactctgctt acattttata agtttaaggt cagctgtcaa aaggataacc tgtggggtta
3001 gaacatatca cattgcaaca ccctaaattg ttttaatac attagcaatc tattgggtca
3061 actgacatcc attgtatata ctagtttctt tcatgctatt tttattttgt ttttgcatt
3121 tttatcaaat gcagggcccc ttctgatct caccatttca ccatgcatct tggaattcag
3181 taagtgcata tcctaacttg cccatattct aaatcatctg gttggttttc agcctagaat
3241 ttgatacgct ttttagaaat atgcccagaa tagaaaagct atgttggggc acatgtcctg
```

FIG. 4A

```
3301 caaatatggc cctagaaaca agtgatatgg aatttacttg gtgaataagt tataaattcc
3361 cacagaagaa aaatgtgaaa gactgggtgc tagacaagaa ggaagcaggt aaagggatag
3421 ttgctttgtc atccgttttt aattatttta actgaccctt gacaatcttg tcagcaatat
3481 aggactgttg aacaatcccg gtgtgtcagg accccaaat gtcacttctg cataaagcat
3541 gtatgtcatc tattttttct tcaataaaga gatttaatag ccatttcaag aaatcccata
3601 aagaacctct ctatgtccct ttttttaatt taaaaaaatg actcttgtct aatattcgtc
3661 tataagggat taattttcag acccttaat aagtgagtgc cataagaaag tcaatatata
3721 ttgtttaaaa gatatttcag tctaggaaag attttccttc tcttggaatg tgaagatctg
3781 tcgattcatc tccaatcata tgcattgaca tacacagcaa agaagatata ggcagtaata
3841 tcaacactgc tatatcatgt gtaggacatt tcttatccat tttttctctt ttacttgcat
3901 agttgctatg tgtttctcat tgtaaaaggc tgccgctggg tggcagaagc caagagacct
3961 tattaactag gctatatttt tcttaacttg atctgaaatc cacaattaga ccacaatgca
4021 cctttggttg tatccataaa ggatgctagc ctgccttgta ctaatgtttt atatatt
```

FIG. 4A CONTINUED

MGRKKIQITRIMDERNRQVTFTKRKFGLMKKAYELSVLCDCEIALIIFNSTNKLFQY<u>ASTDMDKV</u>
<u>LLKYTEYNEPHESRTNSDIVETLRKKGLNGCDSPDPDADDSVGHSPESEDKYRKINEDIDLMISR</u>
<u>QRLCAVPPPNFEMPVSIPVSSHNSLVYSNPVSSLGNPNLLPLAHPSLQRNSMSPGVTHRPPSAGN</u>
<u>TGGLMGGDLTSGAGTSAGNGYGNPRNSPGLLVSPGNLNKNMQAKSPPPMNLGMNNRKPDLRVLIP</u>
<u>PGSKNTMPSVSEDVDLLLNQRINNSQSAQSLATPVVSVATPTLPGQGMGGYPSAISTTYGTEYSL</u>
<u>SSADLSSLSGFNTASALHLGSVTGWQQQHLHNMPPSALSQLGACTSTHLSQSSNLSLPSTQSLNI</u>
<u>KSEPVSPPRDRTTTPSRYPQHTRHEAGRSPVDSLSSCSSSYDGSDREDHRNEFHSPIGLTRPSPD</u>
<u>ERESPSVKRMRLSEGWAT</u>

FIG. 4B

```
   1 caggggcgag ggctacccgc tctttgccgt gacaacaccg ttcccccagc cgggctggag
  61 gctgtgcaga aggtatcctg cagaccatga actgagcact gttcccagac cgttcatgag
 121 cacagtgtaa ggtgtgccga gacccaccac ccagcgagcc cctcccctcc gtagcactga
 181 ggaccccgg  agaagatggg gaggaaaaag attcagatcc agcgaatcac cgacgagcgg
 241 aaccgacagg tgactttcac caagcggaag tttggcctga tgaagaaggc gtatgagctg
 301 agcgtgctat gtgactgcga gatcgcactc atcatcttca accactccaa caagctgttc
 361 cagtacgcca gcaccgacat ggacaaggtg ctgctcaagt acacggagta caatgagcca
 421 cacgagagcc gcaccaacgc cgacatcatc gagaccctga ggaagaaggg cttcaatggc
 481 tgcgacagcc ccgagcccga cggggaggac tcgctggaac agagcccct  gctggaggac
 541 aagtaccgac gcgccagcga ggagctcgac gggctcttcc ggcgctatgg gtcaactgtc
 601 ccggccccca actttgccat gcctgtcacg gtgcccgtgt ccaatcagag ctcactgcag
 661 ttcagcaatc ccagcggctc cctggtcacc ccttccctgg tgacatcatc cctcacggac
 721 ccgcggctcc tgtccccca  gcagccagca ctacagagga acagtgtgtc tcctggcctg
 781 ccccagcggc cagctagtgc gggggccatg ctgggggtg  acctgaacag tgctaacgga
 841 gcctgcccca gccctgttgg gaatggctac gtcagtgctc gggcttcccc tggcctcctc
 901 cctgtggcca atggcaacag cctaaacaag gtcatccctg ccaagtctcc gccccacct
 961 acccacagca cccagcttgg agccccagc  cgcaagcccg acctgcgagt catcacttcc
1021 caggcaggaa aggggttaat gcatcacttg actgaggacc atttagatct gaacaatgcc
1081 cagcgccttg gggtctccca gtctactcat tcgctcacca ccccagtggt ttctgtggca
1141 acgccgagtt tactcagcca gggcctcccc ttctcttcca tgcccactgc ctacaacaca
1201 gattaccagt tgaccagtgc agagctctcc tccttaccag cctttagttc acctgggggg
1261 ctgtcgctag gcaatgtcac tgcctggcaa cagccacagc agccccagca gccgcagcag
1321 ccacagcctc cacagcagca gccaccgcag ccacagcagc cacagccaca gcagcctcag
1381 cagccgcaac agccacctca gcaacagtcc cacctggtcc ctgtatctct cagcaacctc
1441 atcccgggca gcccctgcc  ccacgtgggt gctgccctca cagtcaccac ccaccccac
1501 atcagcatca agtcagaacc ggtgtcccca agccgtgagc gcagccctgc gcctccccct
1561 ccagctgtgt tcccagctgc ccgccctgag cctggcgatg gtctcagcag cccagccggg
1621 ggatcctatg agacgggaga ccgggatgac ggacgggggg acttcgggcc cacactgggc
1681 ctgctgcgcc cagcccagag gcctgaggct gagggctcag ctgtgaagag gatgcggctt
1741 gatacctgga cattaaagtg acgattccca ctcccctcct ctcagcctcc ctgatgaaga
1801 gttgacaatc tcaccgcccg cccttccctg ccccgggctc ctcccgctcg accccactt
1861 cctttcttgt gcttcgtgtc ctgttgacgg ttacatttgt gtataattat tatattatt
```

FIG. 5A

```
MGRKKIQIQRITDERNRQVTFTKRKFGLMKKAYELSVLCDCEIALIIFNHSNKLFQYASTDMDKV
LLKYTEYNEPHESRTNADIIETLRKKGFNGCDSPEPDGEDSLEQSPLLEDKYRRASEELDGLFRR
YGSTVPAPNFAMPVTVPVSNQSSLQFSNPSGSLVTPSLVTSSLTDPRLLSPQQPALQRNSVSPGL
PQRPASAGAMLGGDLNSANGACPSPVGNGYVSARASPGLLPVANGNSLNKVIPAKSPPPPTHSTQ
LGAPSRKPDLRVITSQAGKGLMHHLTEDHLDLNNAQRLGVSQSTHSLTTPVVSVATPSLLSQGLP
FSSMPTAYNTDYQLTSAELSSLPAFSSPGGLSLGNVTAWQQPQQPQQPQQPQPPQQQPPQPQQPQ
PQQPQQPQQPPQQQSHLVPVSLSNLIPGSPLPHVGAALTVTTHPHISIKSEPVSPSRERSPAPPP
PAVFPAARPEPGDGLSSPAGGSYETGDRDDGRGDFGPTLGLLRPAPEPEAEGSAVKRMRLDTWTL
K
```

FIG. 5B

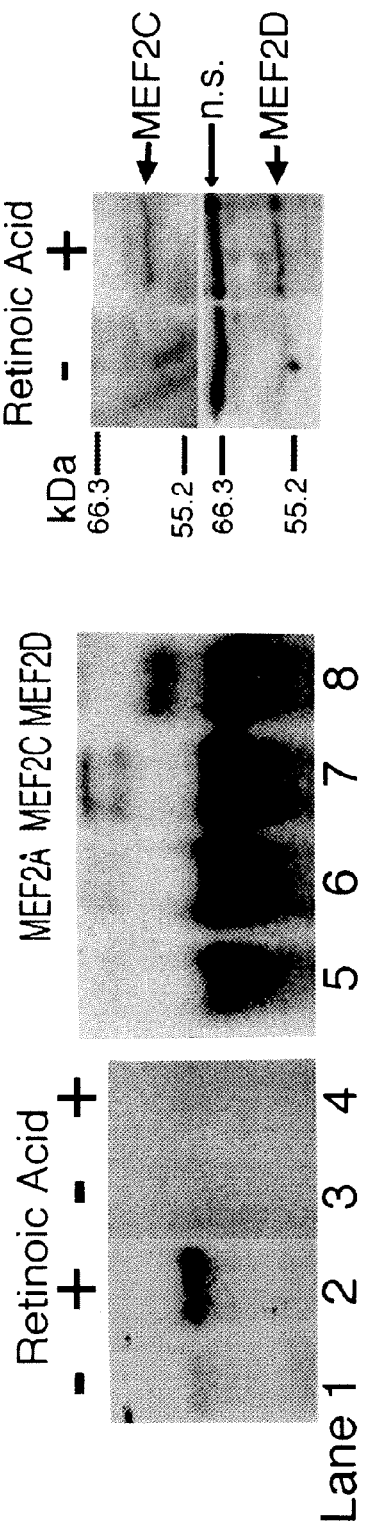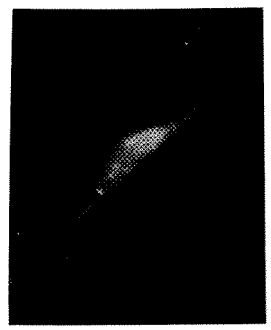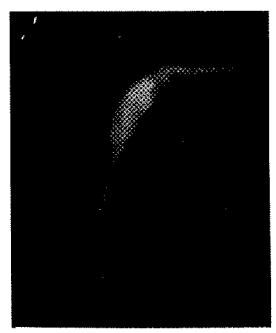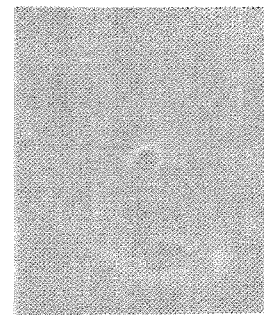

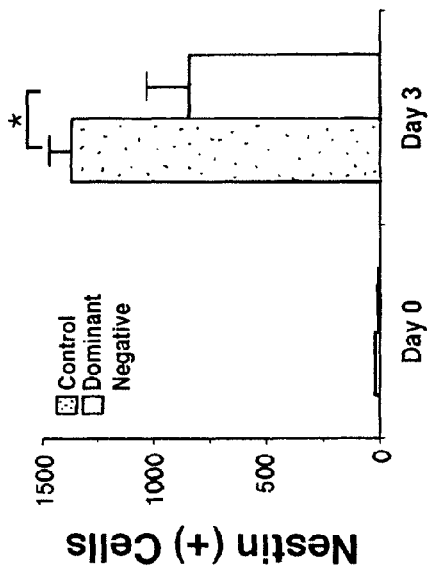
FIG. 8A Nestin (Multipotent Precursor Marker)
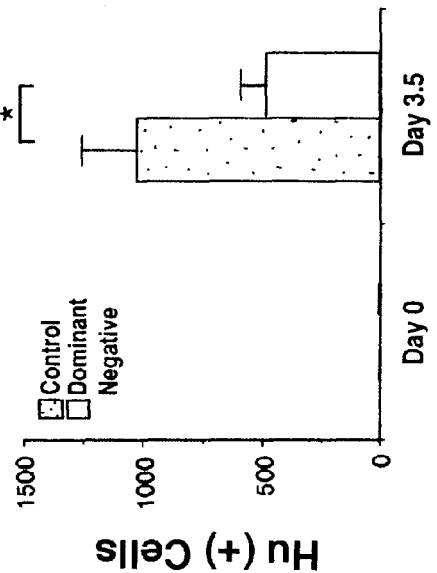
FIG. 8B
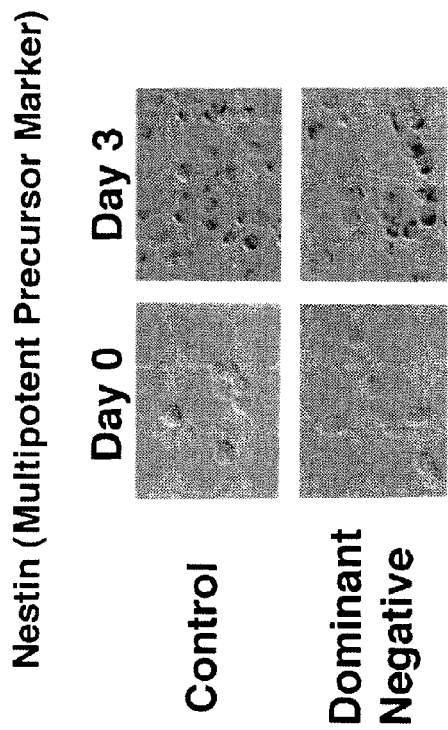
FIG. 8C Hu (Unipotent Precursor Marker)
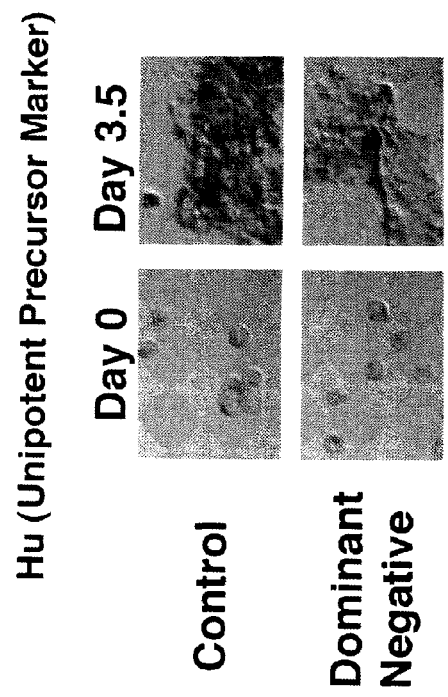
FIG. 8D

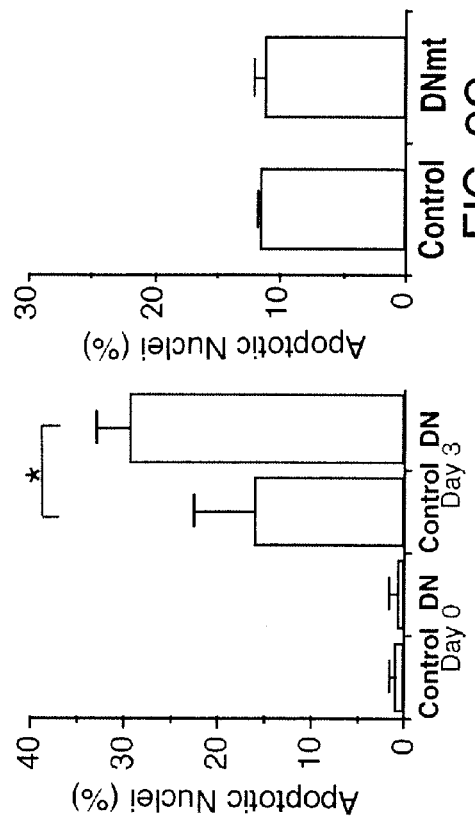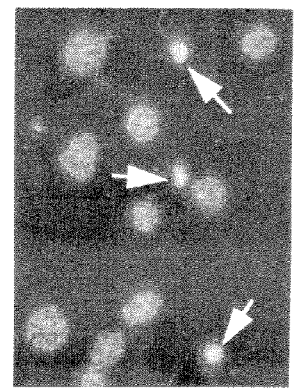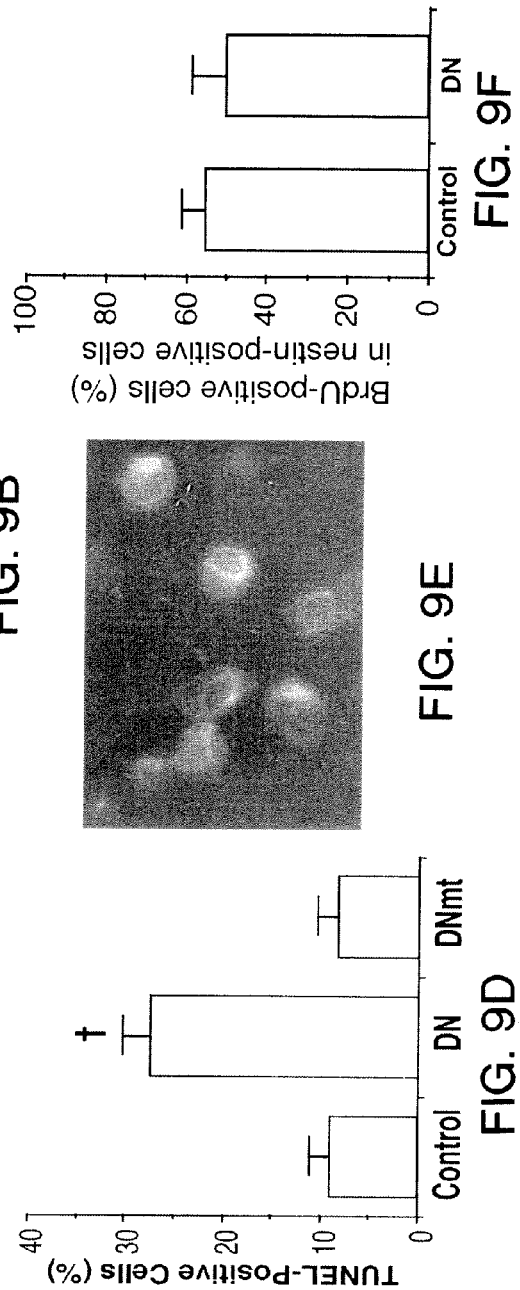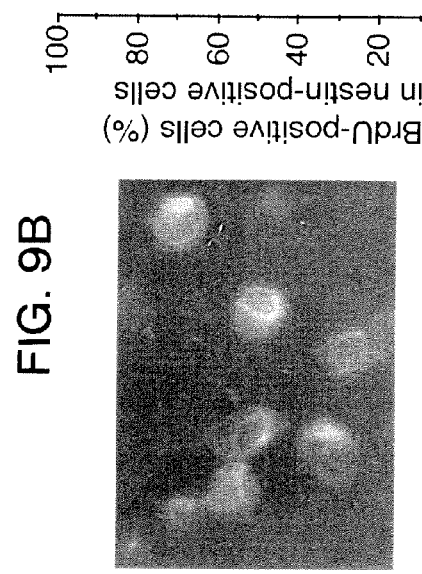
FIG. 9A
FIG. 9B
FIG. 9C
FIG. 9D
FIG. 9E
FIG. 9F

SEQUENCE LISTING

```
<160> NUMBER OF SEQ ID NOS: 25

<210> SEQ ID NO 1
<211> LENGTH: 2975
<212> TYPE: DNA
<213> ORGANISM: Homo sapiens
<220> FEATURE:
<221> NAME/KEY: CDS
<222> LOCATION: (415)...(1935)

<400> SEQUENCE: 1
gaattttctg caaggatcat atctaagtgc acttttttgct gatacttcat ttctagacat      60
tgagtctcac tctaccccccc aggctgaagt gcagtggtgt gatctcggtt cactgcaacc     120
tccgcctcca ggttcaagtg attctcgtac ctcagcctcc cgagtagctg ggattacagg     180
cgcctgccac catgcctggc tgatatttat attttttagta gagatggagt ttcaccatgt     240
tggccaggct ggtctcgaac tctggacctc agatcttgta gaaaatttca gctgtagccc     300
ttggactaga agctgaaata acagaagctg tgtacgatgc attagggtat tgaagaaaat     360 taactttttga attaaatatt tggaatataa ggaaataagg aaagttgact gaaa atg      417
                                                                   Met
                                                                   1 ggg cgg aag aaa ata caa atc aca cgc ata atg gat gaa agg aac cga       465
Gly Arg Lys Lys Ile Gln Ile Thr Arg Ile Met Asp Glu Arg Asn Arg
            5                  10                  15 cag gtc act ttt aca aag aga aag ttt gga tta atg aag aaa gcc tat       513
Gln Val Thr Phe Thr Lys Arg Lys Phe Gly Leu Met Lys Lys Ala Tyr
        20                  25                  30 gaa ctt agt gtg ctc tgt gac tgt gaa ata gca ctc atc att ttc aac       561
Glu Leu Ser Val Leu Cys Asp Cys Glu Ile Ala Leu Ile Ile Phe Asn
    35                  40                  45 agc tct aac aaa ctg ttt caa tat gct agc act gat atg gac aaa gtt       609
Ser Ser Asn Lys Leu Phe Gln Tyr Ala Ser Thr Asp Met Asp Lys Val
50                  55                  60                  65 ctt ctc aag tat aca gaa tat aat gaa cct cat gaa agc aga acc aac       657
Leu Leu Lys Tyr Thr Glu Tyr Asn Glu Pro His Glu Ser Arg Thr Asn
                70                  75                  80 tcg gat att gtt gag gct ctg aac aag aag gaa cac aga ggg tgc gac       705
Ser Asp Ile Val Glu Ala Leu Asn Lys Lys Glu His Arg Gly Cys Asp
            85                  90                  95 agc cca gac cct gat act tca tat gtg cta act cca cat aca gaa gaa       753
Ser Pro Asp Pro Asp Thr Ser Tyr Val Leu Thr Pro His Thr Glu Glu
```

-continued

```
                100                 105                 110
aaa tat aaa aaa att aat gag gaa ttt gat aat atg atg cgg aat cat       801
Lys Tyr Lys Lys Ile Asn Glu Glu Phe Asp Asn Met Met Arg Asn His
    115                 120                 125 aaa atc gca cct ggt ctg cca cct cag aac ttt tca atg tct gtc aca       849
Lys Ile Ala Pro Gly Leu Pro Pro Gln Asn Phe Ser Met Ser Val Thr
130                 135                 140                 145 gtt cca gtg acc agc ccc aat gct ttg tcc tac act aac cca ggg agt       897
Val Pro Val Thr Ser Pro Asn Ala Leu Ser Tyr Thr Asn Pro Gly Ser
                150                 155                 160 tca ctg gtg tcc cca tct ttg gca gcc agc tca acg tta aca gat tca       945
Ser Leu Val Ser Pro Ser Leu Ala Ala Ser Ser Thr Leu Thr Asp Ser
            165                 170                 175 agc atg ctc tct cca cct caa acc aca tta cat aga aat gtg tct cct       993
Ser Met Leu Ser Pro Pro Gln Thr Thr Leu His Arg Asn Val Ser Pro
        180                 185                 190 gga gct cct cag aga cca cca agt act ggc aat gca ggt ggg atg ttg      1041
Gly Ala Pro Gln Arg Pro Pro Ser Thr Gly Asn Ala Gly Gly Met Leu
    195                 200                 205 agc act aca gac ctc aca gtg cca aat gga gct gga agc agt cca gtg      1089
Ser Thr Thr Asp Leu Thr Val Pro Asn Gly Ala Gly Ser Ser Pro Val
210                 215                 220                 225 ggg aat gga ttt gta aac tca aga gct tct cca aat ttg att gga gct      1137
Gly Asn Gly Phe Val Asn Ser Arg Ala Ser Pro Asn Leu Ile Gly Ala
                230                 235                 240 act ggt gca aat agc tta ggc aaa gtc atg cct aca aag tct ccc cct      1185
Thr Gly Ala Asn Ser Leu Gly Lys Val Met Pro Thr Lys Ser Pro Pro
            245                 250                 255 cca cca ggt ggt ggt aat ctt gga atg aac agt agg aaa cca gat ctt      1233
Pro Pro Gly Gly Gly Asn Leu Gly Met Asn Ser Arg Lys Pro Asp Leu
        260                 265                 270 cga gtt gtc atc ccc cct tca agc aag ggc atg atg cct cca cta tcg      1281
Arg Val Val Ile Pro Pro Ser Ser Lys Gly Met Met Pro Pro Leu Ser
    275                 280                 285 gag gaa gag gaa ttg gag ttg aac acc caa agg atc agt agt tct caa      1329
Glu Glu Glu Glu Leu Glu Leu Asn Thr Gln Arg Ile Ser Ser Ser Gln
290                 295                 300                 305 gcc act caa cct ctt gct acc cca gtc gtg tct gtg aca acc cca agc      1377
Ala Thr Gln Pro Leu Ala Thr Pro Val Val Ser Val Thr Thr Pro Ser
                310                 315                 320 ttg cct ccg caa gga ctt gtg tac tca gca atg ccg act gcc tac aac      1425
Leu Pro Pro Gln Gly Leu Val Tyr Ser Ala Met Pro Thr Ala Tyr Asn
            325                 330                 335 act gat tat tca ctg acc agc gct gac ctg tca gcc ctt caa ggc ttc      1473
Thr Asp Tyr Ser Leu Thr Ser Ala Asp Leu Ser Ala Leu Gln Gly Phe
        340                 345                 350 aac tcg cca gga atg ctg tcg ctg gga cag gtg tcg gcc tgg cag cag      1521
Asn Ser Pro Gly Met Leu Ser Leu Gly Gln Val Ser Ala Trp Gln Gln
    355                 360                 365 cac cac cta gga caa gca gcc ctc agc tct ctt gtt gct gga ggg cag      1569
His His Leu Gly Gln Ala Ala Leu Ser Ser Leu Val Ala Gly Gly Gln
370                 375                 380                 385 tta tct cag ggt tcc aat tta tcc att aat acc aac caa aac atc agc      1617
Leu Ser Gln Gly Ser Asn Leu Ser Ile Asn Thr Asn Gln Asn Ile Ser
                390                 395                 400 atc aag tcc gaa ccg att tca cct cct cgg gat cgt atg acc cca tcg      1665
Ile Lys Ser Glu Pro Ile Ser Pro Pro Arg Asp Arg Met Thr Pro Ser
            405                 410                 415 ggc ttc cag cag cag cag cag cag cag cag cag cag ccg ccg cca         1713
Gly Phe Gln Gln Gln Gln Gln Gln Gln Gln Gln Gln Pro Pro Pro
```

-continued

```
                 420             425             430
cca ccg cag ccc cag cca caa ccc ccg cag ccc cag ccc cga cag gaa    1761
Pro Pro Gln Pro Gln Pro Gln Pro Pro Gln Pro Gln Pro Arg Gln Glu
        435                 440                 445 atg ggg cgc tcc cct gtg gac agt ctg agc agc tct agt agc tcc tat    1809
Met Gly Arg Ser Pro Val Asp Ser Leu Ser Ser Ser Ser Ser Ser Tyr
450                 455                 460                 465 gat ggc agt gat cgg gag gat cca cgg ggc gac ttc cat tct cca att    1857
Asp Gly Ser Asp Arg Glu Asp Pro Arg Gly Asp Phe His Ser Pro Ile
                470                 475                 480 gtg ctt ggc cga ccc cca aac act gag gac aga gaa agc cct tct gta    1905
Val Leu Gly Arg Pro Pro Asn Thr Glu Asp Arg Glu Ser Pro Ser Val
            485                 490                 495 aag cga atg agg atg gac gcg tgg gtg acc taaggcttcc aagctgatgt      1955
Lys Arg Met Arg Met Asp Ala Trp Val Thr
        500                 505 ttgtacttt gtgttactgc agtgacctgc cctacatatc taaatcggta aataaggaca   2015
tgagttaaat atatttatat gtacatacat atatatatcc ctttacatat atatgtatgt  2075
gggtgtgagt gtgtgtgtat gtgtgggtgt gtgttacata cacagaatca ggcacttacc  2135
tgcaaactcc ttgtaggtct gcagatgtgt gtcccatggc agacaaagca ccctgtaggc  2195
acagacaagt ctggcacttc cttggactac ttgtttcgta aagataacca gttttttgcag 2255
agaaacgtgt acccatatat aattctccca cactagcttg cagaaaccta gagggccccc  2315
tacttgtttt atttaactgt gcagtgactg tagttactta agagaaaatg ctttgtagaa  2375
cagagcagta gaaaagcagg aaccaagaaa gcaatactgt acataaaatg tcatttatat  2435
tttccaacct ggcatgggtg tctgttgcaa aggggtgcat gggaaagggc tgttgatatt  2495
aaaaacaaac aaaacaaaaa agccccacac ataactgttt tgcacgtgca aaatgtatt   2555
gggtcaagaa gtgatcttta gctaataaag aaagagaata gaaaacacgc atgagatatt  2615
cagaaaatac tagcctagaa atatagagca ttaacaaagg aaaattaata tattaagtta  2675
taattggaat atgtcagaag tttcttttta cattcatatc ttaaaaatta agaaactga   2735
ttttagctca tgtatatttt atatgaaaga aaacacccctt atgaattgat gactatatat  2795
aaaattatat tcactacttt tgaacacatt ctgctatgaa ttatttatat aagccaaagc  2855
tatatgttgt aacttttttt tagagaatag ctttatcttg gttaactct ttagttttat   2915
tttaagaggg gaaaacaaaa atatcttgca agcagaacct tgaaaaaaaa aaggaattc   2975
```

```
<210> SEQ ID NO 2
<211> LENGTH: 507
<212> TYPE: PRT
<213> ORGANISM: Homo sapiens

<400> SEQUENCE: 2

Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Lys Glu His Arg Gly Cys
```

```
                    85                  90                  95
Asp Ser Pro Asp Pro Asp Thr Ser Tyr Val Leu Thr Pro His Thr Glu
                100                 105                 110
Glu Lys Tyr Lys Lys Ile Asn Glu Glu Phe Asp Asn Met Met Arg Asn
                115                 120                 125
His Lys Ile Ala Pro Gly Leu Pro Gln Asn Phe Ser Met Ser Val
        130                 135                 140
Thr Val Pro Val Thr Ser Pro Asn Ala Leu Ser Tyr Thr Asn Pro Gly
145                 150                 155                 160
Ser Ser Leu Val Ser Pro Ser Leu Ala Ala Ser Ser Thr Leu Thr Asp
                165                 170                 175
Ser Ser Met Leu Ser Pro Pro Gln Thr Thr Leu His Arg Asn Val Ser
                180                 185                 190
Pro Gly Ala Pro Gln Arg Pro Pro Ser Thr Gly Asn Ala Gly Gly Met
                195                 200                 205
Leu Ser Thr Thr Asp Leu Thr Val Pro Asn Gly Ala Gly Ser Ser Pro
                210                 215                 220
Val Gly Asn Gly Phe Val Asn Ser Arg Ala Ser Pro Asn Leu Ile Gly
225                 230                 235                 240
Ala Thr Gly Ala Asn Ser Leu Gly Lys Val Met Pro Thr Lys Ser Pro
                245                 250                 255
Pro Pro Pro Gly Gly Asn Leu Gly Met Asn Ser Arg Lys Pro Asp
                260                 265                 270
Leu Arg Val Val Ile Pro Pro Ser Ser Lys Gly Met Met Pro Pro Leu
                275                 280                 285
Ser Glu Glu Glu Glu Leu Glu Leu Asn Thr Gln Arg Ile Ser Ser Ser
                290                 295                 300
Gln Ala Thr Gln Pro Leu Ala Thr Pro Val Val Ser Val Thr Thr Pro
305                 310                 315                 320
Ser Leu Pro Pro Gln Gly Leu Val Tyr Ser Ala Met Pro Thr Ala Tyr
                325                 330                 335
Asn Thr Asp Tyr Ser Leu Thr Ser Ala Asp Leu Ser Ala Leu Gln Gly
                340                 345                 350
Phe Asn Ser Pro Gly Met Leu Ser Leu Gly Gln Val Ser Ala Trp Gln
                355                 360                 365
Gln His His Leu Gly Gln Ala Ala Leu Ser Ser Leu Val Ala Gly Gly
                370                 375                 380
Gln Leu Ser Gln Gly Ser Asn Leu Ser Ile Asn Thr Asn Gln Asn Ile
385                 390                 395                 400
Ser Ile Lys Ser Glu Pro Ile Ser Pro Pro Arg Asp Arg Met Thr Pro
                405                 410                 415
Ser Gly Phe Gln Gln Gln Gln Gln Gln Gln Gln Gln Gln Gln Pro Pro
                420                 425                 430
Pro Pro Pro Gln Pro Gln Pro Gln Pro Gln Pro Gln Pro Arg Gln
                435                 440                 445
Glu Met Gly Arg Ser Pro Val Asp Ser Leu Ser Ser Ser Ser Ser
        450                 455                 460
Tyr Asp Gly Ser Asp Arg Glu Asp Pro Arg Gly Asp Phe His Ser Pro
465                 470                 475                 480
Ile Val Leu Gly Arg Pro Pro Asn Thr Glu Asp Arg Glu Ser Pro Ser
                485                 490                 495
Val Lys Arg Met Arg Met Asp Ala Trp Val Thr
        500                 505
```

```
<210> SEQ ID NO 3
<211> LENGTH: 1671
<212> TYPE: DNA
<213> ORGANISM: Homo sapiens
<220> FEATURE:
<221> NAME/KEY: CDS
<222> LOCATION: (443)...(1537)

<400> SEQUENCE: 3
cgggggtcgc tatggaggag ccggagatgc agctcaaggg gaagaaagtc acggacaagt      60
tcactgagag cgtctacgtc ctggccaacg agccatccgt ggccctgtac cggctgcagg     120
agcatgtgcg tcgctccctc cccgagctgg cccagcacaa ggcagacatg cagcgttggg     180
aggagcagag ccagggagcc atctacactg tggagtacgc ctgcagcgcc gtgaagaacc     240
tggtggacag cagcgtctac ttccgcagcg tggagggtct gctcaaacag gccatcagca     300
tccgggacca tatgaatgcc agtgcccagg ccacagcccc ggaggaacca ccccgccct      360 cctcagcctg atcctggaag agactcgggg ccccccagcc tccgccaacc cagacaaaga     420
tcattccact cagcctggga cg atg ggg agg aaa aaa atc cag atc tcc cgc      472
                         Met Gly Arg Lys Lys Ile Gln Ile Ser Arg
                           1               5                  10 atc ctg gac caa agg aat cgg cag gtg acg ttc acc aag cgg aag ttc       520
Ile Leu Asp Gln Arg Asn Arg Gln Val Thr Phe Thr Lys Arg Lys Phe
                15                  20                  25 ggg ctg atg aag aag gcc tat gag ctg agc gtg ctc tgt gac tgt gag       568
Gly Leu Met Lys Lys Ala Tyr Glu Leu Ser Val Leu Cys Asp Cys Glu
        30                  35                  40 ata gcc ctc atc atc ttc aac agc gcc aac cgc ctc ttc cag tat gcc       616
Ile Ala Leu Ile Ile Phe Asn Ser Ala Asn Arg Leu Phe Gln Tyr Ala
    45                  50                  55 agc acg gac atg gac cgt gtg ctg ctg aag tac aca gag tac agc gag       664
Ser Thr Asp Met Asp Arg Val Leu Leu Lys Tyr Thr Glu Tyr Ser Glu
60                  65                  70 ccc cac gag agc cgc acc aac act gac atc ctc gag acg ctg aag cgg       712
Pro His Glu Ser Arg Thr Asn Thr Asp Ile Leu Glu Thr Leu Lys Arg
            75                  80                  85                  90 agg ggc att ggc ctc gat ggg cca gag ctg gag ccg gat gaa ggg cct       760
Arg Gly Ile Gly Leu Asp Gly Pro Glu Leu Glu Pro Asp Glu Gly Pro
                95                 100                 105 gag gag cca gga gag aag ttt cgg agg ctg gca ggc gaa ggg ggt gat       808
Glu Glu Pro Gly Glu Lys Phe Arg Arg Leu Ala Gly Glu Gly Gly Asp
        110                 115                 120 ccg gcc ttg ccc cga ccc cgg ctg tat cct gca gct cct gct atg ccc       856
Pro Ala Leu Pro Arg Pro Arg Leu Tyr Pro Ala Ala Pro Ala Met Pro
    125                 130                 135 agc cca gat gtg gta tac ggg gcc tta ccg cca cca ggc tgt gac ccc       904
Ser Pro Asp Val Val Tyr Gly Ala Leu Pro Pro Pro Gly Cys Asp Pro
140                 145                 150 agt ggg ctt ggg gaa gca ctg ccc gcc cag agc cgc cca tct ccc ttc       952
Ser Gly Leu Gly Glu Ala Leu Pro Ala Gln Ser Arg Pro Ser Pro Phe
155                 160                 165                 170 cga cca gca gcc ccc aaa gcc ggg ccc cca ggc ctg gtg cac cct ctc      1000
Arg Pro Ala Ala Pro Lys Ala Gly Pro Pro Gly Leu Val His Pro Leu
                175                 180                 185 ttc tca cca agc cac ctc acc agc aag aca cca ccc cca ctg tac ctg      1048
Phe Ser Pro Ser His Leu Thr Ser Lys Thr Pro Pro Pro Leu Tyr Leu
            190                 195                 200 ccg acg gaa ggg cgg agg tca gac ctg cct ggt ggc ctg gct ggg ccc      1096
Pro Thr Glu Gly Arg Arg Ser Asp Leu Pro Gly Gly Leu Ala Gly Pro
        205                 210                 215
```

```
cga ggg gga cta aac acc tcc aga agc ctc tac agt ggc ctg cag aac    1144
Arg Gly Gly Leu Asn Thr Ser Arg Ser Leu Tyr Ser Gly Leu Gln Asn
    220                 225                 230 ccc tgc tcc act gca act ccc gga ccc cca ctg ggg agc ttc ccc ttc    1192
Pro Cys Ser Thr Ala Thr Pro Gly Pro Pro Leu Gly Ser Phe Pro Phe
235                 240                 245                 250 ctc ccc gga ggc ccc cca gtg ggg gcc gaa gcc tgg gcg agg agg gtc    1240
Leu Pro Gly Gly Pro Pro Val Gly Ala Glu Ala Trp Ala Arg Arg Val
                255                 260                 265 ccc caa ccc gcg gcg cct ccc cgc cga ccc ccc cag tca gca tca agt    1288
Pro Gln Pro Ala Ala Pro Pro Arg Arg Pro Pro Gln Ser Ala Ser Ser
            270                 275                 280 ctg agc gcc tct ctc cgg ccc ccg ggg gcc ccg gcg act ttc cta aga    1336
Leu Ser Ala Ser Leu Arg Pro Pro Gly Ala Pro Ala Thr Phe Leu Arg
        285                 290                 295 cct tcc cct atc cct tgc tcc tcg ccc ggt ccc tgg cag agc ctc tgc    1384
Pro Ser Pro Ile Pro Cys Ser Ser Pro Gly Pro Trp Gln Ser Leu Cys
    300                 305                 310 ggc ctg ggc ccg ccc tgc gcc ggc tgc cct tgg ccg acg gct ggc ccc    1432
Gly Leu Gly Pro Pro Cys Ala Gly Cys Pro Trp Pro Thr Ala Gly Pro
315                 320                 325                 330 ggt agg aga tca ccc ggt ggc acc agc cca gag cgc tcg cca ggt acg    1480
Gly Arg Arg Ser Pro Gly Gly Thr Ser Pro Glu Arg Ser Pro Gly Thr
                335                 340                 345 gcg agg gca cgt ggg gac ccc acc tcc ctc cag gcc tct tca gag aag    1528
Ala Arg Ala Arg Gly Asp Pro Thr Ser Leu Gln Ala Ser Ser Glu Lys
            350                 355                 360 acc caa cag tgacgccccc ctccgcggtg ggggcttgga ggtgggcggc            1577
Thr Gln Gln
        365 tggactcaat ccaccctggg gggctccttt ccttcttcct atttgtgtgt atatccacaa  1637 ataaaacgcg cgtggcgtcc gtggaccaaa aaaa                              1671

<210> SEQ ID NO 4
<211> LENGTH: 365
<212> TYPE: PRT
<213> ORGANISM: Homo sapiens

<400> SEQUENCE: 4

Met Gly Arg Lys Lys Ile Gln Ile Ser Arg Ile Leu Asp Gln Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Ala Asn Arg Leu Phe Gln Tyr Ala Ser Thr Asp Met Asp Arg
    50                  55                  60

Val Leu Leu Lys Tyr Thr Glu Tyr Ser Glu Pro His Glu Ser Arg Thr
65                  70                  75                  80

Asn Thr Asp Ile Leu Glu Thr Leu Lys Arg Arg Gly Ile Gly Leu Asp
            85                  90                  95

Gly Pro Glu Leu Glu Pro Asp Glu Gly Pro Glu Glu Pro Gly Glu Lys
        100                 105                 110

Phe Arg Arg Leu Ala Gly Glu Gly Gly Asp Pro Ala Leu Pro Arg Pro
    115                 120                 125

Arg Leu Tyr Pro Ala Ala Pro Ala Met Pro Ser Pro Asp Val Val Tyr
130                 135                 140
```

-continued

```
Gly Ala Leu Pro Pro Pro Gly Cys Asp Pro Ser Gly Leu Gly Glu Ala
145                 150                 155                 160

Leu Pro Ala Gln Ser Arg Pro Ser Pro Phe Arg Pro Ala Ala Pro Lys
                165                 170                 175

Ala Gly Pro Pro Gly Leu Val His Pro Leu Phe Ser Pro Ser His Leu
            180                 185                 190

Thr Ser Lys Thr Pro Pro Leu Tyr Leu Pro Thr Glu Gly Arg Arg
        195                 200                 205

Ser Asp Leu Pro Gly Gly Leu Ala Gly Pro Arg Gly Gly Leu Asn Thr
    210                 215                 220

Ser Arg Ser Leu Tyr Ser Gly Leu Gln Asn Pro Cys Ser Thr Ala Thr
225                 230                 235                 240

Pro Gly Pro Pro Leu Gly Ser Phe Pro Phe Leu Pro Gly Gly Pro Pro
                245                 250                 255

Val Gly Ala Glu Ala Trp Ala Arg Arg Val Pro Gln Pro Ala Ala Pro
            260                 265                 270

Pro Arg Arg Pro Pro Gln Ser Ala Ser Ser Leu Ser Ala Ser Leu Arg
        275                 280                 285

Pro Pro Gly Ala Pro Ala Thr Phe Leu Arg Pro Ser Pro Ile Pro Cys
    290                 295                 300

Ser Ser Pro Gly Pro Trp Gln Ser Leu Cys Gly Leu Gly Pro Pro Cys
305                 310                 315                 320

Ala Gly Cys Pro Trp Pro Thr Ala Gly Pro Gly Arg Arg Ser Pro Gly
                325                 330                 335

Gly Thr Ser Pro Glu Arg Ser Pro Gly Thr Ala Arg Ala Arg Gly Asp
            340                 345                 350

Pro Thr Ser Leu Gln Ala Ser Ser Glu Lys Thr Gln Gln
        355                 360                 365

<210> SEQ ID NO 5
<211> LENGTH: 4077
<212> TYPE: DNA
<213> ORGANISM: Homo sapiens
<220> FEATURE:
<221> NAME/KEY: CDS
<222> LOCATION: (402)...(1820)

<400> SEQUENCE: 5
gaattcccag ctctctgctc gctctgctcg cagtcacaga cacttgagca cacgcgtaca      60
cccagacatc ttcgggctgc tattggattg actttgaagg ttctgtgtgg gtcgccgtgg     120
ctgcatgttt gaatcaggtg gagaagcact tcaacgctgg acgaagtaaa gattattgtt     180 gttattttt ttttctctct ctctctctct taagaaagga aaatatccca aggactaatc      240
tgatcgggtc ttccttcatc aggaacgaat gcaggaattt gggaactgag ctgtgcaagt     300
gctgaagaag gagatttgtt tggaggaaac aggaaagaga agaaaaggaa ggaaaaaat      360 acataatttc agggacgaga gagagaagaa aaacggggac t atg ggg aga aaa aag     416
                                              Met Gly Arg Lys Lys
                                                1               5 att cag att acg agg att atg gat gaa cgt aac aga cag gtg aca ttt       464
Ile Gln Ile Thr Arg Ile Met Asp Glu Arg Asn Arg Gln Val Thr Phe
            10                  15                  20 aca aag agg aaa ttt ggg ttg atg aag aag gct tat gag ctg agc gtg       512
Thr Lys Arg Lys Phe Gly Leu Met Lys Lys Ala Tyr Glu Leu Ser Val
        25                  30                  35 ctg tgt gac tgt gag att gcg ctg atc atc ttc aac agc acc aac aag       560
Leu Cys Asp Cys Glu Ile Ala Leu Ile Ile Phe Asn Ser Thr Asn Lys
    40                  45                  50
```

| | | |
|---|---|---|
| ctg ttc cag tat gcc agc acc gac atg gac aaa gtg ctt ctc aag tac<br>Leu Phe Gln Tyr Ala Ser Thr Asp Met Asp Lys Val Leu Leu Lys Tyr<br>55                            60                        65 | | 608 |
| acg gag tac aac gag ccg cat gag agc cgg aca aac tca gac atc gtg<br>Thr Glu Tyr Asn Glu Pro His Glu Ser Arg Thr Asn Ser Asp Ile Val<br>70                       75                        80                       85 | | 656 |
| gag acg ttg aga aag aag ggc ctt aat ggc tgt gac agc cca gac ccc<br>Glu Thr Leu Arg Lys Lys Gly Leu Asn Gly Cys Asp Ser Pro Asp Pro<br>                   90                       95                        100 | | 704 |
| gat gcg gac gat tcc gta ggt cac agc cct gag tct gag gac aag tac<br>Asp Ala Asp Asp Ser Val Gly His Ser Pro Glu Ser Glu Asp Lys Tyr<br>                  105                          110                       115 | | 752 |
| agg aaa att aac gaa gat att gat cta atg atc agc agg caa aga ttg<br>Arg Lys Ile Asn Glu Asp Ile Asp Leu Met Ile Ser Arg Gln Arg Leu<br>120                         125                        130 | | 800 |
| tgt gct gtt cca cct ccc aac ttc gag atg cca gtc tcc atc cca gtg<br>Cys Ala Val Pro Pro Pro Asn Phe Glu Met Pro Val Ser Ile Pro Val<br>135                         140                       145 | | 848 |
| tcc agc cac aac agt ttg gtg tac agc aac cct gtc agc tca ctg gga<br>Ser Ser His Asn Ser Leu Val Tyr Ser Asn Pro Val Ser Ser Leu Gly<br>150                         155                        160                       165 | | 896 |
| aac ccc aac cta ttg cca ctg gct cac cct tct ctg cag agg aat agt<br>Asn Pro Asn Leu Leu Pro Leu Ala His Pro Ser Leu Gln Arg Asn Ser<br>                  170                          175                       180 | | 944 |
| atg tct cct ggt gta aca cat cga cct cca agt gca ggt aac aca ggt<br>Met Ser Pro Gly Val Thr His Arg Pro Pro Ser Ala Gly Asn Thr Gly<br>                        185                          190                       195 | | 992 |
| ggt ctg atg ggt gga gac ctc acg tct ggt gca ggc acc agt gca ggg<br>Gly Leu Met Gly Gly Asp Leu Thr Ser Gly Ala Gly Thr Ser Ala Gly<br>                200                        205                       210 | | 1040 |
| aac ggg tat ggc aat ccc cga aac tca cca ggt ctg ctg gtc tca cct<br>Asn Gly Tyr Gly Asn Pro Arg Asn Ser Pro Gly Leu Leu Val Ser Pro<br>215                         220                       225 | | 1088 |
| ggt aac ttg aac aag aat atg caa gca aaa tct cct ccc cca atg aat<br>Gly Asn Leu Asn Lys Asn Met Gln Ala Lys Ser Pro Pro Pro Met Asn<br>230                         235                        240                       245 | | 1136 |
| tta gga atg aat aac cgt aaa cca gat ctc cga gtt ctt att cca cca<br>Leu Gly Met Asn Asn Arg Lys Pro Asp Leu Arg Val Leu Ile Pro Pro<br>                  250                          255                       260 | | 1184 |
| ggc agc aag aat acg atg cca tca gtg tct gag gat gtc gac ctg ctt<br>Gly Ser Lys Asn Thr Met Pro Ser Val Ser Glu Asp Val Asp Leu Leu<br>                        265                          270                       275 | | 1232 |
| ttg aat caa agg ata aat aac tcc cag tcg gct cag tca ttg gct acc<br>Leu Asn Gln Arg Ile Asn Asn Ser Gln Ser Ala Gln Ser Leu Ala Thr<br>280                         285                        290 | | 1280 |
| cca gtg gtt tcc gta gca act cct act tta cca gga caa gga atg gga<br>Pro Val Val Ser Val Ala Thr Pro Thr Leu Pro Gly Gln Gly Met Gly<br>295                         300                        305 | | 1328 |
| gga tat cca tca gcc att tca aca aca tat ggt acc gag tac tct ctg<br>Gly Tyr Pro Ser Ala Ile Ser Thr Thr Tyr Gly Thr Glu Tyr Ser Leu<br>310                         315                        320                       325 | | 1376 |
| agt agt gca gac ctg tca tct ctg tct ggg ttt aac acc gcc agc gct<br>Ser Ser Ala Asp Leu Ser Ser Leu Ser Gly Phe Asn Thr Ala Ser Ala<br>                  330                          335                       340 | | 1424 |
| ctt cac ctt ggt tca gta act ggc tgg caa cag caa cac cta cat aac<br>Leu His Leu Gly Ser Val Thr Gly Trp Gln Gln Gln His Leu His Asn<br>                        345                          350                       355 | | 1472 |
| atg cca cca tct gcc ctc agt cag ttg gga gct tgc act agc act cat<br>Met Pro Pro Ser Ala Leu Ser Gln Leu Gly Ala Cys Thr Ser Thr His<br>360                         365                        370 | | 1520 |

| | | | | | | | | | | | | | | | | |
|---|---|---|---|---|---|---|---|---|---|---|---|---|---|---|---|---|
| tta | tct | cag | agt | tca | aat | ctc | tcc | ctg | cct | tct | act | caa | agc | ctc | aac | 1568 |
| Leu | Ser | Gln | Ser | Ser | Asn | Leu | Ser | Leu | Pro | Ser | Thr | Gln | Ser | Leu | Asn | |
| | 375 | | | | | 380 | | | | | 385 | | | | | |
| atc | aag | tca | gaa | cct | gtt | tct | cct | cct | aga | gac | cgt | acc | acc | acc | cct | 1616 |
| Ile | Lys | Ser | Glu | Pro | Val | Ser | Pro | Pro | Arg | Asp | Arg | Thr | Thr | Thr | Pro | |
| 390 | | | | | 395 | | | | | 400 | | | | | 405 | |
| tcg | aga | tac | cca | caa | cac | acg | cgc | cac | gag | gcg | ggg | aga | tct | cct | gtt | 1664 |
| Ser | Arg | Tyr | Pro | Gln | His | Thr | Arg | His | Glu | Ala | Gly | Arg | Ser | Pro | Val | |
| | | | | 410 | | | | | 415 | | | | | 420 | | |
| gac | agc | ttg | agc | agc | tgt | agc | agt | tcg | tac | gac | ggg | agc | gac | cga | gag | 1712 |
| Asp | Ser | Leu | Ser | Ser | Cys | Ser | Ser | Ser | Tyr | Asp | Gly | Ser | Asp | Arg | Glu | |
| | | | 425 | | | | | 430 | | | | | 435 | | | |
| gat | cac | cgg | aac | gaa | ttc | cac | tcc | ccc | att | gga | ctc | acc | aga | cct | tcg | 1760 |
| Asp | His | Arg | Asn | Glu | Phe | His | Ser | Pro | Ile | Gly | Leu | Thr | Arg | Pro | Ser | |
| | | 440 | | | | | 445 | | | | | 450 | | | | |
| ccg | gac | gaa | agg | gaa | agt | ccc | tca | gtc | aag | cgc | atg | cga | ctt | tct | gaa | 1808 |
| Pro | Asp | Glu | Arg | Glu | Ser | Pro | Ser | Val | Lys | Arg | Met | Arg | Leu | Ser | Glu | |
| | 455 | | | | | 460 | | | | | 465 | | | | | |

| | | | | |
|---|---|---|---|---|
| gga | tgg | gca | aca | tgatcagatt attacttact agtttttttt ttttcttgc | 1860 |
| Gly | Trp | Ala | Thr | |
| 470 | | | | |

| | | | | | |
|---|---|---|---|---|---|
| agtgtgtgtg | tgtgctatac | cttaatgggg | aagggggggtc | gatatgcatt | atatgtgccg | 1920 |
| tgtgtggaaa | aaaaaaaagt | caggtactct | gttttgtaaa | agtacttta | aattgcctca | 1980 |
| gtgatacagt | ataaagataa | acagaaatgc | tgagataagc | ttagcacttg | agttgtacaa | 2040 |
| cagaacactt | gtacaaaata | gattttaagg | ctaacttctt | ttcactgttg | tgctcctttg | 2100 |
| caaaatgtat | gttacaatag | atagtgtcat | gttgcaggtt | caacgttatt | tacatgtaaa | 2160 |
| tagacaaaag | gaaacatttg | ccaaaagcgg | cagatctttta | ctgaaagaga | gagcagctgt | 2220 |
| tatgcaacat | atagaaaaat | gtatagatgc | ttggacagac | ccggtaatgg | gtggccattg | 2280 |
| gtaaatgtta | ggaacacacc | aggtcacctg | acatcccaag | aatgctcaca | aacctgcagg | 2340 |
| catatcattg | gcgtatggca | ctcattaaaa | aggatcagag | accattaaaa | gaggaccata | 2400 |
| cctattaaaa | aaaaatgtgg | agttggaggg | ctaacatatt | taattaaata | aataaataaa | 2460 |
| tctgggtctg | catctcttat | taaataaaaa | tataaaaata | tgtacattac | attttgctta | 2520 |
| ttttcatata | aaaggtaaga | cagagtttgc | aaagcatttg | tggcttttttg | tagtttactt | 2580 |
| aagccaaaat | gtgtttttttt | ccccttgata | gcttcgctaa | tattttaaac | agtcctgtaa | 2640 |
| aaaaccaaaa | aggactttttt | gtatagaaag | cactaccccta | agccatgaag | aactccatgc | 2700 |
| tttgctaacc | aagataactg | ttttctcttt | gtagaagttt | tgttttttgaa | atgtgtatttt | 2760 |
| ctaattatat | aaaatattaa | gaatctttta | aaaaaatctg | tgaaattaac | atgcttgtgt | 2820 |
| atagctttct | aatatatata | atattatggt | aatagcagaa | gttttgttat | cttaatagcg | 2880 |
| ggagggggt | atatttgtgc | agttgcacat | ttgagtaact | attttctttc | tgttttcttt | 2940 |
| tactctgctt | acatttttata | agtttaaggt | cagctgtcaa | aaggataacc | tgtgggtta | 3000 |
| gaacatatca | cattgcaaca | ccctaaattg | tttttaatac | attagcaatc | tattgggtca | 3060 |
| actgacatcc | attgtatata | ctagtttctt | tcatgctatt | tttattttgt | ttttttgcatt | 3120 |
| tttatcaaat | gcagggcccc | tttctgatct | caccattttca | ccatgcatct | tggaattcag | 3180 |
| taagtgcata | tcctaacttg | cccatattct | aaatcatctg | gttggttttc | agcctagaat | 3240 |
| ttgatacgct | tttttagaaat | atgcccagaa | tagaaaagct | atgttggggc | acatgtcctg | 3300 |
| caaatatggc | cctagaaaca | agtgatatgg | aatttacttg | gtgaataagt | tataaattcc | 3360 |
| cacagaagaa | aaatgtgaaa | gactgggtgc | tagacaagaa | ggaagcaggt | aaagggatag | 3420 |

-continued

```
ttgctttgtc atccgttttt aattatttta actgaccctt gacaatcttg tcagcaatat    3480
aggactgttg aacaatcccg gtgtgtcagg accccaaat gtcacttctg cataaagcat     3540
gtatgtcatc tattttttct tcaataaaga gatttaatag ccatttcaag aaatcccata    3600
aagaacctct ctatgtccct tttttaatt taaaaaatg actcttgtct aatattcgtc      3660
tataagggat taattttcag acctttaat aagtgagtgc cataagaaag tcaatatata    3720
ttgtttaaaa gatatttcag tctaggaaag attttccttc tcttggaatg tgaagatctg    3780
tcgattcatc tccaatcata tgcattgaca tacacagcaa agaagatata ggcagtaata    3840
tcaacactgc tatatcatgt gtaggacatt tcttatccat ttttctctt ttacttgcat     3900 agttgctatg tgtttctcat tgtaaaaggc tgccgctggg tggcagaagc caagagacct    3960
tattaactag gctatatttt tcttaacttg atctgaaatc cacaattaga ccacaatgca    4020
cctttggttg tatccataaa ggatgctagc ctgccttgta ctaatgtttt atatatt       4077
```

<210> SEQ ID NO 6
<211> LENGTH: 473
<212> TYPE: PRT
<213> ORGANISM: Homo sapiens

<400> SEQUENCE: 6

```
Met Gly Arg Lys Lys Ile Gln Ile Thr Arg Ile Met Asp Glu Arg Asn
 1               5                  10                  15

Arg Gln Val Thr Phe Thr Lys Arg Lys Phe Gly Leu Met Lys Lys Ala
                20                  25                  30

Tyr Glu Leu Ser Val Leu Cys Asp Cys Glu Ile Ala Leu Ile Ile Phe
            35                  40                  45

Asn Ser Thr Asn Lys Leu Phe Gln Tyr Ala Ser Thr Asp Met Asp Lys
        50                  55                  60

Val Leu Leu Lys Tyr Thr Glu Tyr Asn Glu Pro His Glu Ser Arg Thr
 65                  70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Pro Asn Phe Glu Met Pro
    130                 135                 140

Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255

Val Leu Ile Pro Pro Gly Ser Lys Asn Thr Met Pro Ser Val Ser Glu
```

-continued

```
                260                 265                 270
Asp Val Asp Leu Leu Asn Gln Arg Ile Asn Asn Ser Gln Ser Ala
                275                 280                 285

Gln Ser Leu Ala Thr Pro Val Val Ser Val Ala Thr Pro Thr Leu Pro
            290                 295                 300

Gly Gln Gly Met Gly Gly Tyr Pro Ser Ala Ile Ser Thr Thr Tyr Gly
305                 310                 315                 320

Thr Glu Tyr Ser Leu Ser Ser Ala Asp Leu Ser Ser Leu Ser Gly Phe
                325                 330                 335

Asn Thr Ala Ser Ala Leu His Leu Gly Ser Val Thr Gly Trp Gln Gln
                340                 345                 350

Gln His Leu His Asn Met Pro Pro Ser Ala Leu Ser Gln Leu Gly Ala
                355                 360                 365

Cys Thr Ser Thr His Leu Ser Gln Ser Ser Asn Leu Ser Leu Pro Ser
                370                 375                 380

Thr Gln Ser Leu Asn Ile Lys Ser Glu Pro Val Ser Pro Pro Arg Asp
385                 390                 395                 400

Arg Thr Thr Thr Pro Ser Arg Tyr Pro Gln His Thr Arg His Glu Ala
                405                 410                 415

Gly Arg Ser Pro Val Asp Ser Leu Ser Ser Cys Ser Ser Ser Tyr Asp
                420                 425                 430

Gly Ser Asp Arg Glu Asp His Arg Asn Glu Phe His Ser Pro Ile Gly
                435                 440                 445

Leu Thr Arg Pro Ser Pro Asp Glu Arg Glu Ser Pro Ser Val Lys Arg
                450                 455                 460

Met Arg Leu Ser Glu Gly Trp Ala Thr
465                 470

<210> SEQ ID NO 7
<211> LENGTH: 1919
<212> TYPE: DNA
<213> ORGANISM: Homo sapiens
<220> FEATURE:
<221> NAME/KEY: CDS
<222> LOCATION: (196)...(1761)

<400> SEQUENCE: 7
caggggcgag ggctacccgc tctttgccgt gacaacaccg ttcccccagc cgggctggag      60
gctgtgcaga aggtatcctg cagaccatga actgagcact gttcccagac cgttcatgag     120
cacagtgtaa ggtgtgccga gacccaccac ccagcgagcc cctcccctcc gtagcactga     180 ggaccccccgg agaag atg ggg agg aaa aag att cag atc cag cga atc acc      231
                 Met Gly Arg Lys Lys Ile Gln Ile Gln Arg Ile Thr
                  1               5                  10 gac gag cgg aac cga cag gtg act ttc acc aag cgg aag ttt ggc ctg        279
Asp Glu Arg Asn Arg Gln Val Thr Phe Thr Lys Arg Lys Phe Gly Leu
         15                  20                  25 atg aag aag gcg tat gag ctg agc gtg cta tgt gac tgc gag atc gca        327
Met Lys Lys Ala Tyr Glu Leu Ser Val Leu Cys Asp Cys Glu Ile Ala
     30                  35                  40 ctc atc atc ttc aac cac tcc aac aag ctg ttc cag tac gcc agc acc        375
Leu Ile Ile Phe Asn His Ser Asn Lys Leu Phe Gln Tyr Ala Ser Thr
 45                  50                  55                  60 gac atg gac aag gtg ctg ctc aag tac acg gag tac aat gag cca cac        423
Asp Met Asp Lys Val Leu Leu Lys Tyr Thr Glu Tyr Asn Glu Pro His
                 65                  70                  75 gag agc cgc acc aac gcc gac atc atc gag acc ctg agg aag aag ggc        471
Glu Ser Arg Thr Asn Ala Asp Ile Ile Glu Thr Leu Arg Lys Lys Gly
```

|       |       |       |       | 80    |       |       |       |       | 85    |       |       |       |       | 90    |       |       |      |
|-------|-------|-------|-------|-------|-------|-------|-------|-------|-------|-------|-------|-------|-------|-------|-------|-------|------|
| ttc   | aat   | ggc   | tgc   | gac   | agc   | ccc   | gag   | ccc   | gac   | ggg   | gag   | gac   | tcg   | ctg   | gaa   |       | 519  |
| Phe   | Asn   | Gly   | Cys   | Asp   | Ser   | Pro   | Glu   | Pro   | Asp   | Gly   | Glu   | Asp   | Ser   | Leu   | Glu   |       |      |
|       |       |       |       | 95    |       |       |       |       | 100   |       |       |       |       | 105   |       |       |      |

| cag | agc | ccc | ctg | ctg | gag | gac | aag | tac | cga | cgc | gcc | agc | gag | gag | ctc | 567 |
|-----|-----|-----|-----|-----|-----|-----|-----|-----|-----|-----|-----|-----|-----|-----|-----|-----|
| Gln | Ser | Pro | Leu | Leu | Glu | Asp | Lys | Tyr | Arg | Arg | Ala | Ser | Glu | Glu | Leu |     |
| 110 |     |     |     |     | 115 |     |     |     |     | 120 |     |     |     |     |     |     |

| gac | ggg | ctc | ttc | cgg | cgc | tat | ggg | tca | act | gtc | ccg | gcc | ccc | aac | ttt | 615 |
|-----|-----|-----|-----|-----|-----|-----|-----|-----|-----|-----|-----|-----|-----|-----|-----|-----|
| Asp | Gly | Leu | Phe | Arg | Arg | Tyr | Gly | Ser | Thr | Val | Pro | Ala | Pro | Asn | Phe |     |
| 125 |     |     |     |     | 130 |     |     |     |     | 135 |     |     |     |     | 140 |     |

| gcc | atg | cct | gtc | acg | gtg | ccc | gtg | tcc | aat | cag | agc | tca | ctg | cag | ttc | 663 |
|-----|-----|-----|-----|-----|-----|-----|-----|-----|-----|-----|-----|-----|-----|-----|-----|-----|
| Ala | Met | Pro | Val | Thr | Val | Pro | Val | Ser | Asn | Gln | Ser | Ser | Leu | Gln | Phe |     |
|     |     |     |     | 145 |     |     |     |     | 150 |     |     |     |     | 155 |     |     |

| agc | aat | ccc | agc | ggc | tcc | ctg | gtc | acc | cct | tcc | ctg | gtg | aca | tca | tcc | 711 |
|-----|-----|-----|-----|-----|-----|-----|-----|-----|-----|-----|-----|-----|-----|-----|-----|-----|
| Ser | Asn | Pro | Ser | Gly | Ser | Leu | Val | Thr | Pro | Ser | Leu | Val | Thr | Ser | Ser |     |
|     |     |     |     | 160 |     |     |     |     | 165 |     |     |     |     | 170 |     |     |

| ctc | acg | gac | ccg | cgg | ctc | ctg | tcc | ccc | cag | cag | cca | gca | cta | cag | agg | 759 |
|-----|-----|-----|-----|-----|-----|-----|-----|-----|-----|-----|-----|-----|-----|-----|-----|-----|
| Leu | Thr | Asp | Pro | Arg | Leu | Leu | Ser | Pro | Gln | Gln | Pro | Ala | Leu | Gln | Arg |     |
|     |     |     | 175 |     |     |     |     | 180 |     |     |     |     | 185 |     |     |     |

| aac | agt | gtg | tct | cct | ggc | ctg | ccc | cag | cgg | cca | gct | agt | gcg | ggg | gcc | 807 |
|-----|-----|-----|-----|-----|-----|-----|-----|-----|-----|-----|-----|-----|-----|-----|-----|-----|
| Asn | Ser | Val | Ser | Pro | Gly | Leu | Pro | Gln | Arg | Pro | Ala | Ser | Ala | Gly | Ala |     |
| 190 |     |     |     |     | 195 |     |     |     |     | 200 |     |     |     |     |     |     |

| atg | ctg | ggg | ggt | gac | ctg | aac | agt | gct | aac | gga | gcc | tgc | ccc | agc | cct | 855 |
|-----|-----|-----|-----|-----|-----|-----|-----|-----|-----|-----|-----|-----|-----|-----|-----|-----|
| Met | Leu | Gly | Gly | Asp | Leu | Asn | Ser | Ala | Asn | Gly | Ala | Cys | Pro | Ser | Pro |     |
| 205 |     |     |     |     | 210 |     |     |     |     | 215 |     |     |     |     | 220 |     |

| gtt | ggg | aat | ggc | tac | gtc | agt | gct | cgg | gct | tcc | cct | ggc | ctc | ctc | cct | 903 |
|-----|-----|-----|-----|-----|-----|-----|-----|-----|-----|-----|-----|-----|-----|-----|-----|-----|
| Val | Gly | Asn | Gly | Tyr | Val | Ser | Ala | Arg | Ala | Ser | Pro | Gly | Leu | Leu | Pro |     |
|     |     |     |     | 225 |     |     |     |     | 230 |     |     |     |     | 235 |     |     |

| gtg | gcc | aat | ggc | aac | agc | cta | aac | aag | gtc | atc | cct | gcc | aag | tct | ccg | 951 |
|-----|-----|-----|-----|-----|-----|-----|-----|-----|-----|-----|-----|-----|-----|-----|-----|-----|
| Val | Ala | Asn | Gly | Asn | Ser | Leu | Asn | Lys | Val | Ile | Pro | Ala | Lys | Ser | Pro |     |
|     |     |     | 240 |     |     |     |     | 245 |     |     |     |     | 250 |     |     |     |

| ccc | cca | cct | acc | cac | agc | acc | cag | ctt | gga | gcc | ccc | agc | cgc | aag | ccc | 999 |
|-----|-----|-----|-----|-----|-----|-----|-----|-----|-----|-----|-----|-----|-----|-----|-----|-----|
| Pro | Pro | Pro | Thr | His | Ser | Thr | Gln | Leu | Gly | Ala | Pro | Ser | Arg | Lys | Pro |     |
|     |     |     | 255 |     |     |     |     | 260 |     |     |     |     | 265 |     |     |     |

| gac | ctg | cga | gtc | atc | act | tcc | cag | gca | gga | aag | ggg | tta | atg | cat | cac | 1047 |
|-----|-----|-----|-----|-----|-----|-----|-----|-----|-----|-----|-----|-----|-----|-----|-----|------|
| Asp | Leu | Arg | Val | Ile | Thr | Ser | Gln | Ala | Gly | Lys | Gly | Leu | Met | His | His |      |
| 270 |     |     |     |     | 275 |     |     |     |     | 280 |     |     |     |     |     |      |

| ttg | act | gag | gac | cat | tta | gat | ctg | aac | aat | gcc | cag | cgc | ctt | ggg | gtc | 1095 |
|-----|-----|-----|-----|-----|-----|-----|-----|-----|-----|-----|-----|-----|-----|-----|-----|------|
| Leu | Thr | Glu | Asp | His | Leu | Asp | Leu | Asn | Asn | Ala | Gln | Arg | Leu | Gly | Val |      |
| 285 |     |     |     |     | 290 |     |     |     |     | 295 |     |     |     |     | 300 |      |

| tcc | cag | tct | act | cat | tcg | ctc | acc | acc | cca | gtg | gtt | tct | gtg | gca | acg | 1143 |
|-----|-----|-----|-----|-----|-----|-----|-----|-----|-----|-----|-----|-----|-----|-----|-----|------|
| Ser | Gln | Ser | Thr | His | Ser | Leu | Thr | Thr | Pro | Val | Val | Ser | Val | Ala | Thr |      |
|     |     |     |     | 305 |     |     |     |     | 310 |     |     |     |     | 315 |     |      |

| ccg | agt | tta | ctc | agc | cag | ggc | ctc | ccc | ttc | tct | tcc | atg | ccc | act | gcc | 1191 |
|-----|-----|-----|-----|-----|-----|-----|-----|-----|-----|-----|-----|-----|-----|-----|-----|------|
| Pro | Ser | Leu | Leu | Ser | Gln | Gly | Leu | Pro | Phe | Ser | Ser | Met | Pro | Thr | Ala |      |
|     |     |     | 320 |     |     |     |     | 325 |     |     |     |     | 330 |     |     |      |

| tac | aac | aca | gat | tac | cag | ttg | acc | agt | gca | gag | ctc | tcc | tcc | tta | cca | 1239 |
|-----|-----|-----|-----|-----|-----|-----|-----|-----|-----|-----|-----|-----|-----|-----|-----|------|
| Tyr | Asn | Thr | Asp | Tyr | Gln | Leu | Thr | Ser | Ala | Glu | Leu | Ser | Ser | Leu | Pro |      |
|     |     | 335 |     |     |     |     | 340 |     |     |     |     | 345 |     |     |     |      |

| gcc | ttt | agt | tca | cct | ggg | ggg | ctg | tcg | cta | ggc | aat | gtc | act | gcc | tgg | 1287 |
|-----|-----|-----|-----|-----|-----|-----|-----|-----|-----|-----|-----|-----|-----|-----|-----|------|
| Ala | Phe | Ser | Ser | Pro | Gly | Gly | Leu | Ser | Leu | Gly | Asn | Val | Thr | Ala | Trp |      |
|     |     | 350 |     |     |     |     | 355 |     |     |     |     | 360 |     |     |     |      |

| caa | cag | cca | cag | cag | ccc | cag | cag | ccg | cag | cag | cca | cag | cct | cca | cag | 1335 |
|-----|-----|-----|-----|-----|-----|-----|-----|-----|-----|-----|-----|-----|-----|-----|-----|------|
| Gln | Gln | Pro | Gln | Gln | Pro | Gln | Gln | Pro | Gln | Gln | Pro | Gln | Pro | Pro | Gln |      |
| 365 |     |     |     |     | 370 |     |     |     |     | 375 |     |     |     |     | 380 |      |

| cag | cag | cca | ccg | cag | cca | cag | cag | cca | cag | cca | cag | cag | cct | cag | cag | 1383 |
|-----|-----|-----|-----|-----|-----|-----|-----|-----|-----|-----|-----|-----|-----|-----|-----|------|
| Gln | Gln | Pro | Pro | Gln | Pro | Gln | Gln | Pro | Gln | Pro | Gln | Gln | Pro | Gln | Gln |      |
|     |     |     |     | 385 |     |     |     |     | 390 |     |     |     |     | 395 |     |      |

| ccg | caa | cag | cca | cct | cag | caa | cag | tcc | cac | ctg | gtc | cct | gta | tct | ctc | 1431 |
|-----|-----|-----|-----|-----|-----|-----|-----|-----|-----|-----|-----|-----|-----|-----|-----|------|
| Pro | Gln | Gln | Pro | Pro | Gln | Gln | Gln | Ser | His | Leu | Val | Pro | Val | Ser | Leu |      |

```
                    400                 405                 410
agc aac ctc atc ccg ggc agc ccc ctg ccc cac gtg ggt gct gcc ctc      1479
Ser Asn Leu Ile Pro Gly Ser Pro Leu Pro His Val Gly Ala Ala Leu
        415                 420                 425 aca gtc acc acc cac ccc cac atc agc atc aag tca gaa ccg gtg tcc      1527
Thr Val Thr Thr His Pro His Ile Ser Ile Lys Ser Glu Pro Val Ser
    430                 435                 440 cca agc cgt gag cgc agc cct gcg cct ccc cct cca gct gtg ttc cca      1575
Pro Ser Arg Glu Arg Ser Pro Ala Pro Pro Pro Pro Ala Val Phe Pro
445                 450                 455                 460 gct gcc cgc cct gag cct ggc gat ggt ctc agc agc cca gcc ggg gga      1623
Ala Ala Arg Pro Glu Pro Gly Asp Gly Leu Ser Ser Pro Ala Gly Gly
                465                 470                 475 tcc tat gag acg gga gac cgg gat gac gga cgg ggg gac ttc ggg ccc      1671
Ser Tyr Glu Thr Gly Asp Arg Asp Asp Gly Arg Gly Asp Phe Gly Pro
            480                 485                 490 aca ctg ggc ctg ctg cgc cca gcc cca gag cct gag gct gag ggc tca      1719
Thr Leu Gly Leu Leu Arg Pro Ala Pro Glu Pro Glu Ala Glu Gly Ser
        495                 500                 505 gct gtg aag agg atg cgg ctt gat acc tgg aca tta aag tga              1761
Ala Val Lys Arg Met Arg Leu Asp Thr Trp Thr Leu Lys *
    510                 515                 520 cgattcccac tccctcctc tcagcctccc tgatgaagag ttgacaatct caccgcccgc     1821
ccttccctgc cccgggctcc tcccgctcga cccccacttc ctttcttgtg cttcgtgtcc    1881
tgttgacggt tacatttgtg tataattatt atattatt                            1919
```

<210> SEQ ID NO 8
<211> LENGTH: 521
<212> TYPE: PRT
<213> ORGANISM: Homo sapiens

<400> SEQUENCE: 8

```
Met Gly Arg Lys Lys Ile Gln Ile Gln Arg Ile Thr Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn His Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ala Asp Ile Ile Glu Thr Leu Arg Lys Lys Gly Phe Asn Gly Cys
                85                  90                  95

Asp Ser Pro Glu Pro Asp Gly Glu Asp Ser Leu Glu Gln Ser Pro Leu
            100                 105                 110

Leu Glu Asp Lys Tyr Arg Arg Ala Ser Glu Glu Leu Asp Gly Leu Phe
        115                 120                 125

Arg Arg Tyr Gly Ser Thr Val Pro Ala Pro Asn Phe Ala Met Pro Val
    130                 135                 140

Thr Val Pro Val Ser Asn Gln Ser Ser Leu Gln Phe Ser Asn Pro Ser
145                 150                 155                 160

Gly Ser Leu Val Thr Pro Ser Leu Val Thr Ser Ser Leu Thr Asp Pro
                165                 170                 175

Arg Leu Leu Ser Pro Gln Gln Pro Ala Leu Gln Arg Asn Ser Val Ser
            180                 185                 190
```

Pro Gly Leu Pro Gln Arg Pro Ala Ser Ala Gly Ala Met Leu Gly Gly
            195                 200                 205

Asp Leu Asn Ser Ala Asn Gly Ala Cys Pro Ser Pro Val Gly Asn Gly
        210                 215                 220

Tyr Val Ser Ala Arg Ala Ser Pro Gly Leu Leu Pro Val Ala Asn Gly
225                 230                 235                 240

Asn Ser Leu Asn Lys Val Ile Pro Ala Lys Ser Pro Pro Pro Pro Thr
                245                 250                 255

His Ser Thr Gln Leu Gly Ala Pro Ser Arg Lys Pro Asp Leu Arg Val
            260                 265                 270

Ile Thr Ser Gln Ala Gly Lys Gly Leu Met His His Leu Thr Glu Asp
        275                 280                 285

His Leu Asp Leu Asn Asn Ala Gln Arg Leu Gly Val Ser Gln Ser Thr
290                 295                 300

His Ser Leu Thr Thr Pro Val Val Ser Val Ala Thr Pro Ser Leu Leu
305                 310                 315                 320

Ser Gln Gly Leu Pro Phe Ser Ser Met Pro Thr Ala Tyr Asn Thr Asp
                325                 330                 335

Tyr Gln Leu Thr Ser Ala Glu Leu Ser Ser Leu Pro Ala Phe Ser Ser
            340                 345                 350

Pro Gly Gly Leu Ser Leu Gly Asn Val Thr Ala Trp Gln Gln Pro Gln
        355                 360                 365

Gln Pro Gln Gln Pro Gln Gln Pro Gln Pro Gln Gln Pro Gln Gln Pro
370                 375                 380

Gln Pro Gln Gln Pro Gln Gln Pro Gln Pro Gln Pro Gln Gln Gln Pro
385                 390                 395                 400

Pro Gln Gln Gln Ser His Leu Val Pro Val Ser Leu Ser Asn Leu Ile
                405                 410                 415

Pro Gly Ser Pro Leu Pro His Val Gly Ala Ala Leu Thr Val Thr Thr
            420                 425                 430

His Pro His Ile Ser Ile Lys Ser Glu Pro Val Ser Pro Ser Arg Glu
        435                 440                 445

Arg Ser Pro Ala Pro Pro Pro Ala Val Phe Pro Ala Ala Arg Pro
450                 455                 460

Glu Pro Gly Asp Gly Leu Ser Ser Pro Ala Gly Ser Tyr Glu Thr
465                 470                 475                 480

Gly Asp Arg Asp Asp Gly Arg Gly Asp Phe Gly Pro Thr Leu Gly Leu
                485                 490                 495

Leu Arg Pro Ala Pro Glu Pro Glu Ala Glu Gly Ser Ala Val Lys Arg
            500                 505                 510

Met Arg Leu Asp Thr Trp Thr Leu Lys
        515                 520

<210> SEQ ID NO 9
<211> LENGTH: 8
<212> TYPE: PRT
<213> ORGANISM: Homo sapiens

<400> SEQUENCE: 9

Ser Glu Glu Glu Glu Leu Glu Leu
1               5

<210> SEQ ID NO 10
<211> LENGTH: 7
<212> TYPE: PRT
<213> ORGANISM: Homo sapiens

```
<400> SEQUENCE: 10

Thr Glu Asp His Leu Asp Leu
  1               5

<210> SEQ ID NO 11
<211> LENGTH: 8
<212> TYPE: PRT
<213> ORGANISM: Homo sapiens

<400> SEQUENCE: 11

Ser Glu Asp Val Asp Leu Leu Leu
  1               5

<210> SEQ ID NO 12
<211> LENGTH: 18
<212> TYPE: DNA
<213> ORGANISM: Artificial Sequence
<220> FEATURE:
<223> OTHER INFORMATION: synthetic

<400> SEQUENCE: 12
tgggctataa atagccgc                                                 18

<210> SEQ ID NO 13
<211> LENGTH: 25
<212> TYPE: PRT
<213> ORGANISM: Homo sapiens
<220> FEATURE:
<221> NAME/KEY: VARIANT
<222> LOCATION: 9, 10, 11, 12, 13, 14, 15, 16, 17
<223> OTHER INFORMATION: Xaa = Any Amino Acid

<400> SEQUENCE: 13

Pro Thr Lys Ser Pro Pro Pro Xaa Xaa Xaa Xaa Xaa Xaa Xaa Xaa
  1               5                  10                  15

Xaa Arg Lys Pro Asp Leu Arg Val Val
             20                  25

<210> SEQ ID NO 14
<211> LENGTH: 39
<212> TYPE: PRT
<213> ORGANISM: Homo sapiens

<400> SEQUENCE: 14

Thr Pro Val Val Ser Val Thr Thr Pro Ser Leu Pro Pro Gln Gly Leu
  1               5                  10                  15

Val Tyr Ser Ala Met Pro Thr Ala Tyr Asn Thr Asp Tyr Ser Leu Thr
             20                  25                  30

Ser Ala Asp Leu Ser Ala Leu
             35

<210> SEQ ID NO 15
<211> LENGTH: 14
<212> TYPE: PRT
<213> ORGANISM: Homo sapiens

<400> SEQUENCE: 15

Ile Ser Ile Lys Ser Glu Pro Ile Ser Pro Pro Arg Asp Arg
  1               5                  10

<210> SEQ ID NO 16
<211> LENGTH: 22
<212> TYPE: PRT
<213> ORGANISM: Homo sapiens
```

```
<400> SEQUENCE: 16

Gly Arg Ser Pro Val Asp Ser Leu Ser Ser Ser Ser Ser Tyr Asp
1               5                   10                  15

Gly Ser Asp Arg Glu Asp
            20

<210> SEQ ID NO 17
<211> LENGTH: 22
<212> TYPE: PRT
<213> ORGANISM: Homo sapiens
<220> FEATURE:
<221> NAME/KEY: VARIANT
<222> LOCATION: 9, 10, 11, 12, 13, 14
<223> OTHER INFORMATION: Xaa = Any Amino Acid

<400> SEQUENCE: 17

Gln Ala Lys Ser Pro Pro Met Xaa Xaa Xaa Xaa Xaa Xaa Arg Lys
1               5                   10                  15

Pro Asp Leu Arg Val Leu
            20

<210> SEQ ID NO 18
<211> LENGTH: 41
<212> TYPE: PRT
<213> ORGANISM: Homo sapiens

<400> SEQUENCE: 18

Thr Pro Val Val Ser Val Ala Thr Pro Thr Leu Pro Gly Gln Gly Met
1               5                   10                  15

Gly Gly Tyr Pro Ser Ala Ile Ser Thr Thr Tyr Gly Thr Glu Tyr Ser
            20                  25                  30

Leu Ser Ser Ala Asp Leu Ser Ser Leu
        35                  40

<210> SEQ ID NO 19
<211> LENGTH: 14
<212> TYPE: PRT
<213> ORGANISM: Homo sapiens

<400> SEQUENCE: 19

Leu Ser Ile Lys Ser Glu Pro Val Ser Pro Pro Arg Asp Arg
1               5                   10

<210> SEQ ID NO 20
<211> LENGTH: 22
<212> TYPE: PRT
<213> ORGANISM: Homo sapiens

<400> SEQUENCE: 20

Gly Arg Ser Pro Val Asp Ser Leu Ser Ser Cys Ser Ser Tyr Gly
1               5                   10                  15

Asp Ser Asp Arg Glu Asp
            20

<210> SEQ ID NO 21
<211> LENGTH: 26
<212> TYPE: PRT
<213> ORGANISM: Homo sapiens
<220> FEATURE:
<221> NAME/KEY: VARIANT
<222> LOCATION: 9, 10, 11, 12, 13, 14, 15, 16, 17, 18
<223> OTHER INFORMATION: Xaa = Any Amino Acid

<400> SEQUENCE: 21
```

```
Pro Ala Lys Ser Pro Pro Pro Xaa Xaa Xaa Xaa Xaa Xaa Xaa
1               5                   10                  15

Xaa Xaa Arg Lys Pro Asp Leu Arg Val Ile
            20                  25

<210> SEQ ID NO 22
<211> LENGTH: 39
<212> TYPE: PRT
<213> ORGANISM: Homo sapiens

<400> SEQUENCE: 22

Thr Pro Val Val Ser Val Ala Thr Pro Ser Leu Leu Ser Gln Gly Leu
1               5                   10                  15

Pro Phe Ser Ser Met Pro Thr Ala Tyr Asn Thr Asp Tyr Gln Leu Pro
            20                  25                  30

Ser Ala Glu Leu Ser Ser Leu
        35

<210> SEQ ID NO 23
<211> LENGTH: 14
<212> TYPE: PRT
<213> ORGANISM: Homo sapiens

<400> SEQUENCE: 23

Ile Ser Ile Lys Ser Glu Pro Val Ser Pro Ser Arg Glu Arg
1               5                   10

<210> SEQ ID NO 24
<211> LENGTH: 12
<212> TYPE: PRT
<213> ORGANISM: Homo sapiens

<400> SEQUENCE: 24

Pro His Glu Ser Arg Thr Asn Ser Asp Ile Val Glu
1               5                   10

<210> SEQ ID NO 25
<211> LENGTH: 14
<212> TYPE: DNA
<213> ORGANISM: Artificial Sequence
<220> FEATURE:
<223> OTHER INFORMATION: synthetic

<400> SEQUENCE: 25
ytaatatata ttar                                                          14
```

METHODS OF DIFFERENTIATING AND PROTECTING CELLS BY MODULATING THE P38/MEF2 PATHWAY This application is a continuation of U.S. patent application Ser. No. 09/876,187, filed Jun. 5, 2001, now U.S. Pat. No. 7,919,317 which is based on, and claims the benefit of, U.S. Provisional Application No. 60/209,539, filed Jun. 5, 2000, and which is incorporated herein by reference.

This application was made with government support under P01 HD29587 awarded by the National Institute of Health. The government has certain rights in the invention.

BACKGROUND OF THE INVENTION

1. Field of the Invention

The invention relates to neuronal cell transplantation for neurodegenerative conditions of the central nervous system including hypoxia-ischemia (stroke), Parkinson's disease, Huntington's disease, amyotrophic lateral sclerosis, Alzheimer's disease and other forms of dementia and, more specifically, to methods of producing populations of neurons by manipulating the myocyte enhancer factor 2 (MEF2) transcription pathway.

2. Background Information

For a variety of serious neurodegenerative diseases, there exist no effective therapies or cures. For example, Parkinson's disease is a progressive and ultimately fatal neurodegenerative disorder characterized by loss of the pigmented dopaminergic neurons of the substantia nigra. The symptoms of Parkinson's disease can often be managed initially by administration of L-DOPA, the immediate precursor of dopamine. However, reduced efficacy of L-DOPA treatment typically occurs over time. Programmed cell death (apoptosis) has been implicated in this neurodegenerative disorder.

In Alzheimer's disease, the most common neurodegenerative disease and most frequent cause of dementia, progressive failure of memory and degeneration of temporal and parietal association cortex result in speech impairment and loss of coordination, and, in some cases, emotionally disturbance. Alzheimer's disease generally progresses over many years, with patients gradually becoming immobile, emaciated and susceptible to pneumonia.

The brain constitutes a privileged transplantation site and, under the appropriate conditions, neuronal tissues can survive transplantation into the damaged brain, integrate with the host and alleviate functional impairments associated with neurological disease. Neuronal cell transplantation has been sought for a variety of serious neurodegenerative diseases for which no effective therapeutic course exists, including Parkinson's disease and Alzheimer's disease as well as Huntington's disease, amyotrophic lateral sclerosis, multiple sclerosis, epilepsy and pain.

Present techniques for neuronal transplantation have chiefly relied on embryonic or fetal tissues since central nervous system (CNS) neurons only survive transplantation if taken from embryonic or neonatal donors. Neuronal transplantation has been hampered by extremely limited supplies of human embryonic or fetal tissue. In order to develop alternative supplies of donor neurons, scientists have attempted the large scale expansion of stem cells and precursor cells. When treated with high doses of epidermal growth factor, stem and precursor cells from the brain can be selectively expanded in vitro and grown exponentially through multiple passages. These expanded cells, which can be produced from human tissues, yield both neuronal and glial cell types when allowed to differentiate in vitro and survive transplantation back into animal central nervous system (CNS; Svendsen et al., *Exp. Neurol.* 140:1-13 (1996)).

Unfortunately, the expansion of stem and precursor cell populations currently does not produce a cell population useful for therapeutic transplantation, since a relatively small number of neurons is produced, and even a smaller number survive and express the neuronal phenotype when grafted into the central nervous system. Thus, there is a need for a method of efficiently producing large numbers of neuronal cells or their precursors which are capable of surviving when transplanted into the central nervous system in vivo.

The present invention satisfies this need and provides related advantages as well.

SUMMARY OF THE INVENTION

The present invention provides a method of differentiating progenitor cells by contacting the progenitor cells with a differentiating agent; and introducing into the progenitor cells a nucleic acid molecule encoding a MEF2 polypeptide or an active fragment thereof, thereby differentiating the progenitor cells to produce a cell population containing protected neuronal cells. In one embodiment, the produced population containing protected neuronal cells contains at least 50% neuronal cells.

A method of the invention can be practiced, for example, with a nucleic acid molecule encoding human MEF2C, or an active fragment thereof. In one embodiment, the MEF2 polypeptide is constitutively active. In another embodiment, the constitutively active MEF2 polypeptide is a MEF2/VP16 fusion protein. In a further embodiment, the constitutively active MEF2 polypeptide contains one or more serine/threonine to aspartic acid/glutamic acid substitutions in the MEF2 transactivation domain.

A method of the invention for differentiating progenitor cells to produce a cell population containing protected neuronal cells can further include the step of inhibiting caspase activity in the progenitor cells.

Progenitor cells useful in the methods of the invention can be, for example, human stem cells. In one embodiment, the progenitor cells are embryonic stem cells, for example, human embryonic stem cells. In another embodiment, the progenitor cells are hematopoietic progenitor cells, for example, human hematopoietic progenitor cells.

In one embodiment, a method of the invention further includes the step of selecting CD133-positive (AC133-positive) human progenitor cells. In another embodiment, a method of the invention includes the step of selecting CD133-positive/CD34-positive human progenitor cells. In a further embodiment, a method of the invention further includes the step of selecting CD133-positive/CD34-negative human progenitor cells. In yet further embodiments, CD133-positive/CD34-negative/CD45-negative, or CD34-negative/CD38-negative/Lin-negative human progenitor cells or CD34-positive/CD38-negative/Lin-negative/Thy-1-negative human progenitor cells are selected.

For use in a method of the invention, the differentiating agent can be, for example, retinoic acid. Other differentiating agents useful in a method of the invention for producing a cell population containing protecting neurotrophic factor 3, epidermal growth factor, insulin-like growth factor 1 and a platelet-derived growth factor.

In a further embodiment, a method of the invention further includes the step of transplanting cells containing a nucleic acid molecule encoding a MEF2 polypeptide or an active fragment thereof into a patient to produce a cell population containing protected neuronal cells in the patient.

The invention further provides an isolated stem cell that contains an exogenous nucleic acid molecule encoding a MEF2 polypeptide or an active fragment thereof. The isolated stem cell can include, for example, a nucleic acid molecule encoding a MEF2 polypeptide, or active fragment thereof, operatively linked to a heterologous regulatory element. The encoded MEF2 polypeptide can be, for example, a human MEF2 polypeptide. If desired, the encoded MEF2 polypeptide can be a MEF2C polypeptide. In a further embodiment, the MEF2 polypeptide is constitutively active. Such a constitutively active MEF2 polypeptide can be, for example, a constitutively active MEF2C polypeptide. In one embodiment, the constitutively active MEF2 polypeptide is a MEF2/VP16 fusion protein. In another embodiment, the constitutively active MEF2 polypeptide contains one or more serine/threonine to aspartic acid/glutamic acid substitutions in the MEF2 transactivation domain.

An isolated stem cell of the invention can be, for example, a human stem cell. In one embodiment, the stem cell is an embryonic stem cell, for example, a human embryonic stem cell. A human stem cell of the invention can contain, for example, an exogenous nucleic acid molecule encoding human MEF2C. A human stem cell of the invention also can include a constitutively active MEF2 polypeptide.

The invention further provides an isolated hematopoietic stem cell that contains an exogenous nucleic acid molecule encoding a MEF2 polypeptide or an active fragment thereof. Such an isolated hematopoietic stem cell can include, for example, a nucleic acid molecule encoding a MEF2 polypeptide, or active fragment thereof, operatively linked to a heterologous regulatory element. In one embodiment, an isolated hematopoietic stem cell of the invention is a human hematopoietic stem cell.

The present invention also provides a method of identifying a protective or differentiation gene, which can be, for example, a neuroprotective gene or a gene that contributes to neuronal or muscle cell differentiation. A method of the invention includes the steps of isolating a first cell population; isolating a second cell population, wherein the second cell population has an altered level or activity of a MEF2 polypeptide as compared to the first cell population; and assaying for differential gene expression in the first cell population as compared to the second cell population, whereby a gene differentially expressed in the second cell population as compared to the first cell population is identified as a protective or differentiation gene. In one embodiment, the first cell population is a progenitor cell population, the second cell population is a neuronal cell population, and the differentially expressed gene is a neuronal differentiation gene. In a further embodiment, the first cell population is a progenitor cell population, the second cell population is a muscle cell population, and the differentially expressed gene is a muscle differentiation gene. In yet another embodiment, both cell populations are neuronal cell populations, the second cell population has been subject to a neuronal stress as compared to the first cell population, and the differentially expressed gene is a neuroprotective gene.

Further provided by the invention is a method of identifying a protective gene in vitro. The method is practiced by inducing the p38/MEF2 pathway in a cell in vitro to produce a protected cell; stressing the cell; and assaying for differential gene expression in the protected cell as compared to gene expression in a control cell, whereby a gene differentially expressed in the protected cell as compared to the control cell is identified as a protective gene. In such a method of the invention, the p38/MEF2 pathway can be induced, for example, by introducing into the cell a nucleic acid molecule encoding a MEF2 polypeptide. The MEF2 polypeptide can be, for example, a human MEF2 polypeptide and further can be, if desired, a constitutively active MEF2 polypeptide. In one embodiment, a neuroprotective gene is identified by inducing the p38/MEF2 pathway in a neuron. In another embodiment, a muscle protective gene is identified by inducing the p38/MEF2 pathway in a muscle cell. In a method of the invention, the differential gene expression that identifies the protective gene can be increased or decreased gene expression.

The invention additionally provides a method of identifying a differentiation gene in vitro by inducing the p38/MEF2 pathway in a progenitor cell in vitro to produce a differentiated cell; and assaying for differential gene expression in the differentiated cell as compared to gene expression in a control cell, whereby a gene differentially expressed in the differentiated cell as compared to the control cell is identified as a differentiation gene. In a method of the invention, the p38/MEF2 pathway can be induced, for example, by introducing into the progenitor cell a nucleic acid molecule encoding a MEF2 polypeptide. The MEF2 polypeptide can be, for example, a human MEF2 polypeptide or a constitutively active MEF2 polypeptide. In one embodiment, the differentiated cell is a neuronal cell, and, in a further embodiment, the differentiated cell is a muscle cell. The differential gene expression which serves to identify the differentiation gene can be increased or decreased gene expression.

BRIEF DESCRIPTION OF THE DRAWINGS

FIG. 2A shows the nucleotide sequence (SEQ ID NO: 1) of human MEF2A (GenBank accession NM 005587). FIG. 2B shows the amino acid sequence (SEQ ID NO: 2) of human MEF2A.

FIG. 3A shows the nucleotide sequence (SEQ ID NO: 3) of human MEF2B (GenBank accession NM 005919). FIG. 3B shows the amino acid sequence (SEQ ID NO: 4) of human MEF2B.

FIG. 4A shows the nucleotide sequence (SEQ ID NO: 5) of human MEF2C (GenBank accession L08895). FIG. 4B shows the amino acid sequence (SEQ ID NO: 6) of human MEF2C. The MADS domain is bolded while the MEF2 domain is underlined.

FIG. 5A shows the nucleotide sequence (SEQ ID NO: 7) of human MEF2D (GenBank accession NM 005920). FIG. 5B shows the amino acid sequence (SEQ ID NO: 8) of human MEF2D.

FIG. 6 shows MEF2 binding activity, protein expression and transfection during neuronal differentiation of P19 stem cells. (A) Gel shift assays show that MEF2 binding activity increased during neuronal differentiation of P19 cells. A 32P-labeled MEF2 site oligonucleotide was incubated with nuclear extracts from undifferentiated P19 cells (lanes 1 and 3), or from P19 cells treated with retinoic acid for 2 d (lanes 2 and 4). Cold competition by unlabeled MEF2 site oligonucleotides (lanes 3 and 4). (B) Antibody to MEF2A (lane 6), MEF2C (lane 7), or MEF2D (lane 8) was added to the binding mixture for supershift assays. Anti-MEF2C yielded two supershifted bands, representing one or more DNA complexes containing MEF2C, while anti-MEF2D produced a single supershifted complex (arrows; Leifer et al., *Proc. Natl. Acad. Sci. USA* 90:1546-1550 (1993)). (C) Immunoblots revealed that protein expression of MEF2C and MEF2D was induced during neuronal differentiation of P19 cells. Whole cell lysates from undifferentiated P19 cells or P19 cells treated with retinoic acid for 2 days were used for these immunoblots (n.s., non-specific bands). (D-G) Overexpression of MEF2C induced a mixed neurogenic/myogenic phenotype. Undifferentiated P19 cells did not display immunoreactivity for MEF2C or neurofilament (D, phase contrast image; E, immunocytochemistry). Undifferentiated P19 cells were transfected with an expression vector for MEF2C. Similar findings were observed in 16 experiments in which over 200 cells were scored.

FIG. 8 shows that inhibition of MEF2 function decreases the number of multipotent and unipotent precursor cells. Control cultures (clone 2-1) and MEF2 dominant negative cultures (clone 2-7) were treated with retinoic acid for 3.0 d or 3.5 days. (A and C) Cells incubated with anti-nestin to label multipotent precursor cells (A) or anti-Hu to label unipotent precursor cells (C). Labeled cells were visualized with peroxidase. (B and D) The number of nestin-positive cells (B) and Hu-positive cells (D) in 40 randomly selected fields was scored in a blinded fashion. Values are mean±SD from at least three independent experiments (*, P<0.02 by Student's t-test).

FIG. 9 shows the effects of inhibition of MEF2 function during neuronal differentiation of P19 cells. Control cultures (clone 2-1), MEF2 dominant negative cultures (clone 2-7, labeled DN) and mutated MEF2 dominant negative cultures (clone 2-16, labeled DNmt) were treated with retinoic acid for 3 days. (A) Representative apoptotic cells with condensed nuclei from a MEF2 dominant negative clone treated with retinoic acid and stained with Hoechst dye to detect apoptotic morphology (white arrows). (B) Percentage of apoptotic cells in control or MEF2 dominant negative cultures before and after retinoic acid treatment. (C) Similar percentage of apoptotic cells in control or mutated MEF2 dominant negative cultures after 3 days of retinoic acid. (D) Apoptosis in control, dominant negative or mutated dominant negative cultures treated with retinoic acid for 3 days scored by the TUNEL technique. (E and F) Lack of effect of MEF2 dominant negative on multipotent precursor cell proliferation. Control cultures and MEF2 dominant negative cultures were treated with retinoic acid for 3 days. BrdU was then added to visualize proliferating cells. (E) Dividing multipotent precursor cells detected by double staining with anti-BrdU antibody and anti-nestin antibody in retinoic acid-treated control cells. (F) Comparison of BrdU incorporation into multipotent (nestin-positive) precursor cells in control and MEF2 dominant negative cultures. Values are mean±SD from at least three independent experiments (*, P<0.05 by Student's t-test; †, P<0.001 by ANOVA and post-hoc comparison).

DETAILED DESCRIPTION OF THE INVENTION

Figure 1A:
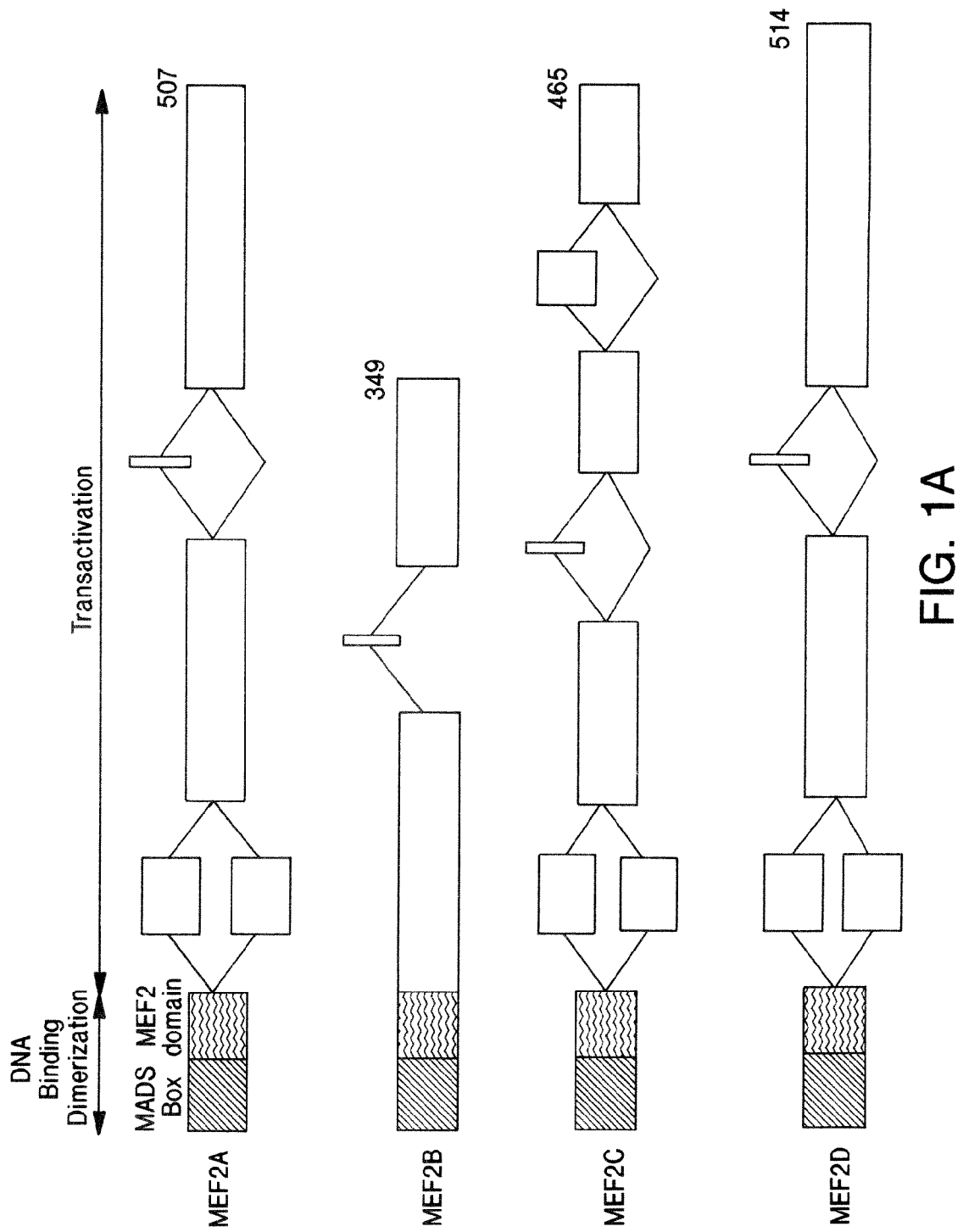
FIG. 1A shows schematic diagrams of MEF2 factors. Structures of the four vertebrate mef2 gene products are shown. Alternative exons within the C-terminal activation domains are indicated, along with the number of amino acids in the longer form of each protein.

MEF2 proteins are members of the MADS family of transcription factors (Treisman, R., *Nature* 376:468-469 (1995)). Four members of the family (MEF2A, MEF2B, MEF2C and MEF2D) have been reported, including murine and human polypeptides (Pollock and Treisman, *Genes & Dev.* 5:2327-2341 (1991); Leifer et al., *Proc. Natl. Acad. Sci. USA* 90:1546-1550 (1993); Martin et al., *Proc. Natl. Acad. Sci. USA* 90:5282-5286 (1993); Martin et al., *Mol. Cell. Biol.* 14:1647-1656 (1994); and Molkentin et al., *Mol. Cell. Biol.* 16:3814-3824 (1996)), and one MEF2 homolog, D-MEF2, has been identified in *Drosophila* (Lilly et al., *Proc. Natl. Acad. Sci. USA* 91:5662-5666 (1994)). Various MAP kinases (p38α, p38β2, and BMK1/ERK5) phosphorylate and thereby activate MEF2 family members (Han et al., *Nature* 386:296-299 (1997); Kato et al., *EMBO J.* 16:7054-7066 (1997); Zhao et al., *Mol. Cell. Biol.* 19:21-30 (1999); and Yang et al., *Mol. Cell. Biol.* 19:4028-4038 (1999)). These MAP kinase pathways lead to MEF2 modulation of gene expression (Han et al., *Nature* 386:296-299 (1997); Kato et al., *EMBO J.* 16:7054-7066 (1997); and Zhao et al., *Mol. Cell. Biol.* 19:21-30 (1999)).

The MEF2 family of genes is highly expressed in cells of muscle lineage, and several studies support a role for MEF2 in myogenesis (Martin et al., *Proc. Natl. Acad. Sci. USA*

90:5282-5286 (1993); Martin et al., *Mol. Cell. Biol.* 14:1647-1656 (1994); Molkentin et al., *Mol. Cell. Biol.* 16:3814-3824 (1996); and McDermott et al., *Mol. Cell. Biol.* 13:2564-2577 (1993)). In D-mef2 loss-of-function *Drosophila*, muscle cells have lost the ability to differentiate (Lilly et al., *Science* 267:688-693 (1995)), and MEF2C-null mice are embryonic lethal due to malformation of the heart (Lin et al., *Science* 276:1404-1407 (1997)). Furthermore, a dominant negative form of MEF2 also inhibits myotube formation in myoblastic cell lines (Ornatsky et al., *J. Biol. Chem.* 272:33271-33278 (1997)). During myogenesis, evidence indicates that MEF2 proteins physically interact with the basic helix-loop-helix (bHLH) myogenic transcription factors MyoD and myogenin to initiate muscle development (Kaushal et al., *Science* 266: 1236-1240 (1994) and Molkentin et al., *Cell* 83:1125-1136 (1995)).

MEF2 family members including MEF2C also are highly expressed in neurons in the central nervous system (CNS) (Lyons et al., *J. Neurosci.* 15:5727-5738 (1995); Leifer et al., *Proc. Natl. Acad. Sci. USA* 90:1546-1550 (1993)). The level of MEF2 expression increases in differentiating neurons in the developing brain (Leifer et al., *Proc. Natl. Acad. Sci. USA* 90:1546-1550 (1993); Lyons et al., *J. Neurosci.* 15:5727-5738 (1995); Leifer et al., *Neuroscience* 63:1067-1079 (1994); and Lin et al., *Mol. Brain. Res.* 42:307-316 (1996)). Several neuronal bHLH transcription factors have been identified during mammalian development (Lee et al., *Mol. Cell. Biol.* 17:2745-2755 (1997)). Ectopic overexpression of neuronal bHLH factors NeuroD(1)/BETA2, NeuroD2/KW8/NDRF, or NeuroD3/neurogenin1 in *Xenopus* causes neurogenic conversion of ectoderm (Lee et al., *Mol. Cell. Biol.* 17:2745-2755 (1997)). In addition, physical and functional interaction between a neuronal bHLH transcription factor (Mash-1) and MEF2 proteins has been reported (Skerjanc and Wilton, *FEBS Letters* 472:53-56 (2000); Mao and Nadal-Ginard, *J. Biol. Chem.* 271:14371-14375 (1996); and Black et al., *J. Biol. Chem.* 271:26659-26663 (1996)).

The present invention relates to the finding that the p38α/MEF2 pathway plays an important role in preventing apoptotic cell death during neuronal differentiation. Based on this finding, the present invention provides a method of differentiating progenitor cells to produce a population of neuronal cells which is protected from apoptotic cell death. The method includes the steps of contacting the progenitor cells with a differentiating agent and inducing the p38 mitogen-activated protein kinase/myocyte enhancer factor 2 (p38 MAP kinase/MEF2) pathway in the progenitor cells, thereby differentiating the progenitor cells to produce a population containing protected neuronal cells. In one embodiment, the MAP kinase/MEF2 pathway is induced by introducing into the progenitor cells a nucleic acid molecule encoding a MEF2 polypeptide or an active fragment thereof. A MEF2 polypeptide useful in a method of the invention can be, for example, a human MEF2 polypeptide or an active fragment thereof and, in one embodiment, is a MEF2C polypeptide or active fragment thereof, for example, a human MEF2C polypeptide or active fragment thereof.

In another embodiment, a method of the invention for differentiating progenitor cells is practiced by introducing into the progenitor cells a nucleic acid molecule encoding a constitutively active MEF2 polypeptide such as a constitutively active form of MEF2A, MEF2B, MEF2C or MEF2D. In a further embodiment, the constitutively active form of the MEF2 polypeptide is resistant to caspase cleavage. A constitutively active MEF2 polypeptide useful in the invention can be, for example, a chimera in which the native MEF2 activation domain is replaced with a heterologous activation domain, for example, a constitutively active MEF2A/VP16, MEF2A/GAL4, MEF2B/VP16, MEF2B/GAL4, MEF2C/VP16, MEF2C/GAL4, MEF2D/VP16 or MEF2D/GAL4 fusion protein. A constitutively active MEF2 polypeptide useful in the invention also can be, for example, a modified MEF2 polypeptide in which one or all of the p38 kinase phosphorylation sites in the MEF2 transactivation domain are substituted with an aspartic or glutamic acid residue. In a further embodiment, a method of the invention is practiced by introducing into the progenitor cells a MEF2 activator, whereby the p38/MEF2 pathway is induced. Such a MEF2 activator can be, for example, a nucleic acid molecule encoding p38α.

In another embodiment, a method of the invention for differentiating progenitor cells to produce a population containing protected neuronal cells is practiced by introducing into the progenitor cells a caspase inhibitor in addition to administering the agent that induces the p38/MEF2 pathway. It is understood that the caspase inhibitor can be administered together with, prior to or following administration of the agent that induces the p38/MEF2 pathway. In one embodiment, a method of the invention is practiced by introducing into the progenitor cells a caspase inhibitor in addition to a constitutively active MEF2 polypeptide.

In a further embodiment, the MAP kinase/MEF2 pathway is induced by introducing into the progenitor cells a MEF2 activator such as a nucleic acid molecule encoding p38α. A population containing protected neuronal cells produced by a method of the invention can be made up of, for example, at least 50% neuronal cells. If desired, cells containing a nucleic acid molecule encoding a MEF2 polypeptide or an active fragment thereof can be transplanted into a patient, for example, into the brain, central nervous system or retina, to produce a cell population containing protected neuronal cells in the patient.

The present invention also provides a method of reducing the severity of a neurologic condition in a subject by administering to the subject an agent that induces the p38 mitogen-activated protein kinase/myocyte enhancer factor 2 (MEF2) pathway. A method of the invention can be useful, for example, in reducing the severity of an acute neurologic condition such as cerebral ischemia; stroke; hypoxia; anoxia; poisoning by—carbon monoxide, manganese or cyanide; hypoglycemia; mechanical trauma to the nervous system such as trauma to the head or spinal cord; or epileptic seizure. A method of the invention further can be useful, for example, for reducing the severity of a chronic neurodegenerative disease such as Huntington's disease; a disorder of photoreceptor degeneration such as retinitis pigmentosa; acquired immunodeficiency syndrome (AIDS) dementia complex; a neuropathic pain syndrome such as causalgia or a painful peripheral neuropathy; olivopontocerebellar atrophy; Parkinsonism; amyotrophic lateral sclerosis; a mitochondrial abnormality or other biochemical disorder such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy; Alzheimer's disease, hepatic encephalopathy, Tourette's syndrome, or drug addiction, tolerance or dependency. Thus, in one embodiment, a method of the invention reduces the severity of stroke; hypoglycemia; trauma; epilepsy; neuropathic pain; peripheral neuropathy, for example, associated with diabetes mellitus; glaucoma; multiple sclerosis. In another embodiment, a method of the invention reduces the severity of Alzheimer's disease, Huntington's disease, acquired AIDS dementia complex, or amyotrophic lateral sclerosis. In a further embodiment, a method of the invention reduces the severity of depression, anxiety, or drug dependency, drug withdrawal or drug addiction.

A method of the invention for reducing the severity of a neurologic condition can be practiced, for example, by administering to a subject a nucleic acid molecule encoding a MEF2 polypeptide or an active fragment thereof. A MEF2 polypeptide useful in a method of the invention can be, for example, a human MEF2 polypeptide or an active fragment thereof and, in one embodiment, is a MEF2C polypeptide or active fragment thereof, for example, a human MEF2C polypeptide or active fragment thereof.

In another embodiment, a method of the invention for reducing the severity of a neurologic condition is practiced by administering to a subject a nucleic acid molecule encoding a constitutively active MEF2 polypeptide such as a constitutively active form of MEF2A, MEF2B, MEF2C or MEF2D. In a further embodiment, the constitutively active form of the MEF2 polypeptide is resistant to caspase cleavage. A constitutively active MEF2 polypeptide useful in the invention can be, for example, a chimera in which the native MEF2 activation domain is replaced with a heterologous activation domain, for example, a constitutively active MEF2A/VP16, MEF2A/GAL4, MEF2B/VP16, MEF2B/GAL4, MEF2C/VP16, MEF2C/GAL4, MEF2D/VP16 or MEF2D/GAL4 fusion protein. A constitutively active MEF2 polypeptide useful in the invention also can be, for example, a modified MEF2 polypeptide in which one or all of the p38 kinase phosphorylation sites in the MEF2 transactivation domain are substituted with an aspartic or glutamic acid residue. In a further embodiment, a method of the invention is practiced by administering to a subject a MEF2 activator, whereby the p38 mitogen-activated protein kinase/myocyte enhancer factor 2 (MEF2) pathway is induced. Such a MEF2 activator can be, for example, a nucleic acid molecule encoding p38α.

In another embodiment, a method of the invention for reducing the severity of a neurologic condition by administering a caspase inhibitor in addition to administering the agent that induces the p38/MEF2 pathway. It is understood that the caspase inhibitor can be administered together with, prior to or following administration of the agent that induces the p38/MEF2 pathway. In one embodiment, a method of the invention is practiced by administering a caspase inhibitor in addition to a constitutively active MEF2 polypeptide.

The invention further provides a method of protecting a neuron from cell death by inducing in the neuron the p38 mitogen-activated protein kinase/myocyte enhancer factor 2 (MEF2) pathway. Such a neuron can be, for example, an adult neuron. A method of the invention can be useful, for example, in protecting a neuron from apoptotic cell death due to an insult such as NMDA receptor-mediated toxicity, or oxidative or nitrosative stress. In one embodiment, a method of the invention for protecting a neuron from cell death is practiced by introducing into the neuron a nucleic acid molecule encoding a MEF2 polypeptide or an active fragment thereof. A method of the invention can be practiced, for example, by introducing into a neuron a nucleic acid molecule encoding a human MEF2 polypeptide or an active fragment thereof and, in one embodiment, is practiced by introducing into a neuron a MEF2C polypeptide or active fragment thereof, for example, a human MEF2C polypeptide or active fragment thereof.

In another embodiment, a method of the invention is practiced by introducing into a neuron a nucleic acid molecule encoding a constitutively active MEF2 polypeptide such as a constitutively active form of MEF2A, MEF2B, MEF2C or MEF2D. In a further embodiment, the constitutively active form of the MEF2 polypeptide is resistant to caspase cleavage. A constitutively active MEF2 polypeptide can be, for example, a chimera in which the native MEF2 activation domain is replaced with a heterologous activation domain, for example, a constitutively active MEF2A/VP16, MEF2A/GAL4, MEF2B/VP16, MEF2B/GAL4, MEF2C/VP16, MEF2C/GAL4, MEF2D/VP16 or MEF2D/GAL4 fusion proteins. A constitutively active MEF2 polypeptide also can be, for example, a modified MEF2 polypeptide in which one or all of the p38 kinase phosphorylation sites in the MEF2 transactivation domain are substituted with an aspartic or glutamic acid residue. In yet a further embodiment, a method of the invention is practiced by introducing into a neuron a MEF2 activator in order to induce the p38 mitogen-activated protein kinase/myocyte enhancer factor 2 (MEF2) pathway in the neuron. Exemplary MEF2 activators useful in the invention include p38α-encoding nucleic acid molecules.

In a further embodiment, a method of the invention for protecting a neuron from cell death is practiced by inducing the p38/MEF2 pathway and further introducing a caspase inhibitor into the neuron. It is understood that the caspase inhibitor can be administered together with, prior to, or following induction of the p38/MEF2 pathway. In one embodiment, a neuron is protected from cell death by introducing into the neuron a constitutively active MEF2 polypeptide and a caspase inhibitor.

The invention also provides a method of protecting a muscle cell from cell death by inducing in the muscle cell the p38 mitogen-activated protein kinase/myocyte enhancer factor 2 (MEF2) pathway. Such a muscle cell can be, for example, an adult muscle cell. A method of the invention can be useful, for example, in protecting a heart muscle cell from injury in a subject susceptible to heart attack (myocardial infarction). In one embodiment, a method of the invention for protecting a muscle cell from cell death is practiced by introducing into the muscle cell a nucleic acid molecule encoding a MEF2 polypeptide or an active fragment thereof. A method of the invention can be practiced, for example, by introducing into the muscle cell a nucleic acid molecule encoding a human MEF2 polypeptide or an active fragment thereof. In one embodiment, a method of the invention is practiced by introducing into the muscle cell a MEF2C polypeptide or an active fragment thereof, for example, a human MEF2C polypeptide or an active fragment thereof.

In another embodiment, a method of the invention is practiced by introducing into a muscle cell a nucleic acid molecule encoding a constitutively active MEF2 polypeptide such as a constitutively active form of MEF2A, MEF2B, MEF2C or MEF2D. In one embodiment, the constitutively active form of the MEF2 polypeptide is resistant to caspase cleavage. In yet a further embodiment, a method of the invention for protecting a muscle cell from cell death is practiced by introducing into the muscle cell a constitutively active MEF2 polypeptide in which the native MEF2 activation domain is replaced with a heterologous activation domain, for example, a constitutively active MEF2A/VP16, MEF2A/GAL4, MEF2B/VP16, MEF2B/GAL4, MEF2C/VP16, MEF2C/GAL4, MEF2D/VP16 or MEF2D/GAL4 fusion proteins. A constitutively active MEF2 polypeptide useful in protecting a muscle cell from cell death also can be, for example, a modified MEF2 polypeptide in which one or all of the p38 kinase phosphorylation sites in the MEF2 transactivation domain are substituted with an aspartic or glutamic acid residue. In yet another embodiment, a method of the invention is practiced by introducing into a muscle cell a MEF2 activator such as a p38α-encoding nucleic acid molecule in order to induce the p38 mitogen-activated protein kinase/myocyte enhancer factor 2 (MEF2) pathway in the neuron.

A method of the invention for protecting a muscle cell from cell death also can be practiced by inducing the p38/MEF2 pathway and further introducing a caspase inhibitor into the muscle cell. It is understood that the caspase inhibitor can be administered together with, prior to, or following induction of the p38/MEF2 pathway. In one embodiment, a muscle cell is protected from cell death by introducing into the muscle cell a constitutively active MEF2 polypeptide and a caspase inhibitor.

The present invention further provides a method of generating muscle cells from progenitor cells by inducing in the progenitor cells the p38 mitogen-activated protein kinase/myocyte pathway and transplanting the cells into a muscle cell environment, thereby differentiating the progenitor cells to produce a population containing muscle cells. In one embodiment, the progenitor cells are differentiated to produce a cell population containing protected muscle cells. A method of the invention for generating muscle cells can be useful, for example, for generating cardiac muscle following myocardial infarction, congestive heart failure, cardiomyopathy or other injury to heart tissue. Where cardiac muscle is to be generated, the cells can be transplanted into the heart wall, which provides the proper tissue environment for muscle cell differentiation. In one embodiment, a method of the invention for protecting a muscle cell from cell death is practiced by introducing into the muscle cell a nucleic acid molecule encoding a MEF2 polypeptide or an active fragment thereof.

A method of the invention for generating muscle cells can be practiced, for example, by introducing into a progenitor cell a nucleic acid molecule encoding a MEF2 polypeptide or an active fragment thereof. Such a MEF2 polypeptide can be, for example, a human MEF2 polypeptide. In one embodiment, a method of the invention for generating muscle cells is practiced by introducing into a progenitor cell a MEF2C polypeptide or an active fragment thereof, for example, a human MEF2C polypeptide or an active fragment thereof.

In another embodiment, a method of the invention is practiced by introducing into a progenitor cell a nucleic acid molecule encoding a constitutively active MEF2 polypeptide, which can be, for example, a constitutively active form of MEF2A, MEF2B, MEF2C or MEF2D. In a further embodiment, the constitutively active form of the MEF2 polypeptide is resistant to caspase cleavage. In yet a further embodiment, a method of the invention for generating muscle cells is practiced by introducing into a progenitor cell a constitutively active MEF2 polypeptide in which the native MEF2 activation domain is replaced with a heterologous activation domain. Exemplary constitutively active MEF2 polypeptides include, for example, MEF2A/VP16, MEF2A/GAL4, MEF2B/VP16, MEF2B/GAL4, MEF2C/VP16, MEF2C/GAL4, MEF2D/VP16 and MEF2D/GAL4 fusion proteins and modified MEF2 polypeptides in which one or all of the p38 kinase phosphorylation sites in the MEF2 transactivation domain are substituted with an aspartic or glutamic acid residue. In yet another embodiment, a method of the invention for generating muscle cells is practiced by introducing into a progenitor cell a MEF2 activator such as a p38α-encoding nucleic acid molecule in order to induce the p38 mitogen-activated protein kinase/myocyte enhancer factor 2 (MEF2) pathway in the neuron.

In a further embodiment, muscle cells are generated by inducing the p38/MEF2 pathway and further introducing a caspase inhibitor into the progenitor cells. It is understood that the caspase inhibitor can be administered together with, prior to, or following induction of the p38/MEF2 pathway. In one embodiment, a muscle cells are generated according to a method of the invention by introducing into the progenitor cells a constitutively active MEF2 polypeptide and a caspase inhibitor.

Further provided by the invention is an isolated progenitor cell which contains an exogenous nucleic acid molecule encoding a MEF2 polypeptide or an active fragment thereof. A progenitor cell of the invention can contain, for example, a nucleic acid molecule encoding a MEF2 polypeptide, or active fragment thereof, operatively linked to a heterologous regulatory element. In one embodiment, the MEF2 polypeptide is a human MEF2 polypeptide or an active fragment thereof. In another embodiment, the MEF2 polypeptide is a MEF2C polypeptide or an active fragment thereof. In further embodiments, the MEF2 polypeptide is a constitutively active MEF2 polypeptide, which can be, for example, a constitutively MEF2A, MEF2B, MEF2C or MEF2D polypeptide and further can be, for example, a constitutively active MEF2 polypeptide in which the native MEF2 activation domain is replaced with a heterologous activation domain. In yet a further embodiment, a constitutively active MEF2 polypeptide is resistant to caspase cleavage. A constitutively active MEF2 polypeptide useful in a progenitor cell of the invention can be, for example, a MEF2A/VP16, MEF2A/GAL4, MEF2B/VP16, MEF2B/GAL4, MEF2C/VP16, MEF2C/GAL4, MEF2D/VP16 or MEF2D/GAL4 fusion protein. A constitutively active MEF2 polypeptide also can be a modified MEF2 polypeptide in which one or all of the p38 kinase phosphorylation sites in the MEF2 transactivation domain are substituted with an aspartic or glutamic acid residue.

A progenitor cell useful in the invention can be a human progenitor cell such as a human stem cell and, if desired, can be a CD133-positive human progenitor cell. Progenitor cells useful in the invention can be selected such that they are enriched for specific markers. Human progenitor cells useful in the invention include, for example, CD133-positive human progenitor cells; CD133-positive/CD34-positive human progenitor cells; CD133-positive/CD34-negative human progenitor cells; CD133-positive/CD34-negative/CD45-negative; CD34-negative/CD38-negative/Lin-negative human progenitor cells; and CD34-positive/CD38-negative/Lin-negative/Thy-1-negative human progenitor cells.

Progenitor cells useful in the invention include stem cells, which can be, for example, embryonic stem cells such as human embryonic stem cells. Progenitor cells useful in the invention also can be, for example, human hematopoietic progenitor cells including the most undifferentiated, pluripotent hematopoietic progenitor cells, which can be denoted "hematopoietic stem cells." In one embodiment, a progenitor cell of the invention is a human progenitor cell such as a CD133-positive/CD34-negative/Lin-negative human progenitor cell containing an exogenous nucleic acid molecule encoding a human MEF2C polypeptide or active fragment thereof. In still further embodiments, a progenitor cell of the invention is a human progenitor cell such as a CD133-positive/CD34-negative/Lin-negative human progenitor cell that contains an exogenous nucleic acid molecule encoding a constitutively active MEF2 polypeptide or an active fragment thereof.

As used herein, the term "stem cell" means a pluripotent cell type which can differentiate under the appropriate conditions to give rise to all cellular lineages. Thus, a stem cell differentiates to neuronal cells, hematopoietic cells, muscle cells, adipose cells, germ cells and all other cellular lineages. A stem cell can be an embryonic stem cell. Where the term "hematopoietic stem cell" is used, it is understood that this term refers to cells that are committed to the hematopoietic lineage but which can differentiate to all cells of the hematopoietic lineage.

As used herein, the term "embryonic stem cell" is synonymous with "ES cell" and means a pluripotent cell type derived from an embryo which can differentiate to give rise to all cellular lineages. Examples of cell markers that indicate a human embryonic stem cell include the Oct-4 transcription factor, alkaline phosphatase, SSEA-4, TRA 1-60, and GCTM-2 epitope as described in Reubinoff et al., supra, 2000. Examples of cell markers that indicate a differentiated neuronal cell including neurofilament proteins, β-tubulin, Map2a+b, synaptophysin, glutamic acid decarboxylase, Tun, SNAP 25, transcription factor Brn-3, and GABAa a2 receptor subunit as described in Reubinoff et al., *Nat. Biotech.* 18:399-404 (2000); Ghosh and Greenberg, *Neuron* 15:89-103 (1995); Bain et al., *Devel. Biol.* 168:342-357 (1995); and Williams et al., *Neuron* 18:553-562 (1997).

The methods of the invention also can be used to differentiate progenitor cells in the same manner as the disclosed methods for differentiating stem cells. As used herein, the term "progenitor cells" means any cells that are capable of differentiating into the desired cell type such as a neuronal cell under the appropriate conditions. Progenitor cells can be multipotent or unipotent and can be stem cells, precursor cells, primary cells or established cells. Progenitor cells such as stem cells generally are distinct from neurons in that they lack neuronal markers such as the nuclear protein NeuN, neurofilament and microtubule-associated protein 2 (MAP2) as well as the neuronal-like processes characteristic of mature neurons. In one embodiment, progenitor cells are cells other than P19 embryonic carcinoma cells, which are cells from an established cell line that differentiates to neurons when treated with retinoic acid and to myocytes when treated with dimethylsulfoxide. In another embodiment, progenitor cells are primary cells, which is a well known term in the art for cells which are derived directly from an organism and which have limited growth capacity in culture.

A progenitor cell useful in the invention can be multipotent or unipotent. As used herein in reference to a progenitor cell, the term "multipotent" is synonymous with "pluripotent" and means a progenitor cell capable of differentiating into two or more distinct lineages, including the neuronal lineage. Multipotent progenitor cells such as stem cells, which are generally nestin-positive cells, are distinguished from unipotent precursor cells, which are generally Hu-positive cells. Expression of nestin and Hu can be determined, for example, by immunocytochemistry as disclosed in Example II. A multipotent progenitor cell is capable of differentiating into at least three or more, four or more, or five or more distinct lineages, including the neuronal lineage.

The methods of the invention are useful for differentiating progenitor cells to produce a population containing protected neuronal cells. As used herein, the term "neuronal cell" means a nerve cell and is characterized, in part, by containing one or more markers of neuronal differentiation. Such a marker can be, for example, neurofilament, NeuN or MAP2. A neuronal cell further generally is characterized as containing neuronal-like processes as shown in FIG. 6F.

The results disclosed herein indicate that the p38α/MEF2 cascade protects differentiating cells from death during neurogenesis. Thus, the methods of the invention rely, in part, on inducing the p38 mitogen-activated protein kinase/myocyte enhancer factor 2 (p38 MAP kinase/MEF2) pathway in a progenitor cell. The p38 MAP kinase/MEF2 pathway can be induced by any of a variety of means that result in an increase in MEF2A, MEF2B, MEF2C or MEF2D expression or activity. For example, a MEF2 polypeptide can be phosphorylated and activated, thereby inducing the p38 MAP kinase/MEF2 pathway. p38α, for example, is a known activator, and, therefore, transfection of a p38α encoding nucleic acid molecule or treatment with an agent that increases p38α expression or activity can be used to induce the p38 MAP kinase/MEF2 pathway in a method of the invention (see Example VIII). Thus, transcription factors that increase transcription of a MEF2 polypeptide or p38α; kinases or other proteins that activate a MEF2 polypeptide; or upstream effectors such as PAK-y can be used to induce the p38 MAP kinase/MEF2 pathway. One can readily assay for induction of the p38 MAP kinase/MEF2 pathway by assaying for MEF2 binding activity and transcriptional activity dependent on the presence of the MEF2 binding site.

Induction of the p38 MAP kinase/MEF2 pathway also can be achieved using a MEF2 activator, which is a small molecule that results in increased expression or activity of a MEF2 polypeptide or which is a mimetic or MEF2 function. A MEF2 activator can result in increased expression or activity of one or more MEF2 polypeptides, for example, may result in increased expression or activity of MEF2C without effecting expression or activity of MEF2A, MEF2B or MEF2D. Such a MEF2 activator can be an organic chemical, drug, nucleic acid molecule, peptide, peptidomimetic, polypeptide or other naturally or non-naturally occurring organic molecule, and can be, for example, a MEF2 mimetic. Exemplary MEF2 activators are transcription factors that upregulate MEF2 expression, molecules that compete for binding to a MEF2 inhibitor such as Cabin 1 or histone deacetylase, and kinases that activate MEF2 polypeptides such as p38α. It is understood that a MEF2 activator can be useful in any of the methods of the invention in which the p38 mitogen-activated protein kinase/myocyte enhancer factor 2 (MEF2) pathway is induced. Thus, a MEF2 activator can be useful, for example, in differentiating progenitor cells to produce a cell population containing protected neuronal cells, in reducing the severity of a neurologic condition, in protecting a neuron or muscle cell from cell death, or in generating muscle cells.

MEF2 is normally sequestered in a transcriptionally inactive state by Cabin1 (Youn et al., *Science* 286:790793 (1999)). Thus, a MEF2 activator can be a factor that decreases expression of Cabin1 or a factor that promotes dissociation of MEF2 from Cabin1. Such a factor can be, for example, a fragment of Cabin1 or a fragment of MEF2 that competes for Cabin1 binding to MEF2, thereby dissociating MEF2 from Cabin1 and increasing the amount of active endogenous MEF2. Such MEF2 activators can be identified by preparing and screening fragments of Cabin1 and MEF2 using routine methods.

MEF2 also is post-translationally regulated by class II histone deacetylases, which bind the DNA-binding domain of MEF2 polypeptides (Lu et al., *PNAS* 97:4070-4075 (2000)). MEF2 activity can be maximally stimulated only when repression by histone deacetylases is relieved, for example, by calmodulin-dependent protein kinase signalling to the DNA-binding domain. Thus, a MEF2 activator can be a factor that decreases histone deacetylase expression or that promotes dissociation of MEF2 from histone deacetylase. Such a MEF2 activator can be, for example, a fragment of histone deacetylase or a fragment of MEF2 that competes for binding of MEF2 to histone deacetylase, thereby dissociating histone deacetylase and increasing the amount of active MEF2 polypeptide. Such a MEF2 activator can be identified by preparing and screening fragments of histone deacetylase and MEF2 using routine methods.

An increase in either the p38α kinase or the big MAP kinase (Bmk1), also known as ERK5 kinase, increases MEF2 activity. Therefore, a MEF2 activator can be a molecule that increases the expression or activity of p38α kinase, for example, a nucleic acid molecule encoding p38α (Matsumoto et al., *J. Biol. Chem.* 274:13954-13960 (1999)). Similarly, a MEF2 activator also can be a molecule that increases the expression or activity of Bmk1/ERK5, for example, a nucleic acid molecule encoding Bmk1/ERK5 (English et al., *Journal of Biological Chemistry* 274:31588-31592 (1999); Kato et al., *Nature* 395:713-716 (1998)).

In one embodiment, the p38 MAP kinase/MEF2 pathway is induced by introducing a nucleic acid molecule encoding a MEF2 polypeptide into a progenitor cell under conditions suitable for expression of the MEF2 polypeptide in the cell. MEF2 polypeptides, which occur in a variety of isoforms and alternatively spliced forms, are characterized, in part, as belonging to the MADS-box family of transcriptional regulators. The MADS-box is a 57 amino acid motif located at the extreme N-terminus of MEF2 polypeptides (FIG. 1A). This motif serves as a minimal DNA-binding domain and, in conjunction with an adjacent 29-amino acid extension designated the MEF2 domain, confers high-affinity DNA binding and dimerization (Molkentin et al., *Mol. Cell. Biol.* 16:2627-36 (1996). Within the MADS-box, MEF2 polypeptides share homology at several invariant residues with other members of the MADS-box family of transcription factors, including serum response factor (SRF). These conserved residues are important for DNA sequence recognition. While the MEF2 domain is unique to MEF2 factors, other MADS-box proteins contain domains with analogous functions. In addition to its role in DNA binding, the MADS-box mediates dimerization of MADS-box proteins, and the MEF2 domain is important for interactions with accessory factors. MEF2 polypeptides can homo- and heterodimerize but cannot interact with other MADS-box factors, indicating that specific residues within the MADS-box that establish the dimerization interface are not conserved outside the MEF2 family.

Vertebrate MEF2 polypeptides share about 50% amino acid identity overall and about 95% similarity throughout the highly conserved MADS-box and MEF2 domain, whereas they are divergent in their C-terminal regions. MEF2 polypeptides from invertebrates also are highly homologous to vertebrate MEF2 polypeptides in the MADS-box and MEF2 domain. The *Drosophila* MEF2 polypeptide, D-MEF2, binds the same DNA sequence as its vertebrate' counterparts and can activate transcription through the MEF2 site in mammalian cells (Lilly et al., *Proc. Natl. Acad. Sci. USA* 91:5662-66 (1994) and Nguyen et al., *Proc. Natl. Acad. Sci. USA* 91:7520-24 (1994)).

MEF2 polypeptides, like other MADS-box proteins, bind an A/T-rich DNA sequence. The consensus MEF2 binding site is YTA(A/T)$_4$TAR (SEQ ID NO:25). MEF2A, MEF2C and MEF2D have the same DNA binding specificity, whereas MEF2B binds the MEF2 consensus sequence with reduced affinity compared to other family members. Nucleotides flanking the MEF2 site have been shown to profoundly influence DNA binding (Yu et al., *Genes Dev.* 6:1783-98 (1992); Andres et al., *J. Biol. Chem.* 270:23246-49 (1995); and Fickett *Mol. Cell. Biol.* 16:437-41 (1996)). Evidence suggests that the DNA binding site is bent upon high affinity DNA binding (Meierhans et al., *Nucleic Acids Res.* 25:4537-44 (1997)).

Figure 1B:
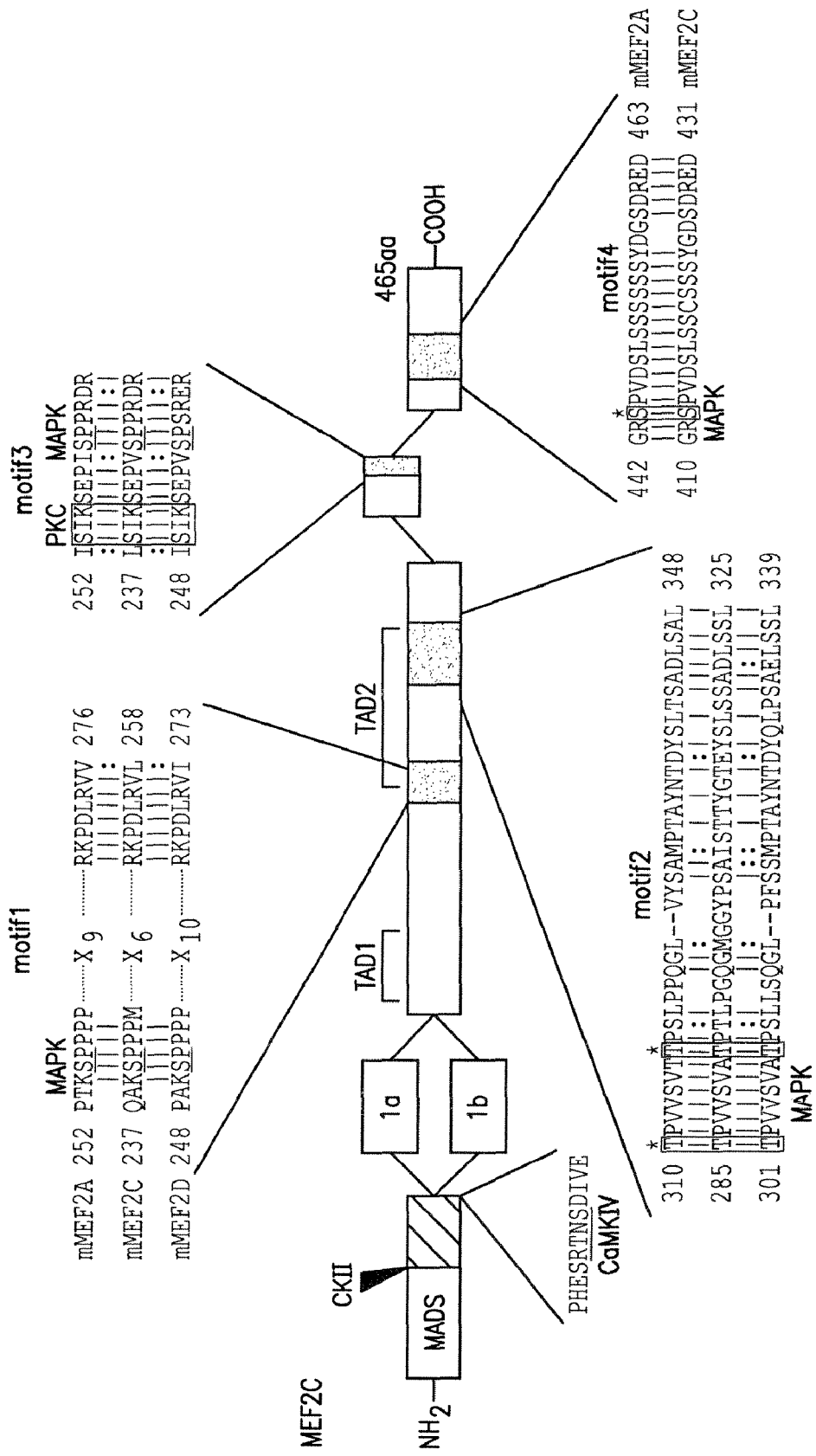
FIG. 1B shows conserved regions in the C terminus of MEF2 contain potential phosphorylation sites. MEF2A motifs 1 to 4 are shown as SEQ ID NOS: 13 to 16, respectively. MEF2C motifs 1 to 4 are shown as SEQ ID NOS: 17 to 20, respectively. MEF2D motifs 1 to 3 are shown as SEQ ID NOS: 21 to 23, respectively. Sites that are phosphorylated by p38 and ERK5 are marked with asterisks. Not all potential phosphorylation sites are shown. Some of the conserved stretches overlap with transactivation domains that have been mapped by deletion analysis. PKC, protein kinase C site: MAPK, mitogen-activated protein kinase site; CKII casein kinase II site. CaMKIV, calcium-calmodulin kinase IV site. MEF2A motifs 1 to 4 are shown as SEQ ID NOS: 13 to 16, respectively. MEF2C motifs 1 to 4 are shown as SEQ ID NOS: 17 to 20, respectively. MEF2D motifs 1 to 3 are shown as SEQ ID NOS: 21 to 23, respectively.

While the MADS-box and MEF2 domain are necessary and sufficient for DNA binding, they lack transcriptional activity on their own. The C-terminal regions of MEF2 polypeptides contain transcriptional activation domains and are subject to alternative splicing (FIG. 1A), with some exons present ubiquitously and others muscle- or neural-specific. In MEF2A, an acidic exon with the sequence SEEEELEL (SEQ ID NO: 9) is specific to muscle and neural cells in which MEF2 DNA-binding activity is detected and is absent in MEF2 transcripts from a variety of cell types in which MEF2A protein is not detected (Yu et al., *Genes Dev.* 6:1783-98 (1992)). MEF2D contains a similar acidic exon (TEDHLDL; SEQ ID NO: 10), which is present only in transcripts from skeletal muscle, heart, and brain, and correlates with MEF2D-binding activity (Breitbart et al., *Development* 118:1095-106 (1993) and Martin et al., *Mol. Cell. Biol.* 14:1647-56 (1994)). The corresponding domain in MEF2C (SEDVDLLL; SEQ ID NO: 11) is present in transcripts from skeletal muscle only (McDermott et al., *Mol. Cell. Biol.* 13:2564-77 (1993)). Although the inclusion of these exons is not essential for DNA binding activity, their presence appears to correlate with high levels of MEF2 DNA-binding activity. There is relatively little amino acid homology between the C-terminal regions of different MEF2 polypeptides, except for the short acidic exons described above and four serine/threonine-rich regions (FIG. 1B).

As used herein, the term "MEF2 polypeptide" means a polypeptide that has MEF2 DNA binding activity in addition to activity as a transcriptional activator and includes polypeptides having substantially the amino acid sequence of MEF2A, MEF2B, MEF2C or MEF2D. Thus, a MEF2 polypeptide can have, for example, substantially the amino acid sequence of human MEF2A (SEQ ID NO: 2) shown in FIG. 2, human MEF2B (SEQ ID NO: 4) shown in FIG. 3; human MEF2C (SEQ ID NO: 6) shown in FIG. 4, or human MEF2D (SEQ ID NO: 8) shown in FIG. 5. A MEF2 polypeptide includes a MADS domain, a MEF2 domain and a transcriptional activation domain. It is understood that, while the MADS domain and MEF2 domains of a MEF2 polypeptide will be similar in structure to the MADS domain and MEF2 domain of a naturally occurring MEF2 polypeptide such as human MEF2C (SEQ ID NO: 6), the transcriptional activation domain of a MEF2 polypeptide may be structurally unrelated and can be, for example, a synthetic transcriptional activation or a heterologous transcriptional activation domain derived, for example, from VP16 or GAL4. One skilled in the art appreciates that a fragment of a MEF2 polypeptide that retains MEF2 DNA binding activity and transcriptional activity also can be useful in the methods and compositions of the invention.

The term MEF2 polypeptide encompasses a polypeptide having the sequence of a naturally occurring human MEF2A polypeptide (SEQ ID NO:2), naturally occurring human MEF2B polypeptide (SEQ ID NO: 4), naturally occurring human MEF2C polypeptide (SEQ ID NO: 6) or naturally occurring human MEF2D polypeptide (SEQ ID NO: 8) and is intended to include related polypeptides having substantial amino acid sequence similarity to SEQ ID NOS: 2, 4, 6 or 8. Such related polypeptides typically exhibit greater sequence similarity to hMEF2A, hMEF2B, hMEF2C or hMEF2D than to other MADS box proteins such as serum response factor (SRF) and include species homologs such as primate, mouse, rat and *D. rerio* homologs, alternatively spliced forms, and isotype variants of the proteins shown in FIGS. 2 through 5.

As used herein, the term MEF2 polypeptide describes polypeptides generally including an amino acid region with greater than about 60% amino acid sequence identity in the combined MADS and MEF2 domains with hMEF2A (SEQ ID NO: 2), hMEF2B (SEQ ID NO: 4), hMEF2C (SEQ ID NO: 6) or hMEF2D (SEQ ID NO: 8). In particular, a MEF2 polypeptide can have greater than about 65% amino acid identity, preferably greater than about 70% amino acid identity, more preferably greater than about 75% amino acid identity, still more preferably greater than about 80% amino acid identity and most preferably greater than about 85%, 90% or 95% amino acid identity with the combined MADS and MEF2 domains of SEQ ID NOS: 2, 4, 6 or 8.

As used herein, the term "substantially the amino acid sequence," when used in reference to a MEF2 polypeptide or fragment thereof, is intended to mean a polypeptide or fragment having an identical amino acid sequence, or a polypeptide, fragment or segment having a similar, non-identical sequence that is considered by those skilled in the art to be a functionally equivalent amino acid sequence. For example, polypeptide including substantially the same amino acid sequence as human MEF2C (SEQ ID NO: 6) can have an amino acid sequence identical to the sequence of human MEF2C (SEQ ID NO:6) shown in FIG. 4, or a similar, non-identical sequence that is functionally equivalent. An amino acid sequence that is "substantially the amino acid sequence" can have one or more modifications such as amino acid additions or substitutions relative to the amino acid sequence shown, provided that the modified polypeptide retains the ability to bind the MEF2 binding site and to activate transcription.

Therefore, it is understood that limited modifications can be made without destroying the biological function of a MEF2 polypeptide or fragment useful in the invention. For example, minor modifications of hMEF2C (SEQ ID NO: 6) that do not destroy polypeptide activity also fall within the definition of a MEF2 polypeptide. Similarly, minor modifications of human MEF2A, -B, -C or -D that do not destroy polypeptide activity fall within the definition of a MEF2 polypeptide. Also, for example, genetically engineered fusion proteins that retain the DNA binding and transcriptional activation activity of a MEF2 polypeptide fall within the meaning of the term "MEF2 polypeptide" as used herein.

It is understood that minor modifications of primary amino acid sequence can result in polypeptides which have substantially equivalent or enhanced function as compared to the MEF2 polypeptides shown in FIGS. 2 through 5. These modifications can be deliberate, as through site-directed mutagenesis, or can be accidental such as through mutation in hosts harboring an encoding nucleic acid. All such modified polypeptides are included in the definition of a MEF2 polypeptide as long as MEF2 DNA binding activity and transcriptional activation activity are retained. Further, various molecules can be attached to a MEF2 polypeptide, for example, other polypeptides, carbohydrates, lipids, or chemical moieties. Such modifications are included within the definition of each of the polypeptides of the invention.

While native MEF2 polypeptides are activated through phosphorylation, for example, by p38 MAP kinase, constitutively active forms of MEF2 do not require such phosphorylation for activation. Any of the methods of the invention can be practiced using a constitutively active MEF2 polypeptide to induce the p38/MEF2 pathway.

As used herein in reference to a MEF2 polypeptide, the term "constitutively active" means a MEF2 polypeptide that has transactivation activity which is less dependent upon phosphorylation than the corresponding wild type MEF2 polypeptide. A constitutively active MEF2 polypeptide can have transactivation activity that is independent of phosphorylation. As disclosed herein, a MEF2 polypeptide can be cleaved by a caspase to produce a dominant negative form of a MEF2 polypeptide having pro-apoptotic activity. In one embodiment, a constitutively active form of a MEF2 polypeptide is resistant to caspase cleavage.

A constitutively active MEF2 polypeptide can include, for example, a heterologous transactivation domain in addition to, or in place of, the native MEF2 transactivation domain. A constitutively active MEF2 polypeptide can be, for example, a MEF2A, MEF2B, MEF2C or MEF2D polypeptide containing a GAL4 or VP16 transactivation domain in addition to, or in place of, the native MEF2 transactivation domain. In specific embodiments, a constitutively active MEF2 polypeptide is a chimera in which the native MEF2 activation domain is replaced with a heterologous activation domain, for example, a constitutively active MEF2A/VP16, MEF2A/GAL4, MEF2B/VP16, MEF2B/GAL4, MEF2C/VP16, MEF2C/GAL4, MEF2D/VP16 or MEF2D/GAL4 fusion protein.

A constitutively active MEF2 polypeptide also can be a MEF2 polypeptide in which the native activation domain is modified such that transactivation does not depend on phosphorylation. A constitutively active MEF2 polypeptide can have, for example, one or modified phosphorylation sites within the transactivation domain, for example, one or more serine/threonine to aspartic acid/glutamic acid amino acid substitutions within the transactivation domain. See, for example, Watson et al., *J. Neurosci.* 18:751-762 (1998), which demonstrates that mutation of the Jun kinase phosphorylation site in c-Jun to aspartic acid produces a constitutively active c-Jun polypeptide that is independent of Jun kinase.

MEF2A is phosphorylated at Thr312, Thr319 and Ser453 within the transactivation domain, and MEF2C is phosphorylated at Thr293, Thr300 and Ser387 within the transactivation domain (Han et al., *Nature* 386:296-299 (1997); and Zhao et al., *Mol. Cell. Biol.* 19:21-30 (1999)). Thus, a constitutively active human MEF2A polypeptide can contain, for example, one or more amino acid substitutions such that one or all of Thr312, Thr319 and Ser453 are replaced with aspartic or glutamic acid. In addition, a constitutively active human MEF2C polypeptide can contain, for example, one or more amino acid substitutions such that one or all of Thr293, Thr300 and Ser387 are replaced with aspartic or glutamic acid. It is understood that analogous phosphorylation sites in MEF2B and MEF2D and other species homologs of MEF2A and MEF2C can be similarly modified to produce a constitutively active MEF2 polypeptide.

A variety of routine assays can be used to confirm constitutive activity of a MEF2 polypeptide including cotransfection assays using cerebrocorticol neurons, where constitutive activity is indicated by reporter activity significantly greater than wild type MEF2 transcriptional activity. For example, cerebrocorticol neurons can be cultured for about five hours using Lipofectamine-2000 with the MEF2 expression vector and a luciferase reporter vector such as pGL2MEF2LUC, and luciferase activity determined by standard means.

As stated above, a MEF2 polypeptide can be cleaved by a caspase to produce a dominant negative form of a MEF2 polypeptide having pro-apoptotic activity. Thus, in the presence of an activated caspase, protective MEF2 activity can be enhanced by a caspase inhibitor. Thus, in one embodiment of the invention, induction of the p38 mitogen-activated protein kinase/myocyte enhancer factor 2 (MEF2) pathway is combined with treatment of the cell by a caspase inhibitor.

A variety of caspase inhibitors are useful in the invention including, for example, nucleic acids, polypeptides, peptides, peptidomimetics and non-peptide inhibitors such as small molecule drugs known in the art. As used herein, the term "caspase inhibitor" means any molecule that binds to and inhibits the activity of one or more caspases. Caspase inhibitors useful in the methods of the invention generally are cell permeable and have inhibitory activity in vivo and include viral and cellular gene products as well as synthetic inhibitors such as synthetic small molecules (Ekert et al., *Cell Death and Differentiation* 6:1081-1086 (1999)).

Such a caspase inhibitor can be a general, or non-selective, caspase inhibitor as well as a selective inhibitor. Selective inhibitors do not inhibit non-caspase cysteine proteases or serine proteases. Non-selective caspase inhibitors, which also inhibit one or more non-caspase protease inhibitors, include, for example, the cysteine protease inhibitor iodoacetamide. A caspase inhibitor also can be selective for one or more specific caspases. A caspase inhibitor can selectively inhibit caspase-3 or caspase-7 or a combination thereof and can be combined, for example, with a nucleic acid molecule encoding a MEF2C polypeptide, or an active fragment thereof. An exemplary caspase inhibitor which is selective for caspases-3 and -7 is a non-peptide inhibitor such as a isatin sulfonamide (see, for example Lee et al., *J. Biol. Chem.* 275:16007-16014 (2000)). A selective caspase inhibitor also can be selective for caspase-3, caspase-6, caspase-7 or caspase-8, or any combination thereof, and can be combined, for example, with a nucleic acid molecule encoding a MEF2A polypeptide, or an active fragment thereof.

A caspase inhibitor can be, for example, the cytokine response modifier A (CrmA) polypeptide, or an encoding nucleic acid molecule, which inhibits caspases 1 and -8; or the p35 baculovirus protein, or an encoding nucleic acid molecule, which inhibits caspases-1, -3, -6-7, -8 and -10 but does not inhibit non-caspase cysteine proteases or serine proteases (Clem et al., *Science* 254:1388-1390 (1991)). A caspase inhibitor also can be an inhibitor of apoptosis protein (IAP) or an encoding nucleic acid molecule. IAPs useful as caspase inhibitors in a method of the invention include XIAP and Survivin, which inhibit caspases-3 and -7.

A caspase inhibitor also can be a synthetic caspase inhibitor such as a pseudosubstrate which acts a reversible or irreversible competitive inhibitors of caspases. Active site mimetic peptide ketones are useful, for example, as selective caspase inhibitors. Such caspase inhibitors include, for example, benzylcarbonyl (z)-VAD-fluoromethylketone (fmk), z-VAD-fmk/chloromethylketone (CMK), z-DEVD-fmk/cmk; and z-D-cmk. Additional caspase inhibitors include the halomethyl ketone-linked peptide YVAD, Ac-WEHD-CHO, Ac-DEVD-CHO, Ac-YVAD-CHO, t-butoxycarbonyl-IETD-CHO, and t-butoxycarbonyl-AEVD-CHO (Ekert et al., supra, 1999). The skilled person understands that these and other caspase inhibitors can be useful in the invention. See, for example, Nicholson, *Nature* 407:810-816 (2000), WO 00/55114, and Garcia-Calvo et al., *J. Biol. Chem.* 273:32608-32613 (1998)).

As used herein in reference to a neuronal cell, the term "protected" means a cell that is induced to undergo neurogenesis and is more resistant to apoptotic cell death than a cell in which the p38 MAP kinase/MEF2 pathway is not induced, or is induced to a lesser extent. Thus, a population containing protected neuronal cells will exhibit less apoptosis than a population that does not contain "protected" neuronal cells.

The percentage of apoptotic cells in a population can be determined by a variety of assays well known in the art. Such methods include light microscopy for determining the presence of one or more morphological characteristics of apoptosis, such as condensed or rounded morphology, shrinking and blebbing of the cytoplasm, preservation of structure of cellular organelles including mitochondria, and condensation and margination of chromatin. The percentage of apoptotic cells also can be determined by assaying apoptotic activity using terminal deoxytransferase-mediated (TdT) dUTP biotin nick end-labeling (TUNEL) (Gavriel et al., *J. Cell Biol.* 119:493 (1992); Gorczyca et al., *Int. J. Oncol.* 1:639 (1992); Studzinski (Ed.), *Cell Growth and Apoptosis*. Oxford: Oxford University Press (1995)). ApopTag™ (ONCOR, Inc., Gaithersburg, Md.) is a commercially available kit for identification of apoptotic cells using digoxygenin labeling. In addition, apoptotic cells can be identified by detecting characteristic nucleosomal DNA fragments using agarose gel electrophoresis (Studzinski, supra, 1995; Gong et al., *Anal. Biochem.* 218:314 (1994)) or using DNA filter elution methodology to detect apoptosis-associated DNA fragmentation (Bertrand et al., *Drug Devel.* 34:138 (1995)). One skilled in the art understands that these, or other assays for apoptosis, can be performed using methodology routine in the art.

In the methods of the invention, progenitor cells are contacted with a differentiating agent. In one embodiment, the differentiating agent is retinoic acid, for example, all trans-retinoic acid. In another embodiment, the differentiating agent is neurotrophic factor 3, epidermal growth factor, insulin-like growth factor 1 or a platelet-derived growth factor.

As used herein, the term "differentiating agent" means a naturally occurring or synthetic cytokine, growth factor or other compound that causes or enhances a progenitor cell to have one or more characteristics of a neuronal cell. A differentiating agent useful in the invention can be, for example, retinoic acid such as all-trans retinoic acid; neurotrophic factor 3 (NT3); epidermal growth factor (EGF); insulin-like growth factor-1 (IGF-1); platelet derived growth factor (PDGF), or a combination of two or more of these factors. For example, EGF, IGF-1 and PDGF can be used together as a differentiating agent. Basic fibroblast growth factor (bFGF) or another factor that enhances proliferation of precursor cells can optionally be used prior to treating with a differentiating agent such as EGF, IGF-1 and PDGF. One skilled in the art understands that one or more factors such as brain-derived neurotrophic factor (BDNF) also can be added to promote neuronal cell survival.

For use in the methods or compositions of the invention, embryonic stem cells can be obtained from a variety of mammals including, for example, mice, cows, primates and humans by methods well known in the art. For example, murine embryonic cells can be isolated from a mouse as described in Forrester et al., *Proc. Natl. Acad. Sci. USA* 88:7514-7517 (1991) or Bain et al., *Devel. Biol.* 168:342-357 (1995). Briefly, two-stage cell embryos can be isolated from fertilized female mice about 45 hours after injection with human chorionic gonadotropin. The two blastomeres can be fused by electrical impulse and cultured in M16 medium until the four cell stage is reached. ES cells can be grown on gelatin coated tissue culture flasks in DMEM (Dulbeco's modified Eagle's medium) containing high glucose and 1-glutamine (BRL) supplemented with 10% fetal bovine serum, 10% newborn calf serum, nucleosides stock, 1000 units/ml leukemia inhibitory factor, and 0.1 mM 2-mercaptoethanol.

Embryonic stem cells can be isolated from primates as described in Thomson (U.S. Pat. No. 5,843,780). Briefly, blastocysts can be removed from fertilized female monkeys 6-8 days after onset of ovulation, treated with pronase (Sigma) to remove the zona pellucida, rabbit anti-rhesus monkey spleen cell antiserum (for blastocysts from rhesus monkeys) and guinea pig complement (Gibco BRL), and washed in DMEM. The inner cell mass (ICM) can be removed from the lysed blastocyst with a pipette and plated on mouse gamma radiation inactivated embryonic fibroblasts. After 7 to 21 days the ICM derived masses can be removed with a micropipette, treated with 0.05% trypsin-EDTA (Gibco BRL) and 1% chicken serum, and replated on embryonic feeder cells. Colonies demonstrating ES morphology, characterized by compact colonies with a high nucleus to cytoplasm ratio and prominent nucleoli, can then be split as described above. The ES cells can be split by trypsinization or exposure to Dulbeco's phosphate buffered saline containing 2 mM EDTA every 1-2 weeks when cultures become dense.

Embryonic stem-like cells also can be isolated from cows as described in Cibelli et al., *Nat. Biotech.* 16:642-646 (1998). Briefly, oocytes can be removed from freshly slaughtered cows and placed in maturation medium M199 (Gibco), 10% fetal calf serum (PCS), 5 ug/ml bovine leutinizing hormone (Nob1) and 10 ug/ml pen-strep (Sigma) for 22 hours at 38.5° C. Oocytes can then be fertilized in vitro and cultured on mouse embryonic fibroblast feeder layers and CR2 with 6 mg/ml BSA until they reach the blastocyst stage. ES cells can be isolated from the blastocyst by mechanical removal of the zona pellucida and trophoblast with a 22 gauge needle and placed under mouse embryonic fibroblast feeder layers for one week. A small colony of the resulting cell mass can be removed and cultured on top of gamma irradiation inactivated mouse embryonic fibroblast feeder layer as cultures become dense.

Embryonic stem cells can be isolated from human blastocysts as described in Reubinoff et al., *Nat. Biotech.* 18:399-404 (2000). Briefly, fertilized oocytes can be cultured to the blastocyst stage and the zona pellucida digested by pronase (Sigma). The inner cell mass can be removed by immunosurgery with anti-human serum antibody (Sigma) and exposure to Guinea pig complement (BRL), and cultured on a mitomycin C mitotically inactivated mouse embryonic feeder cell layer in DMEM (BRL) supplemented with 20% fetal bovine serum (FBS, Hyclone) 0.1 mM 2-mercaptoethanol, 1% non essential amino acids, 2 mM glutamine, 50 units/ml penicillin and 50 ug/ml streptomycin (BRL) and 2,000 units/ml recombinant leukemia inhibitory factor. Cell mass clumps can be removed with a micropipette and replated on fresh feeder layer every six to eight days.

Human stem cells can be obtained, for example, from cord blood, which is highly enriched in primitive cells and contains a CD133-positive/CD34-positive population. These cells can be efficiently isolated by methods well known in the art, for example, the Miltiny1 MACS system. If desired, the CD133-positive/CD34-positive population can be expanded by culturing in vitro with Flt3L+TPO to produce as much as an 160-fold expansion in long-term culture potential and a $2 \times 10^6$ fold expansion in the number of progenitor cells.

Human progenitor cells useful in the invention include human embryonic stem cells, human hematopoietic stem cells and other progenitor cells isolated from adult human blood or from cord blood of newborn infants. In one embodiment of the invention, the progenitor cell population is enriched in CD133 (AC133)-positive/CD34-positive progenitor cells. In a further embodiment of the invention, the progenitor cell population is enriched in CD133-positive/CD34-negative progenitor cells. Such specific progenitor cell populations can be isolated, for example, with magnetic-activated cell sorting, fluorescence-activated cell sorting (FACS), or related methods well known in the art as described further below. It further is understood that in vitro expansion of progenitor or stem cells such as human progenitor or stem cells can be performed, if desired, with one or more of the following factors: SCF, IL-3, IL-6, flt3L, LIF, IL-11, TGF-(3, TPO, EGF and bFGF, which are commercially available, for example, from Biosource (Camarillo, Calif.), R&D Systems (Minneapolis, Minn.) and Chemicon (Temecula, Calif.). Various protocols for expansion and useful concentrations of particular factors are well known in the art.

In one embodiment, human progenitor cells are obtained from peripheral blood. Donors can be treated with recombinant human G-CSF (rhG-CSF), such as Neupogen (Amgen; Thousand Oaks, Calif.), or recombinant human GM-CSF (rhGM-CSF), such as Leukine (Immunex; Seattle, Wash.), or both. In a further embodiment, the human progenitor cells are primitive cells characterized as CD34+, Thy-/dim, CD38–, which can be obtained, if desired, from G-CSF or GM-CSF treated to donors to increase long-term culture potential. In one embodiment, human progenitor cells are CD34+, Thy-/dim, CD38– cells obtained from donors treated with G-CSF in combination with GM-CSF.

Methods well known in the art can be used to collect progenitor cells from human peripheral blood or cord blood. Apheresis can be used to collect white blood cells, for example, four to five days following treatment with G-CSF, GM-CSF or a combination of G-CSF and GM-CSF, generally yielding $4 \times 10^6$ CD34-positive cells/kg of body weight.

A Ceprate SC immunoaffinity column commercially available from Cellpro (Bothell, Wash.) can be used to isolate a CD133-positive progenitor cell population for use in a method of the invention. The desired cell population binds the column matrix via a biotin conjugated antibody linked to the column matrix and is released by mechanical shaking Ceprate SC immunoaffinity can be used to yield about 50% CD34-positive cells with about 16-99% purity.

CD133-positive human progenitor cells also can be isolated, for example, using an Isolex 300 magnetic cell separator (Baxter Healthcare Corporation; Deerfield, Ill.), which relies on mouse monoclonal IgG1 antibodies and magnetic beads coated with anti-mouse IgG1 antibody. Release of the progenitor cells by peptidase treatment yields about 50% CD34-positive cells with 33-100% purity.

Additional art-accepted procedures for isolation of human stem and progenitor cells include the magnetic activated cell sorting system (MACS) commercially available from Miltenyi Biotech (Auburn, Calif.). In this sorting system, small magnetic beads coated with secondary antibody are bound to the primary antibody-treated cells and retained on a ferromagnetic matrix column by a strong magnet. Cells are released by removal of the magnet to give greater than 50% recovery and greater than 90% purity of the desired cells.

Fluorescence-activated cell sorting (FACS) also is a well known method that can be used to isolate the desired progenitor or stem cell population. Using this methodology, cells are selected by attachment of fluorescent-conjugated antibodies to give greater than 90% purity of the recovered stem or progenitor cells.

If desired, isolated stem or progenitor cells can be assayed for the ability to repopulation bone marrow of a sublethally irradiated nonobese diabetic/severe combined immunodeficient (NOD-SCID) mouse, using methods well known in the art, as described, for example, in Miyoshi et al., *Science* 283:682-686 (1999).

In one embodiment, progenitor cells useful in the invention are human CD34-negative bone marrow cells such as CD133-positive/CD34-negative cells. In a further embodiment, the progenitor cells are CD34-negative/Lin-negative cells. Such cells can have characteristics of stromal cells and are capable, for example, of repopulating the bone marrow of NOD/SCID mice following sublethal irradiation. In one embodiment, progenitor cells useful in the invention are CD133-positive/CD34-negative/Lin-negative cells.

Methods of preparing progenitor or stem cell populations enriched for particular markers are well known in the art. For example, a CD133-positive/CD34-positive hematopoietic stem and progenitor cells can be prepared as set forth in Yin et al., *Blood* 90:5002-5012 (1997); CD133-positive/CD34-negative/CD45-negative progenitor cells can be prepared as described, for example, in Uchida et al., *Proc. Natl. Acad. Sci., USA* 97:14720-14725 (2000). In addition, CD34-negative/CD38-negative/Lin-negative human hematopoietic stem cells and CD34-positive/CD38-negative/Lin-negative/Thy-1-negative hematopoietic stem cells can be prepared, for example, as described in Bhatia et al., *Nature Medicine* 4:1038-1045 (1998).

In the methods of the invention, progenitor or stem cells such as embryonic stem cells are contacted with a differentiating agent to induce differentiation of the cells along the neuronal pathway. Methods for differentiating embryonic stem cells by growth of the cells to high density are described in Reubinoff et al., *Nat. Biotech.* 18:399-404 (2000). Methods differentiating expanded CNS cells by initial growth in the presence of a mitogen such as basic fibroblast growth factor (bFGF) followed by removal of bFGF are described in Johe et al. *Genes Develop.* 10:3129-3140 (1996). Induction of neurogenesis by addition of growth factors can be achieved with platelet derived growth factor (PDGF) including for example PDGF-AA, PDGF-AB or PDGF-BB administered in the absence of bFGF as described in Johe et al., supra, 1996. Induction of neuronal differentiation can also be achieved in vitro by removal of fibroblast growth factor-2 and subsequent addition of insulin like growth factor-1, heparin or neurotrophin-3 as described in Brooker et al., *J. Nerosci. Res.* 59:332-341 (2000) and Ghosh and Greenberg, Neuron 15:89-103 (1995); addition of platelet-derived growth factor as described in Williams et al., *Neuron* 18:553-562 (1997); addition of insulin like growth factor-1 alone or in combination with brain derived neurotrophic factor as described in Arsenijevic and Weiss, *J. Neurosci.* 18:2118-2128 (1998); and exposure to retinoic acid as described in Bain et al. *Devel. Biol.* 168:342-357 (1995).

In a preferred embodiment, a nucleic acid molecule encoding a MEF2 polypeptide is introduced into a progenitor cell such as an embryonic stem cell. A variety of methods are known in the art for introducing a nucleic acid molecule into a progenitor cell such as an embryonic stem cell. Such methods include microinjection, electroporation, lipofection, calcium-phosphate mediated transfection, DEAE-Dextran-mediated transfection, polybrene- or polylysine-mediated transfection, and conjugation to an antibody, gramacidin S, artificial viral envelopes or other intracellular carriers such as TAT. For example, embryonic stem cells can be transformed by microinjection as described in Cibelli et al., *Nat. Biotech.* 16:642-646 (1998) or Lamb and Gearhart, *Cur. Opin. Gen. Dev.* 5:342-348 (1995); by lipofection as described in Choi (U.S. Pat. No. 6,069,010) or Lamb and Gearhart, *Cur. Opin. Gen. Dev.* 5:342-348 (1995); by electroporation as described in *Current Protocols in Molecular Biology*, John Wiley and Sons, pp 9.16.4-9.16.11 (2000) or Cibelli et al., *Nat. Biotech.* 16:642-646 (1998); or by fusion with yeast spheroplasts Lamb and Gearhart, *Cur. Opin. Gen. Dev.* 5:342-348 (1995). A MEF2 polypeptide also can be delivered to stem or progenitor cells as a TAT/MEF2 polypeptide fusion by techniques well known in the art as described in Nagahara et al., Nature Medicine 4:1449-1452 (1998).

Viral vectors can be particularly useful for introducing a nucleic acid molecule encoding a MEF2 polypeptide in a method of the invention; such vectors include, for example, retroviral vectors, lentiviral vactors, adenoviral vectors and adeno-associated vectors (AAV), herpesvirus vectors (see, for example, Kaplitt and Loewy, *Viral Vectors: Gene Therapy and Neuroscience Applications* Academic Press, San Diego, Calif. (1995); Chang, *Somatic Gene Therapy* CRC Press, Boca Raton, Fla. (1995)). Lentiviral, retroviral and adeno-associated vectors can be useful, for example, for permanent expression, and adenovirus and herpesvirus can be used to achieve transient expression lasting for several months to about one year. It is understood that both permanent and transient expression can be useful in a method of the invention and in producing a stem or progenitor cell of the invention.

It is understood by those skilled in the art of gene therapy that a progenitor cell also can be engineered to express one or more gene products that are therapeutically useful. For example, for treatment of Parkinson's disease, a progenitor cell such as an embryonic stem cell can express, for example, the catecholamine enzyme tyrosine hydroxylase, thereby increasing dopamine-U-hydroxylase activity upon intracerebral grafting (Jiao et al., *Nature* 362:450 (1993); see, also, Dhawan et al., *Science* 254: 1509 (1991); and Barr and Leiden, *Science* 254:1507 (1991)). Similarly, for treatment of Alzheimer's disease, a progenitor cell can express a nucleic acid molecule encoding nerve growth factor, thereby promoting cell survival of the cholinergic neurons that are typically lost in Alzheimer's disease (Rosenberg et al., *Science* 242: 1575-1578 (1988)). In a similar manner, a progenitor cell can express encephalin for treatment of neuropathic disorders involving intractable pain. One skilled in the art recognizes that these and other combinations are encompassed by the methods of the invention for differentiating progenitor cells to produce a population containing protected neuronal cells.

A progenitor cell such as an ES cell further can be engineered to express one or more anti-apoptotic gene products such as a member of the Bcl-2 family, for example, Bcl-2 (Anderson, *Trends Pharm. Sci.* 18:51 (1997) or Bcl-$X_L$; and Gross and et al., *Genes Dev.* 13:1899-1911 (1999)), or a member of the inhibitor of apoptosis (IAP) family such as c-IAP-1, c-IAP-2, XIAP or NIAP (Deveraux and Reed, *Genes Dev.* 13:239-252 (1999)). A progenitor cell further can be optionally engineered to express a basic helix-loop-helix protein (bHLH), especially a bHLH protein naturally expressed in neuronal cells such as Mash-1, which can functionally interact with a MEF2 polypeptide (Mao and Nadal-Ginard, *J. Biol. Chem.* 271:14371-14375 (1996); Black et al., *J. Biol. Chem.* 271:26659-26663 (1996). A progenitor cell such as an ES cell also can be engineered to express one or more factors that promote differentiation including, for example, neuroD, neuroD2, neuroD3, neurogenin1, neurogenin2, neurogenin3, MATH1 or MATH2 (Lee, *Curr. Opin. Neurobiol.* 7:13-20 (1997)). Such a factor can be expressed instead of or in addition to application of the differentiating agent to the progenitor cell.

Previous methods of producing neuronal cells have suffered from the shortcoming that the populations produced are heterogenous and contain relatively few neurons. A method of the invention is advantageous in that it can be used to produce a population containing protected neuronal cells containing a large proportion of neuronal cells, for example, at least 50% neuronal cells. In other embodiments, the population produced includes at least 55%, 60%, 65%, 70%, 75%, 80%, 85%, 90%, 95% or more neuronal cells. The proportion of neuronal cells can be determined by assaying for one or more characteristic neuronal markers such as the presence of NeuN, neurofilament or MAP2.

A method of the invention for differentiating progenitor cells to produce a population containing protected neuronal cells can optionally include the step of transplanting into a patient cells treated to induce the p38/MEF2 pathway. In a method of the invention, cells can be transplanted, for example, into the brain, eye (retina) or spinal cord after neuronal injury or damage. Thus, cells treated to induce the p38/MEF2 pathway can be transplanted into a patient having or at risk of, for example, stroke or a neurodegenerative disease such as Alzheimer's disease; Huntington's disease; amyotrophic lateral sclerosis; Parkinson's disease; epilepsy; brain or spinal cord trauma; multiple sclerosis; optic neuropathy such as glaucoma; infection of the central nervous system; multiple system atrophy affecting the brain; or another acute or chronic neurodegenerative condition. Upon transplantation, the cells begin to differentiate or continue differentiating to produce a cell population containing protected neuronal cells.

As used herein, the term "patient" means any animal containing neurons, for example, a mammal such as a mouse, rat, dog, primate or human. A patient typically suffers from or is at high risk of developing a neurodegenerative disorder such as Parkinson's disease, Huntington's disease, Alzheimer's disease, amyotrophic lateral sclerosis or multiple sclerosis; hypoxia-ischemia (stroke); epilepsy; head or spinal cord injury; optic neuropathies including glaucoma and macular degeneration, and disorders of photoreceptor degeneration such as retinitis pigmentosa; metabolic, mitochondrial or infectious brain abnormalities such as encephalitis, or suffers from neuropathic pain (see, for example, Lipton and Rosenberg, *New Engl. J. Med.* 330: 613 (1994)).

Cells can be transplanted into a patient, for example, into the brain or spinal cord using well known methods for transplanting or "grafting" neurons as described, for example, in McDonald et al., *Nat. Med.* 5:1410-1412 (1999), and summarized in Dunnett et al., *Brit. Med. Bulletin* 53:757-776 (1997). Methods for preventing or ameliorating rejection, for example, using cyclosporinA treatment, also are known in the art.

Those skilled in the art understand that the steps of contacting the progenitor cells with a differentiating agent and inducing the p38 MAP kinase/MEF pathway can be performed in any order or simultaneously. It further is understood that a progenitor population in which the p38 MAP kinase/MEF2 pathway has been induced can be transplanted into a patient prior to, during or after differentiation of the progenitor cells into neuronal cells. In one embodiment, cells are transplanted prior to or during differentiation. Where cells are transplanted prior to differentiation, the neuronal environment can drive the cells into the desired neuronal cell type, rather than, for example, muscle cells due to the presence of the appropriate environmental cues. In view of the above, it is clear that differentiation can occur in vitro or in vivo, or can occur partially in vitro and partially in vivo.

The invention further provides a pharmaceutical composition containing a MEF2 mimetic, which is a peptide or non-peptide molecule that mimics MEF2 function. The invention further provides a pharmaceutical composition containing a p38 mimetic, which is a peptide or non-peptide molecule that mimics p38 function.

Further provided by the invention is a pharmaceutical composition containing a MEF2 activator and a caspase inhibitor. MEF2 activators have been described herein above and include small molecules that result in increased expression or activity of a MEF2 polypeptide or that mimic MEF2 function. A MEF2 activator can be an organic chemical, drug, nucleic acid molecule, peptide, peptidomimetic, polypeptide or other naturally or non-naturally occurring organic molecule, and can be, for example, a MEF2 mimetic. Exemplary MEF2 activators are transcription factors that upregulate MEF2 expression, molecules that compete for binding to a MEF2 inhibitor such as Cabin1 or histone deacetylase, and kinases that activate MEF2 polypeptides such as p38α.

In one embodiment, the invention provides a pharmaceutical composition containing a nucleic acid molecule encoding a constitutively active MEF2 polypeptide, and a caspase inhibitor. Constitutively active MEF2 polypeptides have been described herein and can be prepared by methods well known in the art. A caspase inhibitor useful in a pharmaceutical composition of the invention can be any of the caspase inhibitors described above or another inhibitor well known in the art and can be, for example, a selective caspase inhibitor.

The present invention also provides a method of identifying a protective or differentiation gene, which can be, for example, a neuroprotective gene or a gene that contributes to neuronal or muscle cell differentiation. A method of the invention includes the steps of isolating a first cell population; isolating a second cell population, wherein the second cell population has an altered level or activity of a MEF2 polypeptide as compared to the first cell population; and assaying for differential gene expression in the first cell population as compared to the second cell population, whereby a gene differentially expressed in the second cell population as compared to the first cell population is identified as a protective or differentiation gene. In one embodiment, the first cell population is a progenitor cell population, the second cell population is a neuronal cell population, and the differentially expressed gene is a neuronal differentiation gene. In a further embodiment, the first cell population is a progenitor cell population, the second cell population is a muscle cell population, and the differentially expressed gene is a muscle differentiation gene. In yet another embodiment, both cell populations are neuronal cell populations, the second cell population has been subject to a neuronal stress as compared to the first cell population, and the differentially expressed gene is a neuroprotective gene.

It is understood that the term "cell population" can mean a single cell or a collection of cells. In one embodiment, the first and second cell populations each are single cells. Where the cell populations are made up of more than a single cell, the cell populations can be homogeneous or heterogeneous. Furthermore, where the cell populations are made up of more than a single cell, it is understood that, while the second cell population as a whole has an altered level or activity of a MEF2 polypeptide as compared to the first cell population as a whole, there may or may not be an altered level or activity when individual cells from the first and second cell populations are compared.

An altered level of expression or activity of a MEF2 polypeptide can be achieved, for example, by comparing a particular tissue or cell of interest from a MEF2 knockout or conditional knockout mouse with a wild-type littermate. Cells or tissue samples can be obtained, for example, from the cerebrocortex or hippocampus of the brain or from cardiac muscle.

Further provided by the invention is a method of identifying a protective gene in vitro. The method is practiced by inducing the p38/MEF2 pathway in a cell in vitro to produce a protected cell; stressing the cell; and assaying for differential gene expression in the protected cell as compared to gene expression in a control cell, whereby a gene differentially expressed in the protected cell as compared to the control cell is identified as a protective gene. In such a method of the invention, the p38/MEF2 pathway can be induced, for example, by introducing into the cell a nucleic acid molecule encoding a MEF2 polypeptide. The MEF2 polypeptide can be, for example, a human MEF2 polypeptide and further can be, if desired, a constitutively active MEF2 polypeptide. In one embodiment, a neuroprotective gene is identified by inducing the p38/MEF2 pathway in a neuron. In another embodiment, a muscle protective gene is identified by inducing the p38/MEF2 pathway in a muscle cell. In a method of the invention, the differential gene expression that identifies the protective gene can be increased or decreased gene expression.

The invention additionally provides a method of identifying a differentiation gene in vitro by inducing the p38/MEF2 pathway in a progenitor cell in vitro to produce a differentiated cell; and assaying for differential gene expression in the differentiated cell as compared to gene expression in a control cell, whereby a gene differentially expressed in the differentiated cell as compared to the control cell is identified as a differentiation gene. In a method of the invention, the p38/MEF2 pathway can be induced, for example, by introducing into the progenitor cell a nucleic acid molecule encoding a MEF2 polypeptide. The MEF2 polypeptide can be, for example, a human MEF2 polypeptide or a constitutively active MEF2 polypeptide. In one embodiment, the differentiated cell is a neuronal cell, and, in a further embodiment, the differentiated cell is a muscle cell. The differential gene expression which serves to identify the differentiation gene can be increased or decreased gene expression.

A variety of means are well known in the art for assaying for differential gene expression. Such means include, for example, differential display such as mRNA differential display and differential display RT-PCR (DDRT-PCR); RNA fingerprinting; subtractive hybridization approaches and microarrays such as DNA microarrays. Differential display analysis can be used in a method of the invention, for example, as described in Jo et al., *Methods Enzymol.* 332:233-244 (2001); Staege et al., *Immunogenetics* 53:105-113 (2001); Fujimoto et al., *Hepatol. Res.* 20:207-215 (2001). In addition, suppressive subtractive hybridization can be used to assay for differential gene expression in a method of the invention, for example, as described in Robert et al., *Biol. Reprod.* 64:1812-1820 (2001). Microarrays such as high-density oligonucleotide arrays and cDNA microarrays also can be useful for assaying for differential gene expression in a method of the invention and are well known in the art (see, for example, Lee et al., *Science* 285:1390-1393 (1999); Zirlinger et al., *Proc. Natl. Acad. Sci., USA* 98:5270-5275 (2001); Tsunoda et al., *Anticancer Res.* 21:137-143 (2001) and Khanna et al., *Cancer Res.* 61:3750-3759 (2001)). One skilled in the art understands that these and other methods for assaying for differential gene expression can be used in a method of the invention.

The following examples are intended to illustrate but not limit the present invention.

Example I

Induction of MEF2 Expression in P19 Cells

This example demonstrates that retinoic acid induces MEF2 protein expression in P19 embryonic carcinoma cells.

P19 embryonal carcinoma cells terminally differentiate into neuronal cells after retinoic acid treatment, and the process of neurogenesis in P19 cells is similar to that of the mammalian central nervous system (McBurney, *Int. J. Dev. Biol.* 37:135-140 (1993) and Bain et al., *Bioessays* 16:343-348 (1994)). Moreover the apoptotic cell death observed in neuronally-differentiating P19 cells parallels that seen in the fetal brain (Slack et al., *J. Cell Biol.* 129:779-788 (1995); Mukasa et al., *Biochem. Biophys. Res. Commun.* 232:192-197 (1997); Blaschke et al., *Development* 122:1165-1174 (1996); Jacks et al., *Nature* 359:295-300 (1992); and Kuida et al., *Nature* 384:368-372 (1996)).

MEF2, especially MEF2C, is expressed during neurogenesis in the rodent cerebral cortex (Leifer et al., *Proc. Natl. Acad. Sci. USA* 90:1546-1550 (1993)). To examine if MEF2 proteins are expressed during neurogenesis of P19 cells, gel shift assays were performed using the MEF2 binding site as a probe. While only very faint binding activity was detected in undifferentiated P19 cells, binding activity increased to high levels two days after retinoic acid treatment (FIG. 6A, lanes 1 and 2). Unlabeled MEF2 oligonucleotide abrogated the binding activity, indicating the specificity of the binding to the MEF2 site (FIG. 6A, lanes 3 and 4). Although anti-MEF2A antibody did not affect the formation of the complex (FIG. 6B, lanes 5 and 6), anti-MEFC and anti-MEF2D antibodies supershifted the bands (FIG. 6B, lanes 7 and 8), indicating the presence of MEE2C and MEF2D proteins in the complex. Immunoblotting revealed that the level of MEF2C and MEF2D proteins increased after retinoic acid treatment (FIG. 6C). These results indicate that retinoic acid treatment induces MEF2 site-binding activity by MEF2C and MEF2D and an increase in MEF2C and MEF2D protein expression during neurogenesis of P19 cells.

Neuronal differentiation of P19 cells was induced as follows. P19 cells were purchased from the ATCC(CRL 1825) and maintained in a modified Eagle's minimum essential medium (MEM; Sigma, St. Louis, Mo.), supplemented with 10% heat inactivated fetal bovine serum (Intergen Co., Purchase, New York). For neuronal differentiation, $1\times10^6$ P19 cells were cultured in a 10 cm diameter tissue culture dish with 300 pM 13-cis retinoic acid (Eastman Kodak, Rochester, N.Y.) for two days. After trypsinization, the cells were again exposed to 300 pM retinoic acid and re-seeded onto a bacterial grade Petri dish to allow the cells to aggregate, thereby facilitating neuronal differentiation. After a one day incubation, cell aggregates were collected and dissociated with trypsin-EDTA. The dissociated cells were plated onto a tissue culture chamber slide (Nunc, Rochester, N.Y.). The medium was changed the day after plating and every two days thereafter.

Gel shift assays were performed as follows. Nuclear extracts of undifferentiated or retinoic acid-treated P19 cells were prepared as previously described (Okamoto et al., *Brain. Res. Mol. Brain. Res.* 74:44-54 (1999)). Protein concentrations were measured with a Micro BCA Protein Assay Reagent Kit (Pierce, Rockford, Ill.) using albumin as the standard. Nuclear extracts (5 µg/20 µl) were preincubated on ice for 10 minutes in a solution containing 20 mM Tris (pH 7.6), 10% glycerol, 1 mM dithiothreitol, 80 mM KCl, and 1 µg poly (dl-dC)•(dl-dC). 32P-end-labeled double stranded oligonucleotide representing the MEF2 binding site (TGGGCTATAAATAGCCGC; SEQ ID NO: 12) of the brain-specific creatine kinase gene was then added and incubated at room temperature for 20 minutes. The binding mixture was then electrophoresed on a 6% nondenaturing acrylamide gel in 0.25×TBE for 1.5 h at 150 V. For supershift assays, antibodies against MEF2A (Santa Cruz Biotechnology, Inc., Santa Cruz, Calif.), MEF2C (Leifer et al., *Proc. Natl. Acad. Sci., USA* 90:1546-1550 (1993)), or MEF2D (provided by Dr. B. Kosofsky, Massachusetts General Hospital, Boston) were added to the preincubation binding mixtures.

Immunoblotting was performed as follows. Whole cell lysates were prepared in RIPA buffer containing 0.1 mg/ml PMSF and 1 mM sodium vanadate. Proteins in 50 µg aliquots were separated by SDS-PAGE and then transferred onto a nitrocellulose membrane (Amersham Life Science, Piscataway, N.J.). Membranes were incubated overnight at 4° C. with primary antibody to MEF2C (1:1000), MEF2D (1:500), phospho p38 (1:1000, New England Biolabs, Inc., Beverly, Mass.), or p38α (1:1000, Santa Cruz Biotech). Horseradish peroxidase-linked anti-rabbit IgG (Vector) was used as the secondary antibody. Immunoblots were visualized with an enhanced chemiluminescence system (ECL, Amersham Pharmacia Biotech, Piscataway, N.J.).

Example II

Overexpression of MEF2C in P19 Cells

These results indicate that stable overexpression of MEF2C transforms p19 cells into a mixed neurogenic/myogenic phenotype expressing neurofilament as well as the myosin heavy chain.

P19 cells exposed to DMSO develop into myogenic cells while P19 cells exposed to retinoic acid develop along a neurogenic pathway (McBurney, M. W., *Int. J. Dev. Biol.* 37:135-140 (1993)). To examine the potential role of MEF2C in the differentiation process, MEF2C was overexpressed in stable transformants of undifferentiated P19 cells in the absence of retinoic acid or DMSO. Undifferentiated P19 cells lacked immunoreactivity with MEF2C and also lacked neurofilament (FIG. 6E). MEF2C-transfected cells expressed MEF2C protein in the nucleus, as determined by specific antibody labeling, and were neuronal in character as evidenced by labeling with anti-neurofilament. All transfected cells (from over 200 such cells scored) expressed MEF2C, stained with anti-neurofilament, and extended two neuronal-like processes, producing a bipolar appearance (FIG. 6F). None of the MEF2C-transfected cells stained positively for glial fibrillary acidic protein (GFAP), indicating that they did not manifest an astrocytic phenotype.

Overexpression of MEF2A has been shown to initiate the myogenic phenotype in the 10T1/2 fibroblast cell line (Kaushal et al., *Science* 266:1236-1240 (1994)) when co-expressed with other factors (MyoD or myogenin) (Molkentin et al., *Cell* 83:1125-1136 (1995)). Accordingly, P19 cells transfected with MEF2C were assayed for myogenic features by staining transfected cells with anti-myosin heavy chain antibody. All cells expressing MEF2C (over 200 counted) were also positive for myosin heavy chain label (FIG. 6G). Taken together, these results indicate that transfection of undifferentiated P19 cells with MEF2C induces a bipolar cell phenotype that expresses both neuronal (neurofilament) and myogenic (myosin heavy chain) markers.

MEF2C was overexpressed in P19 cells essentially as follows. The phosphoglycerate kinase gene promoter-driven expression vector (pGK) was kindly provided by Dr. M. W. McBurney (University of Ottawa, Canada). Human MEF2C cDNA was inserted between the BamHI and XhoI sites of pGK to produce the expression vector pGK-MEF2C. $2 \times 10^5$ P19 cells were plated in a 6 cm diameter dish 24 h prior to transfection. Subsequently, 25 µg of the MEF2C expression vector (pGK-MEF2C) and 1 µg of the neomycin resistance gene expression vector (pSV neo) were co-transfected by calcium phosphate precipitation. The cells were washed 16 hours post-transfection and cultured in MEM with 10% serum. After 24 hours, the cells were trypsinized and seeded onto a tissue culture chamber slide. The cells were maintained in 200 µg/ml Geneticin for 5 days to select the transfected cells.

Immunocytochemistry was performed as follows. Cultures were fixed with 3% paraformaldehyde at room temperature for 40 minutes. After washing three times with PBS, cells were permeabilized with 0.3% Triton x-100 for 5 minutes. The free aldehyde groups formed during the fixation were reduced by incubation with 1 mg/ml sodium borohydride three times for 5 minutes each. Cells were then washed three times in PBS. The fixed cells were incubated at 4° C. overnight with primary monoclonal antibodies to microtubule-associated protein 2 (MAP2, 1:500; Sigma, clone HM-2), neurofilament H (1:250; Sternberger Monoclonals Inc., Lutherville, Md., SMI311), myosin heavy chain (1:250; Developmental Studies Hybridoma Bank, University of Iowa, Iowa, MF20), glial fibrillary acidic protein (GFAP, 1:400; Sigma, clone G-A-5), or rabbit antiserum to MEF2C (1:250) (Leifer et al., supra, 1993). Cells were then washed three times in PBS containing 0.2% Tween 20, and rhodamine-conjugated anti-mouse IgG or fluorescein-conjugated anti-rabbit IgG (each at 1:100; Boehringer Mannheim, Indianapolis, Ind.) was added as the secondary antibody. After a one hour incubation at room temperature, the cells were washed again and mounted. For Hu- and nestin-staining, cells were fixed with acid ethanol (95% ethanol: 5% acetic acid) for 30 minutes at room temperature. The fixed cells were then washed three times with PBS and incubated with a monoclonal antibody to Hu (1:200, gift of Drs. M. F. Marusich and J. A. Weston, University of Oregon, Oreg.) or to nestin (1:20, Developmental Studies Hybridoma Bank, Rat-401). After overnight incubation at 4° C., the samples were further washed and incubated with anti-mouse immunoglobulins conjugated to horseradish peroxidase (1:100; DAKO Corp., Carpinteria, Calif.). A peroxidase reaction was performed using 3,3'-diaminobenzidine tetrahydrochloride (Sigma). Stained preparations were examined under epifluorescence microscopy.

Example III

Characterization of P19 Clones Stably Expressing a Dominant Negative Form of MEF2

This example describes the characterization of P19 clones in which MEF2C function is inhibited.

The role of endogenous MEF2 proteins in retinoic acid-induced neuronal differentiation of P19 was analyzed using a dominant negative form of MEF2. MEF2 proteins are functionally divided into two regions. The N-terminal region (containing the MADS and MEF2 domains) is responsible for specific DNA binding activity, while the C-terminal region is necessary for transcriptional activity (Martin et al., *Mol. Cell. Biol.* 14:1647-1656 (1994), and Molkentin et al., *Mol. Cell. Biol.* 16:2627-2636 (1996)). Since the MADS and MEF2 domains alone lack transcriptional activity, the N-terminal region of MEF2 acts as a dominant negative construct (Martin et al., *Mol. Cell. Biol.* 14:1647-1656 (1994)). Dominant negative MEF2 has been shown to inhibit myotube formation in myoblastic cell lines (Ornatsky et al., *J. Biol. Chem.* 272: 33271-33278 (1997)).

Figure 7A:
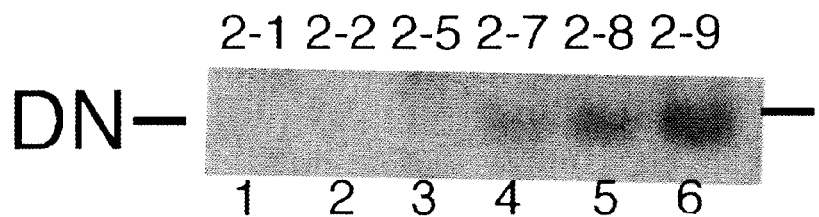
FIG. 7 shows inhibition of MEF2 function decreases the number of neuronal (MAP2-positive) P19 cells after retinoic acid treatment. (A) Undifferentiated P19 cells were stably transfected with empty vector (clones 2-1, 2-2 and 2-5 in lanes 1-3, respectively) or MEF2 dominant negative (clones 2-7, 2-8 and 2-9 in lanes 4-6, respectively). Expression of the MEF2 dominant negative was demonstrated in a gel shift assay using a radiolabeled MEF2 site oligonucleotide and nuclear extracts of each clone. DN: binding complex of the MEF2 site and dominant negative MEF2 protein. (B and C) Cultures from control (B, clone 2-1) and MEF2 dominant negative (C, clone 2-7) transformants were treated with retinoic acid for 7 d to induce neurogenesis, and neuronal differentiation was then evaluated by immunocytochemistry with anti-MAP2. (D) Control cultures (clones 2-1,2-2, 2-5) and MEF2 dominant negative cultures (clones 2-7,2-8, 2-9) were treated with retinoic acid and scored for the number of MAP2-positive cells (n=6 experiments; *, P<0.0001 by ANOVA and post-hoc comparison).

Stable transformants of P19 cells were established which expressed the dominant negative N-terminus of MEF2C (residues 1 to 105). Three "vector-alone" transfected control clones were designated clones 2-1, 2-2 and 2-5; three clones expressing the MEF2 dominant negative were designated clones 2-7, 2-8 and 2-9. As a further control, two additional clones expressing a mutated form of the MEF2 dominant negative construct were produced and designated clones 2-16 and 2-21. Expression of the MEF2 dominant negative was monitored with gel shift assays. Binding activity of the MEF2 dominant negative was detected for clones 2-7, 2-8 and 2-9, but not for control clones 2-1, 2-2, 2-5, 2-16, or 2-21 (FIG. 7A and data not shown). All transformants were morphologically indistinguishable from parent P19 cells.

The MEF2C dominant negative construct and a control were prepared as follows. Dominant negative MEF2C (amino acids 1-105) tagged with a flag sequence (pcDNAI-MEF2C 1-105 flag) and constitutively active MEF2C (pcDNAI- MEF2C 1-117/VP16) were obtained from Dr. Eric N. Olson (Southwestern Medical Center, Dallas). MEF2C 1-105 flag acts as a MEF2 dominant negative by binding to the MEF2 site without producing activation since it lacks the transactivation domain (Molkentin et al., *Mol. Cell. Biol.* 16:2627-2636 (1996)). MEF2C 1-105 flag cDNA was ligated into the BamHI/XhoI sites of pGK to produce pGK-DN. A mutation was engineered in the MEF2 dominant negative by changing the arginine residue at position 24 to a leucine, and this plasmid was designated pGK-DNmt. The mutated MEF2 dominant negative was unable to bind to the MEF2 site and therefore served as control to rule out the possibility that the MEF2 dominant negative was affecting cell survival nonspecifically by binding to sites other than MEF2.

Stable transfection of P19 cells with a dominant negative form of MEF2 was performed as follows. Using the calcium phosphate precipitation method, $2 \times 10^5$ P19 cells were transfected with 24 µg of an empty expression vector (pGK), an expression vector encoding a dominant negative MEF2 (pGK-DN), or a mutated dominant negative MEF2 construct (pGK-DNmt) in addition to the neomycin resistance gene (pSV neo). The transfected cells were selected by exposure for 10 days to 200 µg/ml Geneticin. The selection medium was changed every two days. Stable clones expressing the MEF2 dominant negative and the mutated MEF2 dominant negative were selected with the reverse transcriptase-polymerase chain reaction.

Example IV

Inhibition of MEF2 Function Diminishes the Number of Neuronal Cells

This example demonstrates that the number of neuronal cells formed upon treatment of P19 cells with a neuronal differentiation stimulus is reduced when MEF2C function is inhibited.

Figure 7B:
Figure 7C:
Figure 7D:
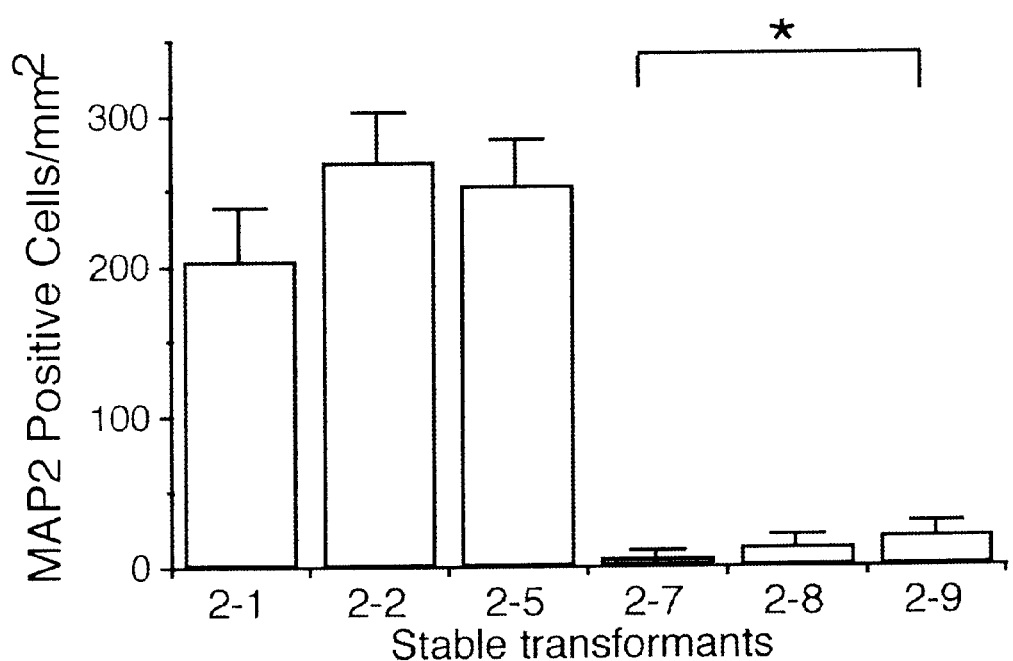

Neuronal differentiation occurs via multiple sequential steps (Stemple and Mahanthappa, *Neuron* 18:1-4 (1997)). Nerve cells differentiate from unipotent progenitors, which arise from multipotent precursor cells. The effect of the MEF2 dominant negative on these steps of neuronal differentiation was monitored by analyzing the appearance of differentiated neurons using antibodies to neuronal markers, such as neurofilament and MAP2. Stable transformants expressing a dominant negative form of MEF2C which inhibits MEF2 function were treated with retinoic acid to induce neuronal differentiation. After seven days, cells were fixed and stained with anti-MAP2 antibody. Although many MAP2-positive cells appeared in the control cultures (FIG. 7B), the number of MAP2-positive cells was dramatically reduced in the MEF2 dominant negative cultures (FIG. 76). The difference between the number of MAP2-positive cells in the MEF2 dominant negative cultures and the control cultures was statistically significant (FIG. 7D).

Example V

Inhibition of MEF2 Function Reduces the Number of Progenitor Cells

This example demonstrates that the number of progenitor cells is reduced by inhibition of MEF2c function with a dominant negative construct.

The number of precursor cells (multipotent precursor or unipotent precursor cells) was analyzed following inhibition of MEF2 function. The appearance of multipotent progenitors (nestin-positive cells) and unipotent precursors (Hu-positive cells) was monitored in control (clone 2-1) and MEF2 dominant negative cultures (clone 2-7). Nestin-positive and Hu-positive cells were counted before and after retinoic acid treatment for 3.0 days and 3.5 days, respectively. At these time points, naultipotent precursor cells (3.0 days) followed by unipotent precursor cells (3.5 days) appear in these cultures prior to the neuronally differentiated state (McBurney, M. W., *Int. J. Dev. Biol.* 37:135-140 (1993)). Hu-positive and nestin-positive cells were induced after retinoic acid treatment in both control (clone 2-1) and MEF2 dominant negative cultures (clone 2-7; FIGS. 7A and C). However, the number of Hu-positive and nestin-positive cells in the MEF2 dominant negative cultures was significantly smaller than the number of Hu-positive and nestin-positive cells in control cultures (FIGS. 7B and D). These results indicate that interference with MEF2 activity can reduce the number of multipotent precursor and unipotent progenitor cells.

Example VI

Inhibition of MEF2 Function Enhances Apoptotic Cell Death During Neuronal Differentiation This example demonstrates that apoptotic cell death increases during neuronal differentiation by inhibition of MEF2C function.

Apoptotic cell death of differentiating cells is found widely in the developing fetal brain (Blaschke et al., *Development* 122:1165-1174 (1996)), and apoptosis is also observed during the course of neuronal differentiation of P19 cells (Slack et al., *J. Cell Biol.* 129:779-788 (1995), and Mukasa et al., *Biochem. Biophvs. Res. Commun.* 232:192-197 (1997)). To examine the number of multipotent and unipotent precursor cells following interference with MEF2 cells, nuclear morphology was analyzed with the DNA dye Hoechst 33342 (FIG. 9A) to score the number of apoptotic cells after three days of retinoic acid treatment, at which time multipotent precursors were detected. Prior to the addition of retinoic acid, fewer than 1% of the cells exhibited apoptotic nuclei in control or MEF2 dominant negative cultures. After three days of retinoic acid treatment, a significant number of cells displayed apoptotic nuclei in the controls (transfected with either empty vector or the mutated form of the MEF2 dominant negative; FIGS. 9B and C). However, apoptosis was increased in the MEF2 dominant negative cultures (FIG. 9B). These findings were confirmed by another apoptosis assay using the TUNEL technique (FIG. 9D). Additionally, the number of apoptotic cells was increased in the MEF2 dominant negative cultures after 3.5 days of retinoic acid treatment, when unipotent precursor cells predominated. These results indicate that interference with MEF2 activity can increase apoptotic cell death during neuronal differentiation of P19 cells and can lead to a reduction in the number of multipotent and unipotent precursor cells. These results also indicate that MEF2 transcriptional activity can be essential for prevention of cell death during neuronal development.

Apoptotic assays were performed as follows. Cells were incubated with the DNA dye Hoechst 33342 (1 µg/ml) for 5 minutes at 37° C. to observe nuclear morphology. After washing with PBS, cells were fixed with acid ethanol (95% ethanol: 5% acetic acid) for 10 minutes at room temperature. Samples were then washed with distilled water three times and mounted. Apoptotic nuclei were counted at 400× magnification. Within several hours of dying by apoptosis, cells underwent secondary necrosis (since they were not phagocytosed in these cultures) and detached from the substrate (Bonfoco et al., *Proc. Natl. Acad. Sci. USA* 92:7162-7166 (1995)). Hence, several hours after apoptotic cell death, dead cells were no longer present to be stained by Hoechst dye. This temporal separation made it possible to distinguish the number of cells recently undergoing apoptosis by using sequential Hoechst staining at different time points. Additionally, terminal deoxynucleotidyl transferase-mediated dUTP nick-end labeling (TUNEL) assays were performed in a blinded fashion using an In Situ Cell Death Detection Kit tagged with tetramethyl-rhodamine (Roche, Nutley, N.J.) or an Apoptosis Detection System Kit tagged with fluorescein (Promega Corporation, Madison, Wis.).

Example VII

Inhibition of MEF2 Function does not Affect Cell Division of Multipotent Precursor Cells This example demonstrates that MEF2 transcriptional activity has no significant effect on cell division of multipotent precursor cells.

Multipotent precursor cells are known to proliferate, leading to an expansion of the cell population that can eventually differentiate into neurons. Cells transfected with dominant negative MEF2 were analyzed for an effect on the proliferation of multipotent precursor cells. Control and MEF2 dominant negative cultures were treated with retinoic acid for 3.0 days, followed by addition of BrdU for detection of dividing cells. BrdU-positive cells and multipotent precursor cells were identified by double labeling with anti-BrdU and anti-nestin antibodies, respectively (FIG. 9E). The percentage of cells positive for both BrdU and nestin (proliferating, multipotent precursor cells) was similar in the control and MEF2 dominant negative cultures (FIG. 9F). These results indicate that MEF2 transcriptional activity has no significant effect on cell division of multipotent precursor cells.

Cell proliferation assays were performed as follows. To label proliferating cells, bromodeoxyuridine (BrdU; Amersham Life Science) was added to cultures at a dilution of 1:1000 for two hours at 37° C. After washing with PBS, cells were treated with acid ethanol (95% ethanol: 5% acetic acid) for 30 minutes at room temperature and cellular DNA was denatured with 2N HCl. After an additional wash in PBS, cells were incubated at 4° C. overnight in rat monoclonal anti-BrdU antibody (1:10; Harlan Sera-Lab Limited, Indianapolis, Ind.) and mouse monoclonal anti-nestin antibody (11 µg/ml). After three washes in PBS, secondary antibodies were added: Rhodamine Red-X-conjugated anti-rat IgG (1:200) and Biotin-SP-conjugated anti-mouse IgG (1:50; Jackson ImmunoResearch Laboratories, Inc.; Westgrove, Pa.) followed by streptavidin-fluorescein (1:25; Amersham Life Science Inc.). Cells were examined under epifluorescence microscopy.

Example VIII

Inhibition of P38 MAP Kinase Increases Apoptosis During Neuronal Differentiation This example demonstrates that the p38α/MEF2 cascade plays a role in preventing apoptotic cell death during neuronal differentiation.

Interference with MEF2 function enhanced apoptosis in differentiating P19 cells, indicating that MEF2 transcriptional activity was necessary for prevention of cell death during neuronal development. Two members of the p38 MAP kinase family, p38 α and p38β$_2$, are known to activate MEF2 via phosphorylation of Ser/Thr residues (Han et al., *Nature* 386:296-299 (1997); Zhao et al., *Mol. Cell. Biol.* 19:21-30 (1999); and Yang et al., *Mol. Cell. Biol.* 19:4028-4038 (1999)). Moreover, the p38 MAP kinase family can play a role in cell survival in several cell types (New and Han, *Trends Cardiovasc. Med.* 8:220-229 (1998)).

Figure 10A:
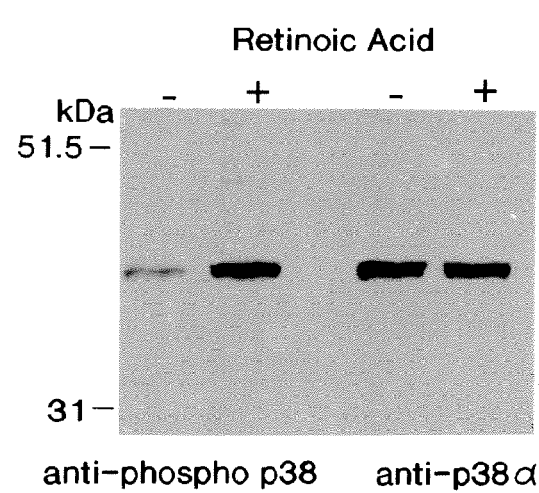
FIG. 10 shows involvement of the p38α/MEF2 pathway in preventing apoptosis during neuronal differentiation of P19 cells. (A) p38α was phosphorylated during induction of neuronal differentiation by retinoic acid. Anti-phospho p38 was used to detect activated/phosphorylated p38 family members on immunoblots during induction of neuronal differentiation. The same membrane was then stripped and re-blotted with a p38α-specific antibody that labeled the same band. (B) Dominant negative p38α (p38αDN) enhanced apoptosis during neuronal differentiation. Constitutively active MEF2C (MEF2C/VP16) significantly rescued the differentiating cells from apoptosis. Dominant negative p38β$_2$ (p38β$_2$DN) had no effect on apoptosis compared to control (expression vector only). After treatment with retinoic acid for one day, cells were transfected with the indicated expression vector(s) along with a GFP expression vector to identify the transfected cells. The number of transfected apoptotic cells was determined in a blinded fashion by TUNEL assay on day 3 of retinoic acid treatment. Over 1200 GFP-positive cells were scored in each culture. Mean±SD are shown from three experiments (*, P<0.001; †, P<0.01 by ANOVA and post-hoc comparison).

The p38/MEF2 pathway was examined for a role in preventing apoptosis in differentiating P19 cells. Activation of p38 family members was examined by immunoblotting with an anti-phospho-pan p38 antibody, which recognizes all activated/phosphorylated p38 MAP kinases. One band was strongly induced after retinoic acid treatment, and the mobility of this band was the same as p38α (FIG. 10A). Total (phosphorylated and unphosphorylated) p38α protein appeared to be present at similar levels before and after stimulation with retinoic acid (FIG. 10A, right-hand lanes). In contrast, p38β$_2$ was undetectable with two different antibodies, although these antibodies clearly reacted with recombinant p38β$_2$ protein under the same conditions in control studies. These results indicate that p38α is activated/phosphorylated during the induction of neurogenesis.

Figure 10B:
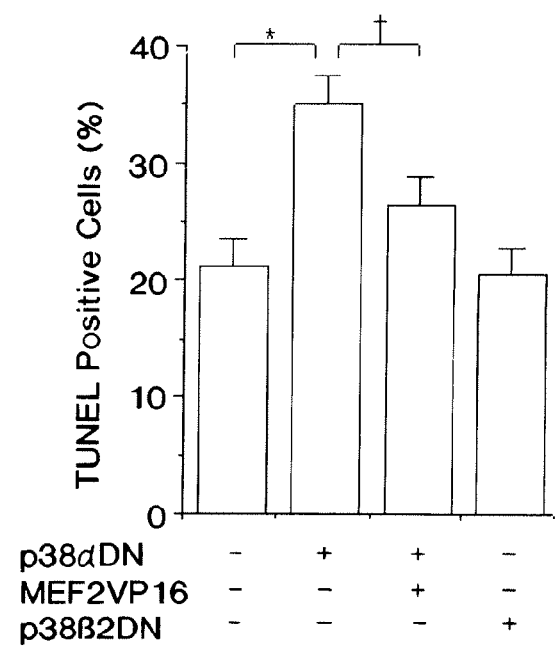

Transfection of dominant negative p38α, but not dominant negative p38β$_2$, enhanced apoptotic cell death in differentiating cells. Furthermore, co-expression of constitutively active MEF2C significantly rescued these differentiating cells from apoptosis (FIG. 10B). These findings indicate that the p38α/MEF2 cascade plays a role in preventing apoptotic cell death during neuronal differentiation.

Transient transfection during differentiation of P19 cells was performed as follows. P19 cells ($2\times10^5$) were seeded onto 6-well tissue culture plates and treated with 300 pM retinoic acid to induce neuronal differentiation. One day later, cells were transfected with 0.83 µg of a p38 dominant negative construct or vector alone [pcDNA3-p38α (AF), pcDNA3-p38β$_2$ (AF) or pcDNA3], 0.83 µg of a constitutively active MEF2C construct or vector alone (pcDNAI-MEF2C 1-117/VP16 or pcDNAI-Amp), plus 0.33 µg of a Green Fluorescent Protein (GFP) construct to identify transfected cells (pEGFP—N1). A lipid based transfection system was utilized (6 ml of TransFast, Promega). The next day cells were transferred to 3.5-cm bacterial dishes and treated with an additional 300 pM retinoic acid. TUNEL assays were performed on day three after initiating retinoic acid differentiation. Over 1200 GFP-positive cells were scored for apoptosis from each culture plate under epifluorescence microscopy, and each experiment was replicated on three separate days.

Example IX

Expression of Constitutively Active MEF2 in Undifferentiated ES Cells

A. Expression of Constitutively Active MEF2

Murine embryonic stem cells (ES cell line D3) were plated at a 1:5 dilution in ES Cell Passage Medium (DMEM with 20% fetal bovine serum, 2250 mg/L glucose, MEM non-essential amino acids, 1 mM sodium pyruvate and penicillin-streptomycin) in gelatin-coated 24 well plates. One day later, ES cells were incubated for five hours with a mixture of 1.25 µg of vector alone (pcDNA1) or pcDNA expression vector encoding constitutively active MEF2 (pcDNA MEF2C/VP16), 0.25 µg expression vector encoding green fluorescence protein (GFP; pEGFPN1; Clontech), and 3 µl of LipofectAMINE 2000 (Promega). Transfected cells were identified by expression of GFP. Cells were washed twice with Neuron Induction Medium (DMEM with 10% bovine calf serum, 4500 mg/L glucose, 10% F-12 growth supplement, 1 mM glutamine, 25 mM HEPES (pH 7.0) and penicillin-streptomycin). Further incubation for one day in Neuron Induction Medium resulted in differentiation of ES cells to neurons as indicated by the presence of neuron-specific markers (see below).

B. Characterization of Differentiated ES cells

Cells were analyzed for expression of the neuron-specific marker, neurofilament H essentially as follows. Cells were trypsinized and transferred into a four-well chamber slide (Nunc) coated with laminin and poly-L-lysine. Two days later, cells were fixed with 3% paraformaldehyde and permeabilized with 0.3% Triton-X 100. Expression of neurofilament H was determined with monoclonal antibody to anti-neurofilament H monoclonal antibody SMI311 (Steprnberger Monoclonals) and detected with anti-mouse IgG conjugated to rhodamine Red-X (Jackson ImmunoResearch). Red (neurofilament H-positive, transfected (GFP-positive) cells were scored using epifluorescence microscopy. The results showed that eighty-three percent of transfected cells displayed expression of neurofilament H, indicating a high degree of efficiency in conversion of murine ES cells transfected with constitutively active MEF2C to neurons. Similar results were obtained with ES cells transfected with constitutively active MEF2A/VP16.

These results demonstrate that overexpression of constitutively active MEF2 (MEF2/VP16) induces neurogenesis in undifferentiated ES cells.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of transplantation, comprising the steps of:
   (a) contacting in vitro a population of progenitor cells with a differentiating agent;
   (b) introducing in vitro into said progenitor cells a nucleic acid molecule encoding a constitutively active MEF2 polypeptide or an active fragment thereof, wherein said constitutively active MEF2 polypeptide or active fragment thereof has transactivation activity that is independent of phosphorylation; and
   (c) transplanting said progenitor cells comprising said nucleic acid molecule into a patient to produce a cell population containing protected neuronal cells in said patient.

2. The method of claim 1, wherein said MEF2 polypeptide is human MEF2C, or an active fragment thereof.

3. The method of claim 1, wherein said constitutively active MEF2 polypeptide is a MEF2/VP16 fusion protein.

4. The method of claim 1, wherein said constitutively active MEF2 polypeptide contains one or more serine/threonine to aspartic acid/glutamic acid substitutions in the MEF2 transactivation domain.

5. The method of or claim 1, further comprising inhibiting caspase activity in said progenitor cells.

6. The method of claim 1, wherein said progenitor cells are human stem cells.

7. The method of claim 1, wherein said progenitor cells are embryonic stem cells.

8. The method of claim 7, wherein said embryonic stem cells are human embryonic stem cells.

9. The method of claim 1, wherein said progenitor cells are hematopoietic progenitor cells.

10. The method of claim 9, wherein said hematopoietic progenitor cells are human hematopoietic progenitor cells.

11. The method of claim 1, further comprising selecting CD133-positive human progenitor cells.

12. The method of claim 1, further comprising selecting CD133-positive/CD34-positive human progenitor cells.

13. The method of claim 1, further comprising selecting CD133-positive/CD34-negative human progenitor cells.

14. The method of claim 1, further comprising selecting CD133-positive/CD34-negative/CD45-negative human progenitor cells.

15. The method of claim 1, further comprising selecting CD34-negative/CD38-negative/Lin-negative human progenitor cells.

16. The method of claim 1, further comprising selecting CD34-positive/CD38-negative/Lin-negative/Thy-1-negative human progenitor cells.

17. The method of claim 1, wherein said differentiating agent is retinoic acid.

18. The method of claim 1, wherein said differentiating agent is selected from the group consisting of neurotrophic factor 3, epidermal growth factor, insulin-like growth factor 1 and a platelet-derived growth factor.

19. The method of claim 1, wherein said population containing protected neuronal cells comprises at least 50% neuronal cells.

20. The method of claim 1, wherein said nucleic acid molecule is stably introduced into said progenitor cells.

* * * * *